US008206698B2

(12) United States Patent
Koh et al.

(10) Patent No.: US 8,206,698 B2

(45) Date of Patent: Jun. 26, 2012

(54) METHOD OF TREATING A CUTANEOUS WOUND USING A COILED COIL CHIMERIC MOLECULE

(75) Inventors: Gou Young Koh, Daejeon (KR); Chung-Hyun Cho, Daejeon (KR)

(73) Assignee: Aprogen, Inc., Daejeon (KR)

( * ) Notice: Subject to any disclaimer, the term of this patent is extended or adjusted under 35 U.S.C. 154(b) by 0 days.

(21) Appl. No.: 12/728,158

(22) Filed: Mar. 19, 2010

(65) Prior Publication Data

US 2010/0256042 A1 Oct. 7, 2010

Related U.S. Application Data

(63) Continuation of application No. 11/576,146, filed as application No. PCT/IB2005/003655 on Sep. 28, 2005, now Pat. No. 7,691,365.

(51) Int. Cl.
*A61K 38/18* (2006.01)

(52) U.S. Cl. ......................... 424/85.1; 424/489; 514/1.1

(58) Field of Classification Search ........................ None
See application file for complete search history.

(56) References Cited

FOREIGN PATENT DOCUMENTS

WO WO 03/106501 A1 12/2003
WO WO 2005/051983 A2 6/2005

OTHER PUBLICATIONS

Zhou, et al., "Effects of Gene Delivery on Collateral Development in Chronic Hypoperfusion: Diverse Effects of Angiopoietin-1 Versus Vascular Endothelial Growth Factor," J. of the American College of Cardiology, 44:897-903, 2004.

Takahashi, et al., "Adenoviral-Delivered Angiopoietin-1 Reduces the Infarction and Attenuates the Progression of Cardiac Dysfunction in the Rat Model of Acute Myocardial Infarction," Molecular Therapy, 8(4):584-592, Oct. 2003.

Zhang, et al., "Angiopoietin-1 Reduces Cerebral Blood Vessel Leakage and Ischemic Lesion Volume After Focal Cerebral Embolic ischemia in Mice," Neuroscience, 113(3):683-687, 2002.

Thurston, et al., "Leakage-Resistant Blood Vessels in Mice Transgenically Overexpressing Angiopoietin-1," Science 286:2511, 1999.

Chae, et al., "Coadministration of Angiopoietin-1 and Vascular Endothelial Growth Factor Enhances Collateral Vascularization," Arterioscler Thromb Vasc Biol J. of the American Heart Association, 20:2573-2578, 2000.

Shyu, et al., "Direct Intramuscular Injection of Plasmid DNA Encoding Angiopoietin-1 but not Angiopoietin-2 Augments Revascularization in the Rabbit Ischemic Hindlimb," Circulation J. of the American Heart Association, 98:2081-2087, 1998.

Suri, et al., "Increased Vascularization in Mice Overexpressing Angiopoitin-1," Science, 282:467-471, 1998.

Cho Ch et al., "COMP-Ang1: a designed angiopoietin-1 variant with nonleaky angiogenic activity," Proc. Natl Acad Sci USA, 101(15): 5547-5552 (2004).

Cho Ch et al., "Designed angiopoietin-1 variant, COMP-Ang1, protects against radiation-induced endotheliai cell apoptosis," Proc Natl Acad Sci USA, 101(15): 5553-5558 (2004).

Shiraishi T et al., "Increased cytotoxicity of soluble Fas ligand by fusing isoleucine zipper motif," Biochem Biophys Res Commun, 322(1): 197-202 (2004).

*Primary Examiner* — Prema Mertz

(74) *Attorney, Agent, or Firm* — Joseph Hyosuk Kim; JHK Law

(57) ABSTRACT

The present application discloses a method of treating a disease that is treatable by therapeutic angiogenesis comprising administering to a needy subject an effective amount of a chimeric coiled coil molecule comprising a coiled-coil domain linked to a receptor binding domain of a ligand.

6 Claims, 48 Drawing Sheets

S: Signal sequence
CCD: coiled-coil domain (heptad repeat – parallel coiled-coil domain)
L : linker
FLD: fibrinogen-like domain

BSA

COMP-Ang1

A

B

A
Control
B
COMP-Ang1

A
Control
B
COMP-Ang1

FITC-lectin
PECAM-1
Merged
A
Control
B
C
D
Ad-COMP-Ang1
E
F

B 0w 1w
2w 6w
10w 16w

Control
COMP-Ang1
A
B
C
D
Control
COMP-Ang1
E
F
G
H
J

Control
COMP-Ang1
Control
COMP-Ang1
A
B
C
D
E
F
G
H
I
J
K
L

Tie2-EGFP
PECAM-1
Merged
Ade-LacZ (2 wk)
COMP-Ang1 (2 wk)
Ade-COMP-Ang1 (2 wk)
Ade-COMP-Ang1 (16 wk)
A
B
C
D
E
F
G
H
I
J
K
L A
Control
COMP-Ang1
D3
D7
D28
B
Control
COMP-Ang1
D28
C
Healing Length (um)
500
400
300
200
100
0
HL
COMP-Ang1
Control
0
3
7
14
28
Days
*

D

E

F

C
Control
COMP-Ang1
D
Lymphatic vessel
Area density (%)
2
1
0
2
4
Weeks
E
F
Blood Flow (ml/min/100g)
50
40
30
20
10
0
1
2
3
4
5
6
7
8
9
Portion
Control
COMP-Ang1

Control
eNOS (-/-)
COMP-Ang1
eNOS (-/-)
0
1
2
3
4
5
Wk
A
Wound area (%)
120
100
80
60
40
20
0
COMP-Ang1
Control
*
B Control
COMP-Ang1
0
1
2
4 weeks
A
Wound area (%)
120
100
80
60
40
20
0
COMP-Ang1
Control
*
*
0
1
2
4
Weeks
B

METHOD OF TREATING A CUTANEOUS WOUND USING A COILED COIL CHIMERIC MOLECULE

CROSS-REFERENCE TO RELATED APPLICATIONS

The present application is a continuation of U.S. application Ser. No. 11/576,146, filed Mar. 27, 2007, now U.S. Pat. No. 7,691,365, which is a U.S. national phase application under 35 USC 371 of PCT/IB2005/003655, filed Sep. 28, 2005, the contents of which are incorporated by reference herein in their entirety.

BACKGROUND OF THE INVENTION

1. Field of the Invention

The present invention provides for novel applications of chimeric coiled-coil molecule such as COMP-Ang1 for producing therapeutic angiogenesis, enhancing wound healing, recovering artherosclerotic erectile dysfunction, preventing vascular leakages including in sepsis and diabetic retinopathy. The invention also provides for applications of the chimeric coiled-coil molecule such as COMP-Ang1 for any blood vessel related disease such as shock, adrenal cortical insufficiency, hypertension, arthritis, stroke, ischemic brain diseases, asthma, and so on.

2. Description of the Background

Angiopoietin family proteins include four different angiopoietins, namely, angiopoietin-1 (Ang1), angiopoietin-2 (Ang2), angiopoietin-3 (Ang3) and angiopoietin-4 (Ang4) (Yancopoulos et al., 2000, Nature 407:242-248; Koh et al., 2002, Exp Mol. Med. 34:1-11) (FIG. 1). Ang1 and Ang4 act as agonist to vascular endothelial cell specific receptor tyrosine kinase, Tie2, while Ang2 and Ang3 have been known to act as antagonist to Tie2 (Yancopoulos et al., 2000, Nature 407:242-248; Koh et al., 2002, Exp Mol. Med. 34:1-11) (FIG. 1). However, recent reports indicated that Ang2 and Ang3 also can act as agonist in context dependent manner (Kim et al., Oncogene. 2000 14:4549-4552; Lee et al., FASEB J. 18:1200-1208) (FIG. 1). Very recent report indicated that all angiopoietins also bind and activate another vascular endothelial cell specific receptor tyrosine kinase, Tie1 (Saharinen et al., 2005, J Cell Biol. 169:239-243) (FIG. 1). Activation of Tie2 and Tie1 are involved in vasculogenesis, angiogenesis, lymphangiogenesis, and maintenance of endothelium integrity (FIG. 1).

Many reports (Sufi et al., 1998, Science. 282:468-471; Thurston et al., 1999, Science. 286:2511-2514; Shyu et al., 1998, Circulation. 98:2081-2087; Chae et al., 2000, Arterioscler Thromb Vasc Biol. 20:2573-2578; Zhou et al., 2004, J Am Coll Cardiol. 44:897-903), indicate that Ang1 can be used for therapeutic angiogenesis in case of ischemic heart, limb, and brain because application of Ang1 produces healthy, non-leaky and stable blood vessel formation while currently used VEGF produces non-healthy, leaky and unstable blood vessel formation.

Biochemical organization of Ang1 is complicated. Schematic diagram of the protein structure of Ang1 indicates that amino acids 1-19 are the secretory signal sequences (S), amino acids 20-155 are the superclustering domain (SCD), amino acids 156-255 are the coiled-coil oligomeric domain (CCOD), amino acids 256-283 are the linker (L), and amino acids 284-498 are the fibrinogen-like domain (FLD) (FIG. 2). There are cysteines (C) at amino acids 41, 54, 265, 286, 315, 435, 437, 439, and 452 (FIG. 2). Once Ang1 is generated as recombinant protein, it is frequently insoluble, easily aggregated, stick and unstable in activity. For in vivo use of Ang1, a soluble, stable, and potent Ang1 variant, COMP-Ang1 was developed (Cho et al., PNAS 101:5547-5552, 2004; Cho et al., PNAS 101:5553-5558, 2004; U.S. patent application Ser. No. 10/273,180 and PCT/IB03/03814, which references are incorporated by reference herein in their entirety). COMP-Ang1 is more potent than native Ang1 in phosphorylating the Tie2 receptor in lung endothelial cells in vitro and in vivo (Cho et al., PNAS 101:5547-5552, 2004; Cho et al., PNAS 101:5553-5558, 2004; U.S. patent application Ser. No. 10/273,180 and PCT/IB03/03814).

SUMMARY OF THE INVENTION

Although many vascular growth factors have been considered for therapeutic angiogenesis, no molecule can produce healthy and safe angiogenesis without side effects. Application of the inventive COMP-Ang1 produces enhanced healthy, non-leaky and stable angiogenesis, lymphangiogenesis and blood flow during skin wound healing in a diabetic mouse model, ischemic hindlimb recovery, and recovery of penile erectile dysfunction in adult animal. COMP-Ang1 produces (1) specific increase number of blood vessels, (2) specific enlargement of blood vessels, (3) specific increase of lymphatic vessels, without overt pathologic changes (within physiological ranges) in the adult animals.

Vascular enlargement is a characteristic feature of angiopoietin-1 (Ang1)-induced changes in adult blood vessels. However, it is unknown whether tissues having Ang1-mediated vascular enlargement have more blood flow and whether the enlargement is reversible. We have recently created a soluble, stable and potent Ang1 variant, COMP-Ang1. In the present application, we investigated the effects of varied dose and duration of COMP-Ang1 on vascular enlargement and blood flow in the tracheal microvasculature of adult mice and explored a possible mechanism of long-lasting vascular enlargement. We found that COMP-Ang1 administered by adenoviral vector induced long-lasting vascular enlargement and increased tracheal blood flow. In contrast, short-term administration of COMP-Ang1 recombinant protein induced transient vascular enlargement that spontaneously reversed within a month. In both cases, the vascular enlargement resulted from endothelial proliferation. The COMP-Ang1-induced vascular remodeling is mainly mediated through Tie2 activation. Sustained overexpression of Tie2 could participate in the maintenance of vascular changes. Together, our findings indicate that sustained treatment with COMP-Ang1 can produce long-lasting vascular enlargement and increased blood flow.

Microvascular dysfunction is a major cause of impaired wound healing seen in diabetic patients. Therefore, re-establishment of structural and functional microvasculature could be beneficial to promote wound healing in these patients. Angiopoietin-1 (Ang1) is a unique and specific growth factor functioning to generate a stable and functional vasculature through the Tie2 and Tie1 receptors. Here, we determined the effectiveness of COMP-Ang1, a soluble, stable and potent Ang1 variant, on promotion of the healing process in cutaneous wounds of diabetic mice. An excisional full thickness wound was made in the dorsal side of tail of diabetic (db/db) mice, and mice were then treated systemically with adenovirus encoding COMP-Ang1 (Ade-COMP-Ang1) or with control β-gal (Ade-β-gal) virus, or treated topically with recombinant COMP-Ang1 protein or bovine serum albumin (BSA). Time course observations revealed that the mice treated with Ade-COMP-Ang1 or COMP-Ang1 protein showed accelerated wound closure, enhanced angiogenesis and lymphangiogenesis, and higher blood flow in the wound portion compared to mice treated with control virus or BSA. COMP-Ang1 promotion of wound closure and angiogenesis was not dependent on eNOS and iNOS. Taken together, COMP-Ang1 can promote wound healing in the diabetes through enhanced angiogenesis, lymphangiogenesis and blood flow.

The present invention is directed to a method of treating a variety of diseases for which angiogenesis could be the treatment modality. In one aspect, the invention is directed to treating an ischemic disease comprising administering to a person in need thereof an effective amount of a coiled coil chimeric molecule comprising a coiled-coil domain linked to a receptor binding domain of a ligand. In this method, the coiled coil domain may include a domain belonging to a protein belonging to matrix protein family, transcription factor family, growth factor family or secretory protein family. The coiled coil domain may be from cartilage matrix protein or cartilage oligomeric matrix protein, and further the receptor binding domain may bind to Tie1 or Tie2. Thus, the ligand may be a cytokine, hormone or growth factor such as an angiopoietin-related protein, including angiopoietin-related protein-1 (ARP1), angiopoietin-related protein-2 (ARP2), hepatic fibrinogen/angiopoietin-related protein (HFARP). The ligand may be angiopoietin-1, angiopoietin-2, angiopoietin-3 or angiopoietin-4, and in particular, angiopoietin-1. Most preferably, the chimeric coiled coil molecule is COMP-Ang1.

The ischemic disease may be, but is not limited to, a disease of the heart, limb, brain, penis, stomach or kidney.

It is also understood that the administration of the chimeric coiled coil molecule may be carried out by administering the protein form or by gene construct form, as popularly termed gene therapy for long lasting delivery of the chimeric coiled coil molecule. The gene delivery vehicle may be any method including liposomes, viruses, such as retrovirus or adnovirus or virus like particles, such as adeno-associated viruses.

In still another embodiment, the invention is directed to a method of healing wound comprising administering to a person in need thereof an effective amount of a coiled coil chimeric molecule comprising a coiled-coil domain linked to a receptor binding domain of a ligand. The wound may be cutaneous or internal to the body, or it may be a severe burn. Further, the wound may be caused on a person suffering from diabetes. The method of treatment using chimeric coiled coil molecule and protein and gene delivery are discussed above. The protein may be delivered internally through a solution or may be optionally delivered topically if cutaneous wound is being treated.

In yet another embodiment, the invention is directed to a method for treating vascular leakage comprising administering to a person in need thereof an effective amount of a coiled coil chimeric molecule comprising a coiled-coil domain linked to a receptor binding domain of a ligand. The vascular leakage may be due to sepsis, diabetic retinopathy, brain edema, excessive hemorrhagia, menorrhagia or nasal bleeding. The method of treatment using chimeric coiled coil molecule and protein and gene delivery are discussed above.

In another aspect, the invention is directed to a method for treating penile erectile dysfunction comprising administering to a person in need thereof an effective amount of a coiled coil chimeric molecule comprising a coiled-coil domain linked to a receptor binding domain of a ligand. The erectile dysfunction may be artherosclerotic or vascular diseased type. The method of treatment using chimeric coiled coil molecule and protein and gene delivery are discussed above.

In yet another aspect, the invention is directed to a method for treating myocardial infarction comprising administering to a person in need thereof an effective amount of a coiled coil chimeric molecule comprising a coiled-coil domain linked to a receptor binding domain of a ligand. The method of treatment using chimeric coiled coil molecule and protein and gene delivery are discussed above.

The invention further pertains to a method of treating implantation of cells, hair follicles, tissues and organs using the chimeric coiled coil molecule as discussed above.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIGS. 7A-7B show the effect of adenoviral COMP-Ang1 on skin color. Eight week-old male BALB/c-nu nude mice were treated with $1\times10^9$ pfu Ade-LacZ (Control, A) or Ade-COMP-Ang1 (B). Two weeks later, the skin color of the face, hands, and upper trunk were photographed. The mice treated with Ade-COMP-Ang1 show overt skin redness. Results from 3 experiments were similar.

FIGS. 24A-24D show that FVB/N mice were treated with $1\times10^9$ pfu Ade-COMP-Ang1 (n=6). At the indicated times, circulating plasma levels of COMP-Ang1 were measured by ELISA (A, black circle), and tracheal vessels were visualized with PECAM-1 immunostaining (B, red). The diameters of postcapillary venules (PV, brown curve) and terminal arterioles (TA, blue curve) are shown. Diameters of 35-40 PV/5 fields and 10-12 TA/10 fields were measured at the edge of cartilage rings in each mouse. Values are mean±SD from 4-5 mice. *, $P<0.05$ versus control period. Scale bar=50 μm. FIG. 24C shows Laser-Doppler flowmetric analyses for tracheal tissue blood flows of the mice treated with $1\times10^9$ pfu Ade-LacZ (Con) or $1\times10^9$ pfu Ade-COMP-Ang1 (CA1). Quantification of tracheal blood flows at 2 and 16 weeks after treatment with Con or CAL Bars represent mean±SD from 4-5 mice. *, $P<0.05$ versus Con. FIG. 24D indicate that FVB/N mice were pretreated with $1\times10^8$ (1+T2) or $5\times10^8$ (5+T2) pfu Ade-sTie2-Fc (each of n=5), or $5\times10^8$ pfu Ade-LacZ (LacZ, n=5) at 24 hr prior to $1\times10^8$ pfu Ade-COMP-Ang1 treatment. Two weeks later, tracheal vessels were visualized by PECAM-1 immunostaining (D, red). Scale bar=50 μm. Diameters of 35-40 PV/5 fields and 10-12 TA/10 fields were measured at the edge of cartilage rings in each mouse. FIG. 24E indicates that bars represent the mean±S.D. from 5 experiments as % inhibition of vascular remodeling induced by the pretreatment. Vascular remodeling induced by pretreatment of the Ade-LacZ is arbitrarily given as 100%. *, $P<0.05$ versus LacZ; $P<0.05$ versus 1+T2.

DETAILED DESCRIPTION OF THE INVENTION

Figure 1:
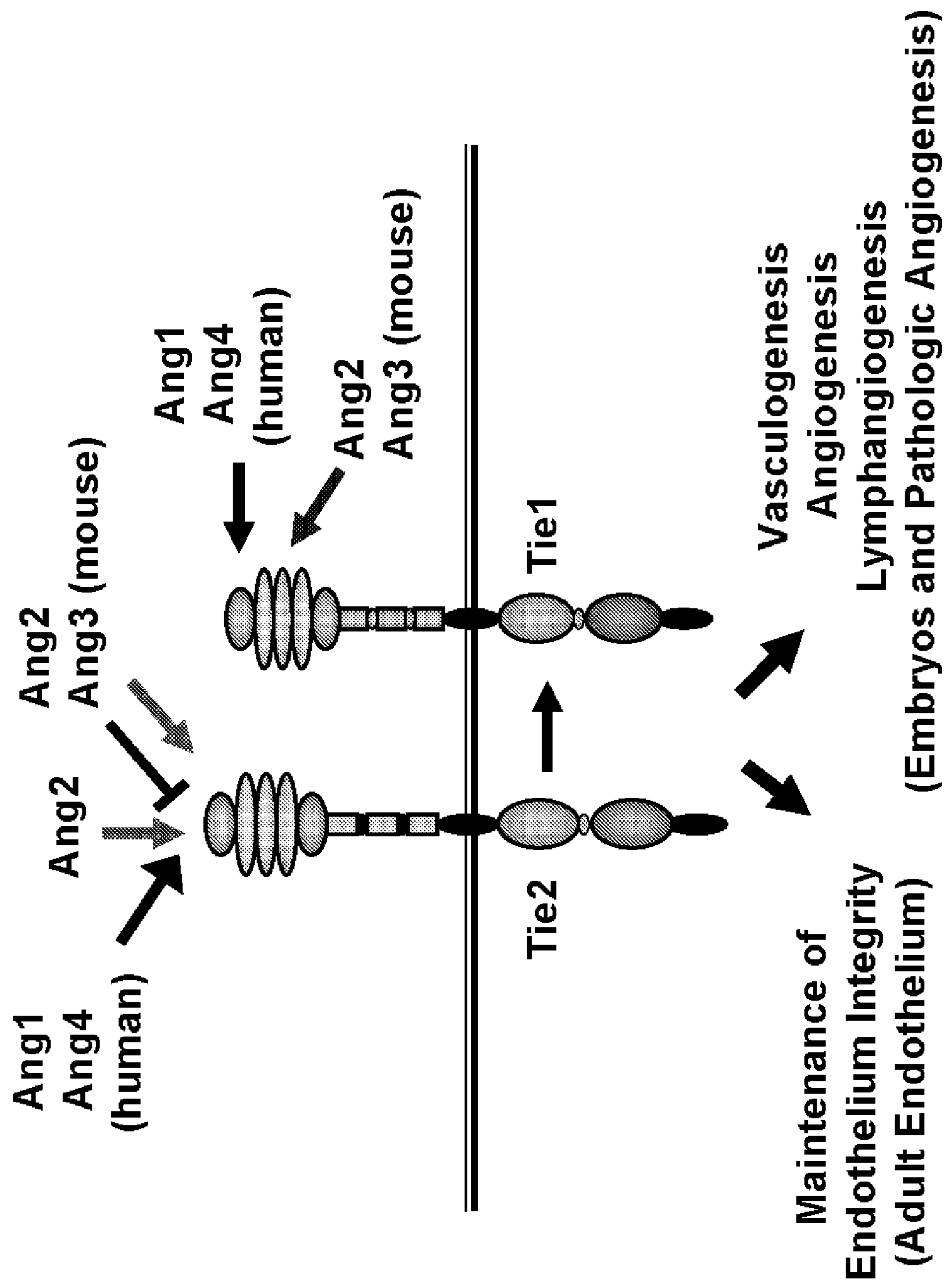
FIG. 1 shows the interaction between angiopoietins and Tie2. Angiopoietins bind to endothelial cell specific receptor kinase Tie2 and Tie1 and are known to regulate vasculogenesis, angiogenesis and lymphangiogeneis, and to maintain endothelial cell integrity. Among them, Ang1 and Ang3 act as agonists, Ang2 and Ang4 act as not only agonists but also act as antagonists in a context dependent manner.
Figure 2:
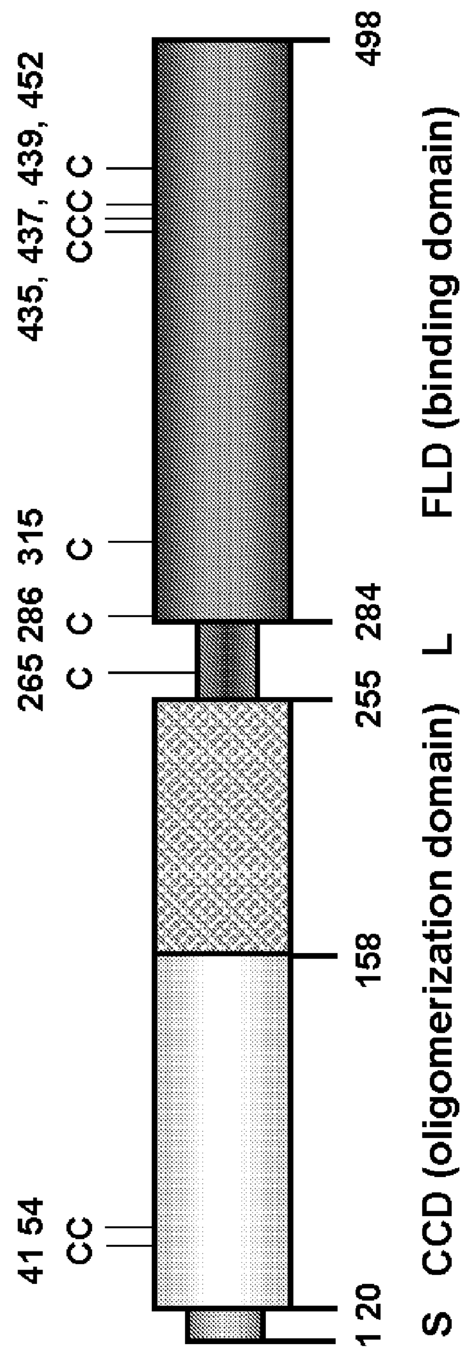
FIG. 2 shows a schematic diagram outlining the protein structure of native Ang1. Amino acids 1-19 are the secretory signal sequence (S), amino acids 20-158 are the superclustering domain (SCD), amino acids 158-255 are the coiled-coil oligomeric domain (CCOD), amino acids 226-283 are the linker (L), and amino acids 284-498 are the fibrinogen-like domain (FLD). There are cysteines (C) at amino acids 41, 54, 265, 315, 435, 437, 439, and 452.

In the present application, "a" and "an" are used to refer to both single and a plurality of objects.

As described in greater detail below, applicants have discovered a method of using coiled-coil domains for "multimerizing" ligands, which enhances the biological activity of such ligands that, absent such multimerization, would have lower levels of biological activity. This method may be used to multimerize receptor binding domains from any ligand that has improved affinity and/or increased activity (i.e. signaling ability) when they were multimerized as compared to the non-multimerized form of the ligand.

The present invention also provides for methods of using coiled-coil domains for "multimerizing" soluble receptors, which functions to make otherwise inactive soluble receptors biologically active, or which enhances the biological and binding activity of receptors that, absent such multimerization, would have lower levels of biological and binding activity. This method may be used to multimerize ligand binding domains using any receptor, which has improved affinity and/or increased activity (i.e. binding) when they were multimerized as compared to the native form of the soluble receptor.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "agonist" refers to a ligand that binds to a receptor, which activates the receptor and stimulates physiologic activity. For instance, Ang1 is considered to be an agonist of Tie2 receptor.

As used herein, "amino acid" and "amino acids" refer to all naturally occurring L-$\alpha$-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the $\alpha$-carboxy or $\alpha$-amino functional group of the amino acid.

Deletional variants are those with one or more amino acids in the native amino acid sequence removed. Ordinarily, deletional variants will have one or two amino acids deleted in a particular region of the molecule.

As used herein, "antagonist" refers to a ligand that tends to nullify the action of another ligand, as a ligand that binds to a cell receptor without eliciting a biological response.

As used herein, "biologically active" with regard to the ligand of the present invention refers to the ability of a molecule to specifically bind to and signal through a native receptor, e.g., a native Tie2 receptor, or to block the ability of a native Tie receptor (e.g., Tie2) to participate in signal transduction. Thus, the (native and variant) ligands of the present invention include agonists and antagonists of a native receptor, e.g. Tie2 receptor. Preferred biological activities of the ligands of the present invention include the ability to induce or inhibit vascularization. The ability to induce vascularization will be useful for the treatment of biological conditions and disease, where vascularization is desirable. On the other hand, the ability to inhibit or block vascularization may, for example, be useful in preventing or attenuating cell proliferation and tumor growth.

Preferred biological activities of the ligands of the present invention include the ability to inhibit vascular permeability. The ability to inhibit vascular permeability will be useful for treatment of medical conditions and diseases such as diabetic retinopathy, edema, and ascites. Preferred biological activities of the ligands of the present invention include the ability to maintain endothelial cell integrity (including preventing apoptosis). The ability to maintain endothelial cell integrity will be useful for treatment of medical conditions and diseases such as mannitol treatment, irradiation, and sepsis.

The biological activity of the chimeric receptor, which may be in soluble form, includes its ability to inhibit or competitively inhibit the ligand's activity by binding to its ligand. Thus, in this way, cell proliferation may be inhibited if the ligand is an agonist for cell proliferation. Alternatively, administration of chimeric receptor may act as an enhancer of cell proliferation if the ligand is an antagonist for cell proliferation.

It is also contemplated that chimeric ligand and chimeric receptor be labeled with a detectable label, such as radioisotope, fluorescent tag, enzymatic tag, or a chemiluminescent tag to determine ligand-receptor binding interaction. As such, assay systems employing the chimeric molecule is also contemplated.

As used herein, "carriers" include pharmaceutically acceptable carriers, excipients, or stabilizers which are nontoxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "chimeric coiled coil molecule" and "coiled coil chimeric molecule" are used interchangeably.

As used herein, "chimeric ligand", "chimeric receptor", "chimeric polypeptide" or "chimeric molecule" refers to the combination of coiled coil domain and a receptor binding domain or a ligand binding domain. The resultant chimeric polypeptide is capable of forming biologically active multimers, which are soluble. The coiled coil domain may be derived from any source, including any animal or mammalian protein, and in particular any human protein, and further includes those that are synthetically made. Moreover, the coiled coil domain and the ligand or receptor constructs may be from the same or different source. It is understood that the chimeric construct comprises the coiled coil domain and a receptor binding domain of a ligand or a ligand binding domain of a receptor, and further may include other components that may be included so long their inclusion does not interfere with the formation of a biologically active multimer that has improved solubility, ease of recombinant production of the chimeric polypeptide and substantially similar or greater potency as the native ligand or native soluble receptor. For example, FLAG sequence may be included for ease of purification, provided its inclusion does not interfere with the function of the chimeric molecule. The FLAG sequence also may be removed if a humanized construct is desired.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state.

As used herein, "fragments" or "functional derivatives" refers to biologically active amino acid sequence variants and fragments of the native ligands or receptors of the present invention, as well as covalent modifications, including derivatives obtained by reaction with organic derivatizing agents, post-translational modifications, derivatives with nonproteinaceous polymers, and immunoadhesins.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change.

As used herein, "ligand" refers to any molecule or agent, or compound that specifically binds covalently or transiently to a molecule such as a polypeptide. When used in certain context, ligand may include antibody. In other context, "ligand" may refer to a molecule sought to be bound by another molecule with high affinity, such as in a ligand trap.

As used herein, "ligand binding domain" refers to the portion of the receptor that binds to the ligand and includes the minimal portion of the receptor that is necessary to bind its ligand.

As used herein, "linked" refers to direct or indirect connection between the multimerizing domain and the ligand or receptor. Both a direct fusion between these two domains or indirect fusion as by the domains being separated by a linker or an intervening domain or element are contemplated, so long as the activity of the chimeric fusion is present.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "multimer" or "multimeric" refers to the joining of the multimerizing agent such as the coiled coil domain to each other to form a dimer, trimer, tetramer, pentamer, hexamer, heptamer, octamer, nanomer, decamer and so on, which may be in a parallel or anti-parallel form, through intramolecular or intermolecular bonds.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 μg to about 2000 mg. Expressed in proportions, the active compound is generally present in from about 0.5 μg/ml of carrier. In the case of compositions containing supplementary active ingredients, the dosages are determined by reference to the usual dose and manner of administration of the said ingredients.

As used herein, "receptor binding domain" refers to the portion of the ligand that binds to the receptor and includes the minimal portion of the ligand that is necessary to bind its receptor. The present invention is based on the discovery that a multimerizing agent, such as a coiled coil domain, which was previously perceived as a source of hindrance for isolating recombinant proteins containing them, has been found to provide advantageous features of easy recombinant protein expression and purification, greater solubility and greater or substantially equal potency compared with the native protein containing the coiled coil domain.

As used herein, "sample" or "biological sample" is referred to in its broadest sense, and includes any biological sample obtained from an individual, body fluid, cell line, tissue culture, or other source which may contain a chimeric Ang1 binding factor, depending on the type of assay that is to be performed. As indicated, biological samples include body fluids, such as semen, lymph, sera, plasma, urine, synovial fluid, spinal fluid and so on. Methods for obtaining tissue biopsies and body fluids from mammals are well known in the art.

As used herein, the term "specifically binds" refers to a non-random binding reaction between two molecules, for example between an antibody molecule immunoreacting with an antigen, or a non-antibody ligand reacting with another polypeptide, such as chimeric Ang1 specifically binding with Tie2.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

The present invention includes a multimer forming domain. In particular, coiled coil domain is exemplified. The coiled coil domain may be any amino acid sequence that forms a coiled coil structure. While the exemplified coiled coil domains herein are those cloned from a variety of proteins, it is understood that various mutations and derivatization are encompassed by the invention, so long as the resultant coiled coil domain is recognized by a person of skill in the art as a coiled coil structure and the coiled coil domain containing chimera is capable of forming a multimer, is easily soluble, and is able to provide similar or greater potency with respect to the native ligand or receptor.

As used herein, "wound" refers to damaged conditions of living bodies and encompasses cut or disrupted pathological conditions of tissues constituting the internal and external surface of the living body, for example skin, muscle, nervous tissue, bone, soft tissue, inner organs and vascular tissue. Exemplary wounds include, but are not limited to, contusion or bruise, non-healing traumatic wounds, tissue disruption by irradiation, abrasion, gangrene, laceration, avulsion, penetrated wound, gun shot wound, cutting, burn, frostbite, cutaneous ulcers, xeroderma, skin keratosis, breakage, rupture, dermatitis, dermatophytosis, surgical wounds, wounds caused by vascular disorders, corneal wounds, sores such as pressure sore and bed sore, diabetes and poor circulation-associated conditions diabetic skin erosion, chronic ulcers, suture site following plastic surgery, spinal traumatic wounds, gynecological wounds, chemical wounds and acne. Any damaged or injured part of the living body is within the definition of the wounds. In this respect, the composition comprising the chimeric coiled coil molecule according to the present invention can be useful for the repair, replacement, alleviation, acceleration, promotion, healing and/or curing of any damaged or injured tissue.

It is further understood that in certain situations, in linking together the multimerizing domain with either the receptor binding domain of the ligand or ligand binding domain of the receptor, the multimerizing domain and the binding domain may be from the same protein, or they may be from different proteins. For instance, Ang1 coiled coil domain may be linked to its own fibrinogen-like domain in a more efficient manner. Or, a cartilage oligomeric matrix protein (COMP) could be linked to the Ang1 fibrinogen-like domain.

Chimeric Ang1

When mention is made of the chimeric constructs GCN-Ang1, MAT-Ang1, or COMP-Ang1, it is understood that the Ang1 portion referred to is the fibrinogen domain of Ang1. In addition, MAT-Ang1 is also sometimes referred to as CMP-Ang1, CMP-Ang1/FD, or CMP/CC-Ang1/FD in the figures.

Applicant has discovered that a chimeric form of Ang1, COMP-Ang1, has many potential advantages over the native protein. The generation of native Ang1 is difficult, and the activities of the purified proteins vary, possibly due to its tendency to form multimers. Our structural analysis of native Ang1 by rotary shadowing TEM indicates that native Ang1 exists as variably-sized multimers. Though we originally intended to generate trimeric and pentameric Ang1 using short coiled-coil domains of matrix proteins, interestingly, MAT-Ang1 and COMP-Ang1 yielded additional oligomers. Nevertheless, MAT-Ang1 and COMP-Ang1 are easier to purify and more soluble than native Ang1. Notably, COMP-Ang1 is approximately 3-5 times more potent than native Ang1. Without being limited by theory, there may be two possible reasons why COMP-Ang1 produced the most potent effect on Tie2 and Akt phosphorylation. First, COMP-Ang1 could be the most biologically active among the variants because of its rapid association and dissociation rate. Second, COMP-Ang1 may induce Tie2 clustering in endothelial caveolae more efficiently than the other recombinant Ang1 proteins. Our data indicate that Tie2 molecules are localized in endothelial caveolae. Thus, an engineered Ang1 protein with an oligomeric structure better suited to clustering Tie2 in caveolae may better facilitate Tie2 multimerization and phosphorylation.

In a mouse corneal micropocket assay, Ang1 failed to stimulate an angiogenic response when administered alone. However, when co-administered with VEGF, Ang1 augmented postnatal angiogenesis. We have shown that native Ang1 failed to stimulate an angiogenic response. However, COMP-Ang1 alone stimulates angiogenesis. Furthermore, COMP-Ang1 produced an increase in the luminal diameter of the basal limbus. This role is consistent with increased frequency of enlarged vessel diameters in Ang1-overexpressing transgenic mice (Suri, C. et al., 1998, Science 282: 468-471; Thurston, G. et al., 1999, Science 286:2511-2514). In a rabbit ischemic hindlimb model, we previously showed that Ang1 gene delivery resulted in larger blood vessels compared to VEGF gene delivery (Chae, J. K. et al., 2000, Arterioscler.

Thromb. Vasc. Biol. 20:2573-2578). Thus, COMP-Ang1 can produce more effective blood flow by increasing the diameter of arterial lumens. In addition, Ang1 can counteract VEGF-induced side effects such as edema and inflammation, while having an additive effect on angiogenesis (Kwak, H. J. et al., 2000, Circulation 101:2317-2324; Thurston, G. et al., 1999, Science 286:2511-2514; Kim, I. et al., 2001, Circ. Res. 89:477-479). Thus, COMP-Ang1 protein delivery may be useful for accurate and safe therapeutic angiogenesis.

Integrity of the vascular endothelium in response to physical, biochemical, and immune-mediated damage is important to maintaining endothelial function and preventing vascular diseases (Cines, D. B. et al., 1998, Blood 91:3527-3561). According to a recent report, extensive apoptosis of microvascular endothelial cells of the lamina propria is the primary lesion initiating intestinal radiation damage (Paris, F. et al., 2001, Science 293:293-297). Thus, GI tract damage during abdominal radiotherapy limits the dose that can be used during cancer treatment. Radiation damage to vascular endothelial cells can be prevented by VEGF (Okunieff, P. et al., 1998, Radiat. Res. 150:204-211) or basic fibroblast growth factor (bFGF) (Paris, F. et al., 2001, Science 293:293-297). Importantly, VEGF receptors are expressed in endothelial cells that are actively involved in vasculogenesis and angiogenesis such as tumor progression, whereas bFGF receptors are expressed in both endothelial and non-endothelial cells including cancer cells (Paris, F. et al., 2001, Science 293:293-29; Veikkola, T. & Alitalo, K. 1999, Seminars in Cancer Biol. 9:211-220). Therefore, administration of VEGF and bFGF for protection of endothelial damage may help tumor progression. Interestingly, Tie2 is selectively expressed in active form in the endothelial cells of normal adult vessels (Wong, A. L. et al., 1997, Circ. Res. 81:567-574). We recently reported that the angiopoietin/Tie2 system in normal adult blood vessels may be important in maintaining the integrity of non-proliferating endothelial cells (Kim, I. et al., 2001, Cardiovas. Res. 49:872-881). Our immunohistochemical staining indicates that Tie2 is selectively expressed in most endothelial cells of normal adult vessels and capillaries. Moreover, Tie2 is effectively activated by acute administration of COMP-Ang1. One concern is that repeated administration of Ang1 may increase tumor angiogenesis during radiation therapy. However, the role of Ang1 in tumor angiogenesis is still controversial. It has even been suggested that Ang1 may suppress tumor progression through 'stabilization' of tumor vessels (Tian, S. et al., 2002, Br. J. Cancer 286:645-651; Hawighorst, T. et al., 2002, Am. J. Pathol. 160:1381-1392). Therefore, using Ang1 for protection against radiation-induced endothelial cell damage could be ideal. Indeed, COMP-Ang1 treatment strongly protects against extensive radiation-induced extensive endothelial apoptosis in villi, but has no observed effect on non-endothelial cells (Cho et al., PNAS 101:5553-5558). In addition, COMP-Ang1 treatment prolongs survival periods, perhaps as a result of decreasing damage to the GI tract (Cho et al., PNAS 101:5553-5558). Optimizing the dosage and route of administration of COMP-Ang1 could further improve endothelial cell survival following radiation-induced endothelial cell damage.

COMP-Ang1 is superior to native Ang1 in several ways including efficiency of generation, potency, Tie2 activation in vivo, angiogenesis, and protection against endothelial injury in vivo (Cho et al., PNAS 101:5547-5552, 2004; Cho et al., PNAS 101:5553-5558, 2004; U.S. patent application Ser. No. 10/273,180 and PCT/IB03/03814). It seems likely that it can be further applied to the prevention of vascular leakage, protection against sepsis-induced endothelial cell injury, enhancement of re-endothelialization after angioplasty, and in vitro amplification of Tie2 positive endothelial precursor stem cells. In conclusion, we designed and generated a soluble, non-aggregating, potent, and stable chimeric Ang1 variant, COMP-Ang1 (Cho et al., PNAS 101:5547-5552, 2004; Cho et al., PNAS 101:5553-5558, 2004; U.S. patent application Ser. No. 10/273,180 and PCT/IB03/03814). It may be useful for clinical therapies including therapeutic angiogenesis and endothelial cell protection.

Coiled Coil

The α-helical coiled coil is probably the most widespread subunit oligomerization motif found in proteins. Accordingly, coiled coils fulfill a variety of different functions. In several families of transcriptional activators, for example, short leucine zippers play an important role in positioning the DNA-binding regions on the DNA (Ellenberger et al., 1992, Cell 71:1223-1237). Coiled coils are also used to form oligomers of intermediate filament proteins. Coiled-coil proteins furthermore appear to play an important role in both vesicle and viral membrane fusion (Skehel and Wiley, 1998, Cell 95:871-874). In both cases hydrophobic sequences, embedded in the membranes to be fused, are located at the same end of the rod-shaped complex composed of a bundle of long α-helices. This molecular arrangement is believed to cause close membrane apposition as the complexes are assembled for membrane fusion.

The coiled coil is often used to control oligomerization. It is found in many types of proteins, including transcription factors such as, but not limited to GCN4, viral fusion peptides, SNARE complexes and certain tRNA synthetases, among others. Very long coiled coils are found in proteins such as tropomyosin, intermediate filaments and spindle-pole-body components.

Coiled coils involve a number of α-helices that are supercoiled around each other in a highly organized manner that associate in a parallel or an antiparallel orientation. Although dimers and trimers are the most common. The helices may be from the same or from different proteins.

The coiled-coil is formed by component helices coming together to bury their hydrophobic seams. As the hydrophobic seams twist around each helix, so the helices also twist to coil around each other, burying the hydrophobic seams and forming a supercoil. It is the characteristic interdigitation of side chains between neighbouring helices, known as knobs-into-holes packing, that defines the structure as a coiled coil. The helices do not have to run in the same direction for this type of interaction to occur, although parallel conformation is more common. Antiparallel conformation is very rare in trimers and unknown in pentamers, but more common in intramolecular dimers, where the two helices are often connected by a short loop.

In the extracellular space, the heterotrimeric coiled-coil protein laminin plays an important role in the formation of basement membranes. Other examples are the thrombospondins and cartilage oligomeric matrix protein (COMP) in which three (thrombospondins 1 and 2) or five (thrombospondins 3, 4 and COMP) chains are connected. The molecules have a flower bouquet-like appearance, and the reason for their oligomeric structure is probably the multivalent interaction of the C-terminal domains with cellular receptors.

GCN4

The yeast transcriptional activator GCN4 is 1 of over 30 identified eukaryotic proteins containing the basic region leucine zipper (bZIP) DNA-binding motif (Ellenberger et al., 1992, Cell 71:1223-1237). The bZIP dimer is a pair of continuous alpha helices that form a parallel coiled-coil over their carboxy-terminal 34 residues and gradually diverge toward their amino termini to pass through the major groove of the DNA binding site. The coiled-coil dimerization interface is oriented almost perpendicular to the DNA axis, giving the complex the appearance of the letter T. bZIP contains a 4-3 heptad repeat of hydrophobic and nonpolar residues that pack together in a parallel alpha-helical coiled-coil (Ellenberger et al., 1992, Cell 71:1223-1237). The stability of the dimer results from the side-by-side packing of leucines and nonpolar residues in positions a and d of the heptad repeat, as well as a limited number of intra- and interhelical salt bridges, shown in a crystal structure of the GCN4 leucine zipper peptide (Ellenberger et al., 1992, Cell 71:1223-1237).

Cartilage Matrix Protein (CMP or MAT)

CMP (matrilin-1) was isolated from bovine tracheal cartilage as a homotrimer of subunits of $M_r$ 52,000 (Paulsson and Heinegård, 1981, Biochem J. 197:367-375), where each subunit consists of a vWFA1 module, a single EGF domain, a vWFA2 module and a coiled coil domain spanning five heptads (Kiss et al., 1989, J. Biol. Chem. 264:8126-8134; Hauser and Paulsson, 1994, J. Biol. Chem. 269:25747-25753). Electron microscopy of purified CMP showed a bouquet-like trimer structure in which each subunit forms an ellipsoid emerging from a common point corresponding to the coiled coil (Hauser and Paulsson, 1994, J. Biol. Chem. 269:25747-25753). The coiled coil domain in matrilin-1 has been extensively studied. The trimeric structure is retained after complete reduction of interchain disulfide bonds under non-denaturing conditions (Hauser and Paulsson, 1994, J. Biol. Chem. 269:25747-25753).

Cartilage Oligomeric Matrix Protein (COMP)

A non-collagenous glycoprotein, COMP, was first identified in cartilage (Hedbom et al., 1992, J. Biol. Chem. 267:6132-6136). The protein is a 524 kDa homopentamer of five subunits which consists of an N-terminal heptad repeat region (cc) followed by four epidermal growth factor (EGF)-like domains (EF), seven calcium-binding domains (T3) and a C-terminal globular domain (TC). According to this domain organization, COMP belongs to the family of thrombospondins. Heptad repeats $(abcdefg)_n$ with preferentially hydrophobic residues at positions a and d form-helical coiled-coil domains (Cohen and Parry, 1994, Science 263:488-489). Recently, the recombinant five-stranded coiled-coil domain of COMP (COMPcc) was crystallized and its structure was solved at 0.2 nm resolution (Malashkevich et al., 1996, Science 274:761-765).

Nucleic Acid Constructs

The present invention also provides for a nucleic acid encoding a fusion polypeptide wherein the fusion polypeptide comprises a first subunit comprising at least one copy of the receptor binding domain of a ligand, the first subunit being fused to the C-terminal end of a multimerizing component.

Alternatively, the present invention provides for a nucleic acid encoding a fusion polypeptide wherein the fusion polypeptide comprises a first subunit comprising at least one copy of the receptor binding domain of a ligand, the first subunit being fused to the N-terminal end of a multimerizing component. In particular, the multimerizing component may be the coiled coil domain.

The present invention also provides for a nucleic acid encoding a fusion polypeptide wherein the fusion polypeptide comprises a first subunit comprising at least one copy of the ligand binding domain of a receptor, the first subunit being fused to the C-terminal end of a multimerizing component.

Alternatively, the present invention provides for a nucleic acid encoding a fusion polypeptide wherein the fusion polypeptide comprises a first subunit comprising at least one copy of the ligand binding domain of a receptor, the first subunit being fused to the N-terminal end of a multimerizing component. In particular, the multimerizing component may be the coiled coil domain.

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS or CHO cell.

The present invention also provides for methods of producing the fusion polypeptides of the invention by growing cells of the host-vector system described herein, under conditions permitting production of the fusion polypeptide and recovering the fusion polypeptide so produced. The fusion polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The fusion polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, fusion polypeptide includes functionally equivalent molecules in which amino acid residues are substituted for residues within the sequence resulting in a silent or conservative change. For example, one or more amino acid residues within the sequence can be substituted by another amino acid of a similar polarity which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express the fusion polypeptides of the invention are genetically engineered to produce them by, for example, transfection, transduction, electropration, or microinjection techniques.

In addition, the present invention contemplates use of the fusion polypeptides described herein in tagged form.

Any of the methods known to one skilled in the art for the insertion of DNA fragments into a vector may be used to construct expression vectors encoding the fusion polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the fusion polypeptides of the invention may be regulated by a second nucleic acid sequence so that the fusion polypeptide is expressed in a host transformed with the recombinant DNA molecule. For example, expression of the fusion polypeptides described herein may be controlled by any promoter/enhancer element known in the art. Promoters which may be used to control expression of the fusion polypeptide include, but are not limited to the long terminal repeat as described in Squinto et al., (1991, Cell 65:1-20); the SV40 early promoter region (Bernoist and Chambon, 1981, Nature 290:304-310), the CMV promoter, the M-MuLV 5' terminal repeat the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:144-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a fusion polypeptide as described herein, and in particular modified angiopoietin, are used to transfect the host and thereby direct expression of such nucleic acid to produce fusion polypeptides which may then be recovered in biologically active form. As used herein, a biologically active form includes a form capable of binding to the relevant receptor and causing a differentiated function and/or influencing the phenotype of the cell expressing the receptor. Such biologically active forms would, for example, induce phosphorylation of the tyrosine kinase domain of Tie2 receptor, or stimulation of synthesis of cellular DNA.

Expression vectors containing the nucleic acid inserts can be identified by without limitation, at least three general approaches: (a) DNA-DNA hybridization, (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The fusion polypeptide, in particular modified angiopoietin of the present invention, may be expressed in the host cells transiently, constitutively or permanently. In other aspects, a construct that expresses soluble Tie1 or Tie2 may be made. The soluble Tie2 is exemplified in the present application as Ade-sTie2-Fc, which uses Adenovirus as the carrier virus, although it is understood that the construct is not limited to an Adenovirus, and any vector may be used in the practice of the invention. The Ade-sTie2-Fc construct is used to exemplify a control construct in the present application.

The invention herein further provides for the development of a fusion polypeptide as a therapeutic agent for the treatment of patients suffering from disorders involving cells, tissues or organs which express the Tie2 receptor. Such molecules may be used in a method of treatment of the human or animal body, or in a method of diagnosis.

Because Tie2 receptor has been identified in association with endothelial cells and, blocking of agonists of the receptor such as Ang-1 has been shown to prevent vascularization, applicants expect that Tie2 agonist fusion polypeptides of the invention may be useful for the induction of vascularization in diseases or disorders where such vascularization is indicated. Such diseases or disorders would include wound healing, ischemia and diabetes. The ligands may be tested in animal models and used therapeutically as described for other agents, such as vascular endothelial growth factor (VEGF), which is another endothelial cell-specific angiogenic factor.

U.S. Pat. No. 5,332,671, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired. See also European Patent Application 0 550 296 A2; Banai, et al., Circulation 89:2183-2189 (1994); Unger, et al. Am. J. Physiol. 266:H1588-H1595 (1994); and Lazarous, et al. Circulation 91:145-153 (1995). According to the invention, the agonist fusion polypeptides may be used alone or in combination with one or more additional pharmaceutically active compounds such as, for example, VEGF or basic fibroblast growth factor (bFGF).

Conversely, antagonists of the Tie2 receptor, such as Tie2 receptor bodies or Ang-2 as described in Example 9 in WO 96/31598, have been shown to prevent or attenuate vascularization in certain situations and in certain amounts. Similarly, Tie2 antagonist fusion polypeptides of the invention would also be useful for those purposes. These antagonists may be used alone or in combination with other compositions, such as anti-VEGF antibodies, that have been shown to be useful in treating conditions in which the therapeutic intent is to block angiogenesis.

In other embodiments, the Tie2 agonist fusion polypeptides of the invention described herein may be used as hematopoietic factors. A variety of hematopoietic factors and their receptors are involved in the proliferation and/or differentiation and/or migration of the various cells types contained within blood. Because Tie2 receptors are expressed in early hematopoietic cells, the Tie2 ligands are expected to play a comparable role in the proliferation or differentiation or migration of these cells. Thus, for example, Tie2 agonist fusion polypeptide compositions may be prepared, assayed, examined in in vitro and in vivo biological systems and used therapeutically as described in any of the following: U.S. Pat. No. 4,810,643; Lee, et al., Proc. Natl. Acad. Sci. USA 82:4360-4364 (1985); Wong, et al., Science, 228:810-814 (1985); Yokota, et al., Proc. Natl. Acad. Sci. (USA) 81:1070 (1984); WO 9105795; and WO 95/19985.

Accordingly, the fusion polypeptides may be used to diagnose or treat conditions in which normal hematopoiesis is suppressed, including, but not limited to anemia, thrombocytopenia, leukopenia and granulocytopenia. In a preferred embodiment, the fusion polypeptides may be used to stimulate differentiation of blood cell precursors in situations where a patient has a disease, such as acquired immune deficiency syndrome (AIDS), which is associated with reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The fusion polypeptides of the present invention may be used alone, or in combination with other pharmaceutically active agents such as, for example, cytokines, neurotrophins, interleukins, etc. In a preferred embodiment, the fusion polypeptides may be used in conjunction with any of a number of factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF and so on.

In an alternative embodiment, Tie2 receptor antagonist fusion polypeptides are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the fusion polypeptides as described herein.

Effective doses useful for treating these or other diseases or disorders may be determined using methods known to one skilled in the art (see, for example, Fingl, et al., The Pharmacological Basis of Therapeutics, Goodman and Gilman, eds. Macmillan Publishing Co, New York, pp. 1-46 (1975). Pharmaceutical compositions for use according to the invention include the fusion polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a fusion polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the fusion polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

Gene Therapy

In a specific embodiment, nucleic acids comprising sequences encoding the chimeric Ang1 polypeptide are administered to prevent vascular leakage, and for therapeutic vasculogenesis, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode a chimeric-Ang1 or Tie2 polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

In one embodiment, the present invention relates to treatment for various diseases that are characterized by being treatable through therapeutic angiogenesis such as but not limited to vascular leakage or lack of blood vessel formation. In this way, the inventive therapeutic compound may be administered to human patients who are either suffering from, or prone to suffer from the disease by providing compounds that activate Tie2.

The formulation of therapeutic compounds is generally known in the art and reference can conveniently be made to Remington's Pharmaceutical Sciences, 17th ed., Mack Publishing Co., Easton, Pa., USA. For example, from about 0.05 μg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

Topical Application to Wounds

According to the present invention, the chimeric coiled coil molecule in the form of liquid or powder can be applied directly onto the wound, i.e., sprinkled over the wound site. The chimeric coiled coil molecule applied to a sheet may be applied over the wound site, which is then dressed suitably to protect the wound and prevent the healing effects of the active ingredient from diminishing. Any commercially available or conventional wound dressing may be used in the present invention. The examples of commercially available wound dressings include, but are not limited to, COMPEEL®, DUODERM™, TAGADERM™ and OPSITE®.

The composition containing a pharmaceutically effective amount of the chimeric coiled coil molecule in combination with a pharmaceutically acceptable carrier can be formulated into a variety of forms by means known in the pharmaceutical art. The administration forms include, but are not limited to, conventional dosage forms of external preparation, e.g., liquid paints, sprays, lotions, creams, gels, pastes, liniments, ointments, aerosols, powders and transdermal absorbers. Actual methods for preparing administrable compositions will be known or apparent to those skilled in the art and are described in more detail in such publications as Remington's Pharmaceutical Science, 15$^{th}$ Edition, 1975, Mack Publishing Company, Easton, Pa. 18042 (Chapter 87: Blaug, Seymour), the contents of which are incorporated herein by reference.

In the external preparation of the present invention, suitable carriers can be chosen depending on the dosage forms and include, but are not limited to, hydrocarbons such as vaseline, liquid paraffin, and plasticized hydrocarbon gel (plastibase); animal and vegetable oils such as medium-chain fatty acid triglyceride, lard, hard fat, and cacao oil; higher fatty acid and alcohols and esters thereof such as stearic acid, cetanol, stearyl alcohol, and palmitic acid isopropyl; water-soluble bases such as Macrogol (polyethylene glycol), 1,3-butylene glycol, glycerol, gelatine, white sugar, and sugar alcohol; emulsifiers such as glycerine fatty acid ester, stearic acid polyoxyl, and polyoxyethylene/or curing castor oils; thickeners such as acrylic acid esters, and sodium alginates; propellants such as liquefied petroleum gas, and carbon dioxide; and preservatives such as paraoxybenzoic acid esters. The external preparation of the present invention can be prepared with the aforementioned carriers by methods well-known to those skilled in the art. In addition to said carriers, additives such as stabilizers, pigments, coloring agents, pH adjusting agents, diluents, surfactants, and antioxidants are, if necessary, used. The external preparation of the present invention can be applied to the tropical wound site by conventional methods.

The external preparation according to the present invention may be also used in adhesion onto a solid support such as a wound covering release layer. The adhesion is achieved by saturation of the solid support with a composition containing the chimeric coiled coil molecule. In one embodiment of the present invention, the solid support is first coated with an adhesion layer to improve the adhesion of the chimeric coiled coil molecule to the solid support. Exemplary adhesion materials include polyacrylate and cyanoacrylate. As such formulation, there is provided a number of commercially available products, including bandage having non-adhesive wound-covering release layer in a perforated plastic film by Smith & Nephew Ltd., BAND-AID® in thin strip, patch, spot and thermoplastic strip forms by Johnson & Johnson, CURITY® and CURAD® ("ouchless" type of bandage) by Kendall Co. (a division of Colgate-Palmolive Company), and STIK-TITE® (elastic strip) by American White Cross Labs, Inc.

In one embodiment, the pharmaceutical composition according to the present invention can be formulated into a liquid paint preparation by mixing the chimeric coiled coil molecule with physiologic saline at a fixed ratio by volume and adjusting the pH value of the resulting mixture to the range of from 3.5 to 6.5. In another embodiment, the pharmaceutical composition according to the present invention can be formulated into an ointment preparation by mixing the chimeric coiled coil molecule with a water-soluble ointment base and adding physiologic saline to the resulting mixture. Preferably, the pH value of the ointment is adjusted to the range of from 3.5 to 6.5.

According to the present invention, pharmaceutical carriers such as gels or microspheres may be used to promote the wound healing. A variety of microsheres of a polymer as carriers for one or more pharmaceutically or cosmetically active substances is described in U.S. Pat. No. 5,264,207, WO 2000/24378, WO96/13164 and WO 94/13333, the entire contents of which are incorporated herein by reference The pharmaceutical composition of the present invention can be used to treat a variety of wounds in mammalian animals. Especially, the composition of the present invention is effective for the treatment of non-healing ulcers, including those due to infection, malignancy, large vessel arterial insufficiency, small vessel arterial insufficiency, deep venous blockage or insufficiency, superficial venous insufficiency (varicose veins), lymphatic obstruction, intrinsic circulatory insufficiency, hematologic abnormalities, collagen vascular disorders, radiation dermatitis, trophic causes and the like.

The pharmaceutically effective amount of the chimeric coiled coil molecule refers to an amount which acts on various cell-activating substances and abnormal cells around the wound site and promotes the wound healing. As one of skill in the art will appreciate, the amount may vary depending on the wound type being treated, the wound site to be treated, the frequency and time of administration, the route and form of administration, the severity of the wound being treated, the kinds of vehicles, and other factors.

Generally, 2 to 5% by weight of the chimeric coiled coil molecule are administered per dose. The frequency of administration may range between twice daily and once per week. In a specific embodiment, full thickness defect wounds are treated with from 0.01 to 0.1 g/cm$^2$ of the pharmaceutical composition of the present invention daily, preferably from 0.02 to 0.09 g/cm$^2$, more preferably from 0.02 to 0.07 g/cm$^2$.

Labels

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Further suitable labels for the chimeric-Ang1, Tie2 or chimeric Ang1/Tie2 complex-specific antibodies of the present invention are provided below. Examples of suitable enzyme labels include malate dehydrogenase, δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is preferred isotope where in vivo imaging is used since its avoids the problem of dehalogenation of the $^{125}$I or $^{131}$I-labeled polypeptide by the liver. In addition, this radionucleotide has a more favorable gamma emission energy for imaging. For example, $^{111}$In coupled to monoclonal antibodies with 1-(P-isothiocyanatobenzyl)-DPTA has shown little uptake in non-tumors tissues, particularly the liver, and therefore enhances specificity of tumor localization.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, *Pseudomonas* toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron. Deuterium may also be used. Other contrasting agents also exist for EPR, PET or other imaging mechanisms, which are known to persons of skill in the art.

Typical techniques for binding the above-described labels to polypeptides are provided by Kennedy et al. (1976) Clin. Chim. Acta 70:1-31, and Schurs et al. (1977) Clin. Chim. Acta 81:1-40. Coupling techniques include the glutaraldehyde method, the periodate method, the dimaleimide method, the m-maleimidobenzoyl-N-hydroxy-succinimide ester method, all of which methods are incorporated by reference herein.

The polypeptides and antibodies of the present invention, including fragments thereof, may be used to detect chimeric-Ang1, Tie2 or chimeric Ang1/Tie2 complex using biochip and biosensor technology. Biochip and biosensors of the present invention may comprise the polypeptides of the present invention to detect antibodies, which specifically recognize chimeric Ang1/Tie2 complex. Bio chip and biosensors of the present invention may also comprise antibodies which specifically recognize the polypeptides of the present invention to detect chimeric Ang1/Tie2 complex.

Systemic Effects of COMP-Ang1

In order to examine systemic effect of COMP-Ang1, the stable Chinese hamster ovary (CHO) cell line producing COMP-Ang1 (CA1-2; production rate, ~30 mg/L) was made and adenoviral vector encoding COMP-Ang1 was made according to standard methods.

In order to determine systemic effect of COMP-Ang1, we administered 200 μg of COMP-Ang1/mouse/day for 2-3 weeks or adenoviral COMP-Ang1 ($1\times10^{9}$ pfu) singly through tail vein in adult mice (8-12 weeks old). As a control, we administered 200 μg of bovine serum albumin (BSA)/mouse/day for 2-3 weeks or adenoviral-LacZ ($1\times10^{9}$ pfu) singly through tail vein into age- and sex-matched adult mice (8-12 weeks old).

Therapeutic Angiogenesis

After 2-3 weeks after treatment of COMP-Ang1 recombinant protein, the mice showed redness in the face, hand, soles, gland penis and tails, where skins have no hair with 100% frequency, while control mice showed normal skin color. The mice received Ade-COMP-Ang1 displayed persistent skin redness up to 12 months so far we examined (FIGS. 25A, 25B, 25C, and 25D).

Figure 3:
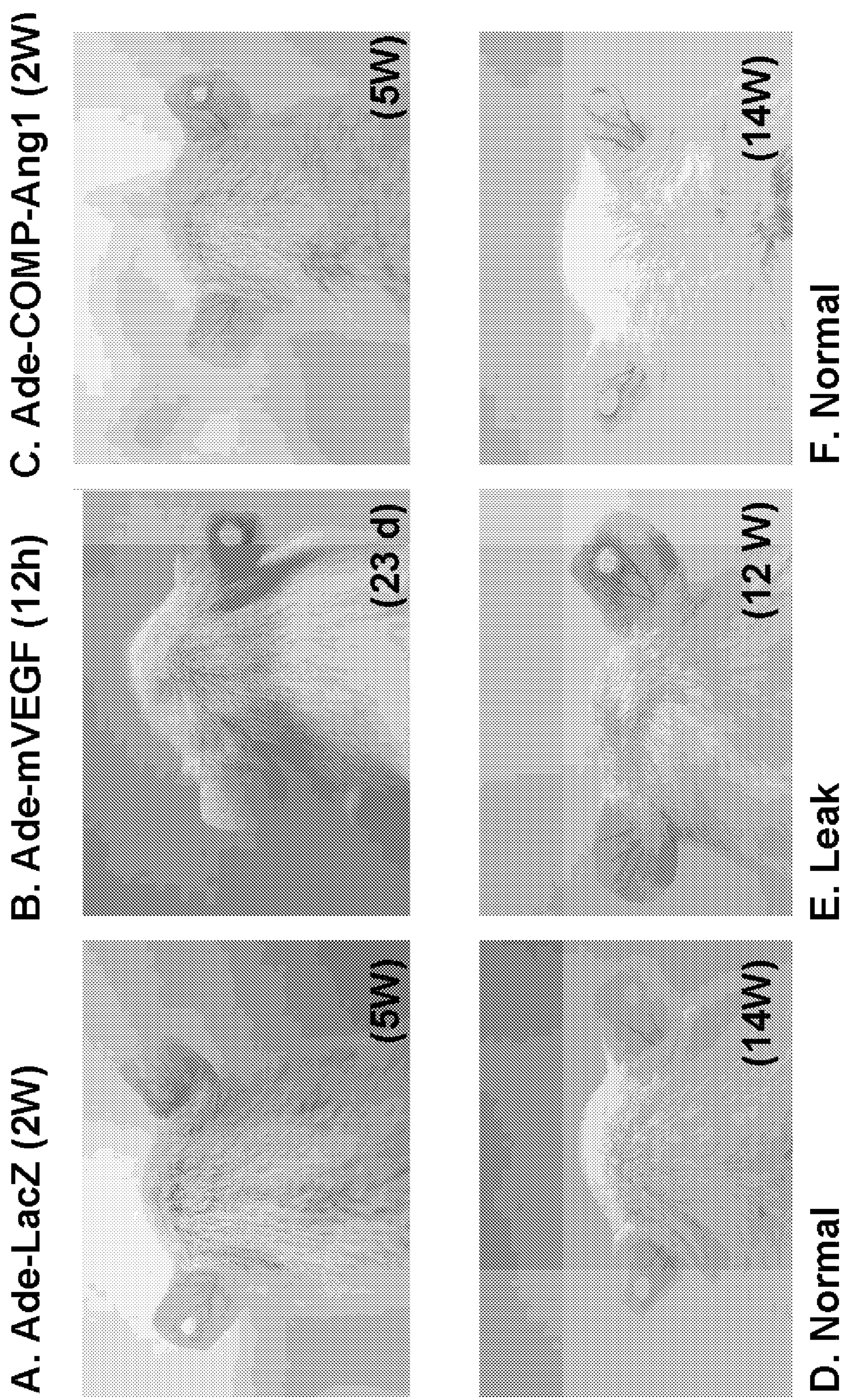
FIGS. 3A-3F show the effect of VEGF and COMP-Ang1 in punched-hole injury in the ear of various ages. Indicated ages of male FVB/n mice were treated with $1\times10^9$ pfu Ade-LacZ (Control, A and D), $1\times10^8$ pfu Ade-mVEGF (mouse VEGF, B and E) or $1\times10^9$ pfu Ade-COMP-Ang1 (C and F) virus, and a closed punched-hole injury was made in the ear. At indicated times or days later, ears were photographed.

Young mice (3 weeks old) that received adenoviral mouse VEGF ($1\times10^{8}$ pfu) showed marked vascular leakage with hemorrhage (FIG. B) in punched injury area while young mice that received adenoviral LacZ ($1\times10^{9}$ pfu) or adenoviral COMP-Ang1 ($1\times10^{9}$ pfu) showed no sign of vascular leakage (FIGS. 3A, 3C). Notably, moderate angiogenesis was visible around the punched injury area. Adult mice (12 weeks old) that received adenoviral mouse VEGF ($1\times10^{8}$ pfu) showed moderate vascular leakage with hemorrhage (FIG. E) in the punched injury area whereas adult mice that received adenoviral LacZ ($1\times10^{9}$ pfu) or adenoviral COMP-Ang1 ($1\times10^{9}$ pfu) showed no sign of vascular leakage (FIGS. 3D, 3F). Notably, moderate angiogenesis was visible around punched injury area.

Figure 4:
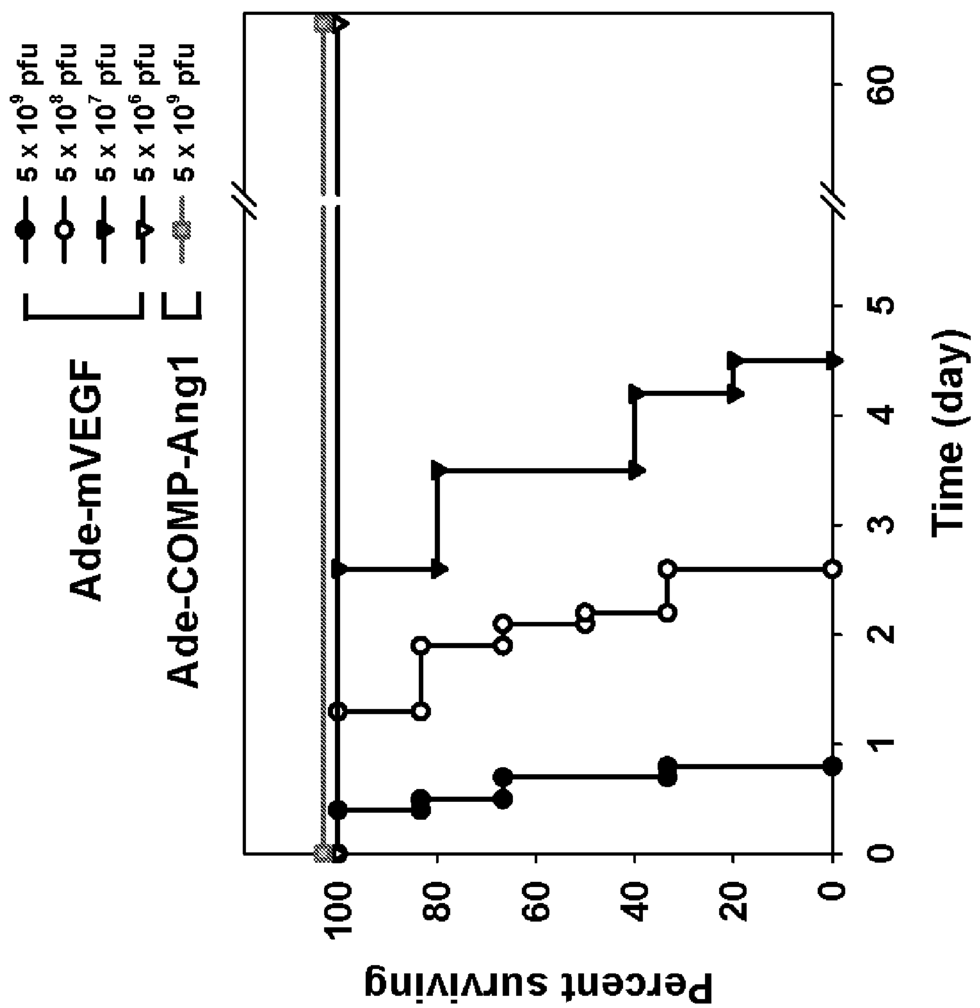
FIG. 4 shows survival rate of mice treated with VEGF and COMP-Ang1. Eight week-old male FVB/n mice were treated with indicated amount of Ade-mVEGF or Ade-COMP-Ang1 virus, and survival rate was measured.

Adult mice (12 weeks old) that received high and moderate titer of adenoviral mouse VEGF ($1\times10^{9}$ to $1\times10^{7}$ pfu) became sick and died within a few days in a dose-dependent manner from severe vascular leakage in most organs including liver and lung, while adult mice that received high titer of adenoviral COMP-Ang1 ($1\times10^{9}$ pfu) were normal and healthy for their lives (FIG. 4).

Figure 5:
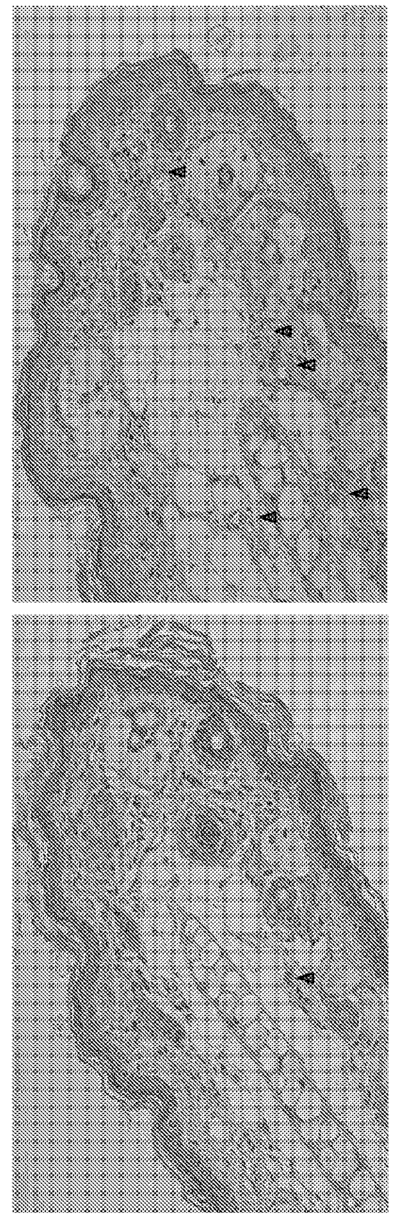
FIGS. 5A-5D show the effect of COMP-Ang1 on vascular remodeling in ear skin. Eight week-old male FVB/N mice were treated with daily injection of 200 μg of BSA (A and C) or 200 μg of COMP-Ang1 recombinant protein (B and D) for 14 days. Sections of ear skin were stained with H&E (A and B) and blood vessels of whole-mounted ear skin were visualized with PECAM-1 (CD31) immunostaining (red) (C and D). The mice treated with COMP-Ang1 have prominently enlarged blood vessels (red arrow-heads in H&E staining) in the ear skin.
Figure 5:
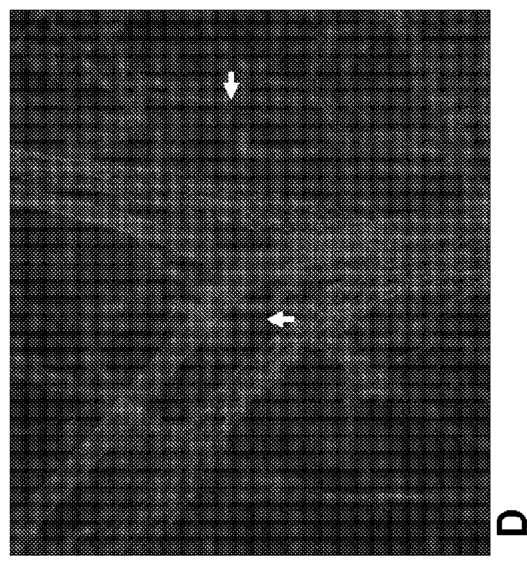
Figure 5:
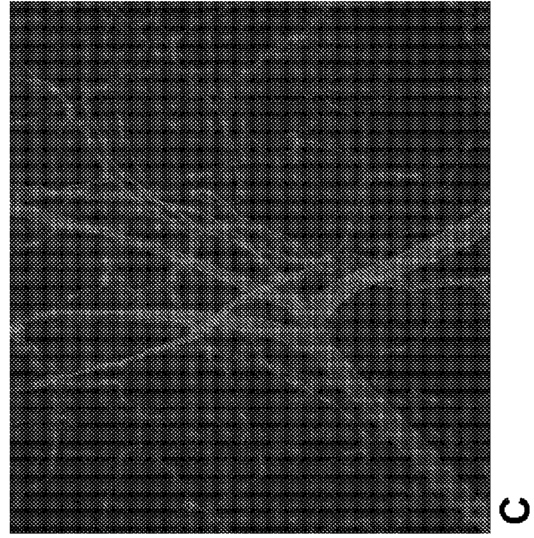

Ear sections with hematoxilin-eosin staining showed that blood vessels are more numerous and enlarged in COMP-Ang1 treated mice compared to control treated mice (FIGS. 5A, 5B). Whole mount preparation of ear skin, in which vessels were visualized with anti-PECAM antibody and secondary rhodamine-labeled anti-hamster IgG antibody revealed that dermal venules and capillaries were enlarged and were numerous in COMP-Ang1 treated mice compared to control treated mice (FIG. 5C, 5D).

Figure 6:
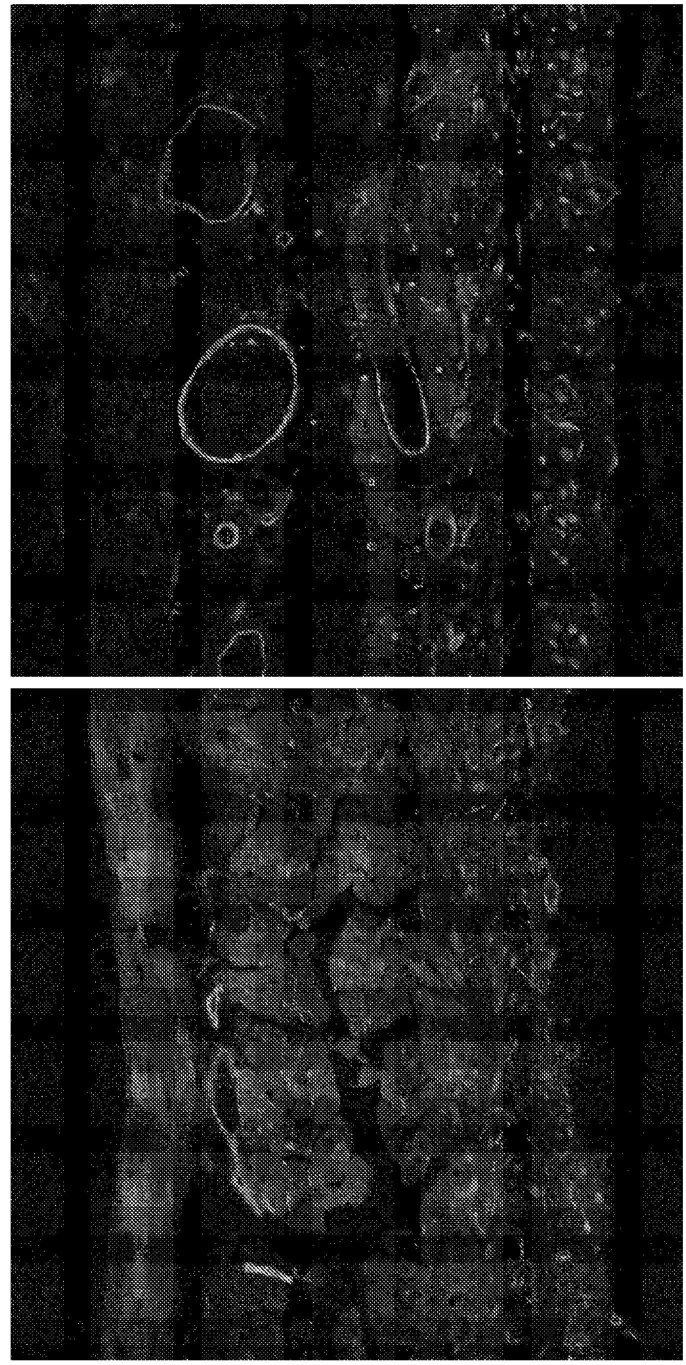
FIGS. 6A-6B show the effect of COMP-Ang1 on vascular remodeling in abdominal skin. Vascular specific expression of eGFP using Tie2 promoter transgenic mice (eight week-old male Tie2-eGFP mice) were treated with daily injection of 200 μg of BSA (A) or 200 μg of COMP-Ang1 recombinant protein (B) for 14 days. Blood vessels of abdominal skin sections were visualized with PECAM-1 (CD31) immunostaining (red). The mice treated with COMP-Ang1 have prominently enlarged blood vessels.

These phenomena also occurred on skin. More enlarged and numerous blood vessels were noticeable on superficial dermal layer of abdominal skin in COMP-Ang1 treated mice compared to control treated mice (FIG. 6).

Figure 7:
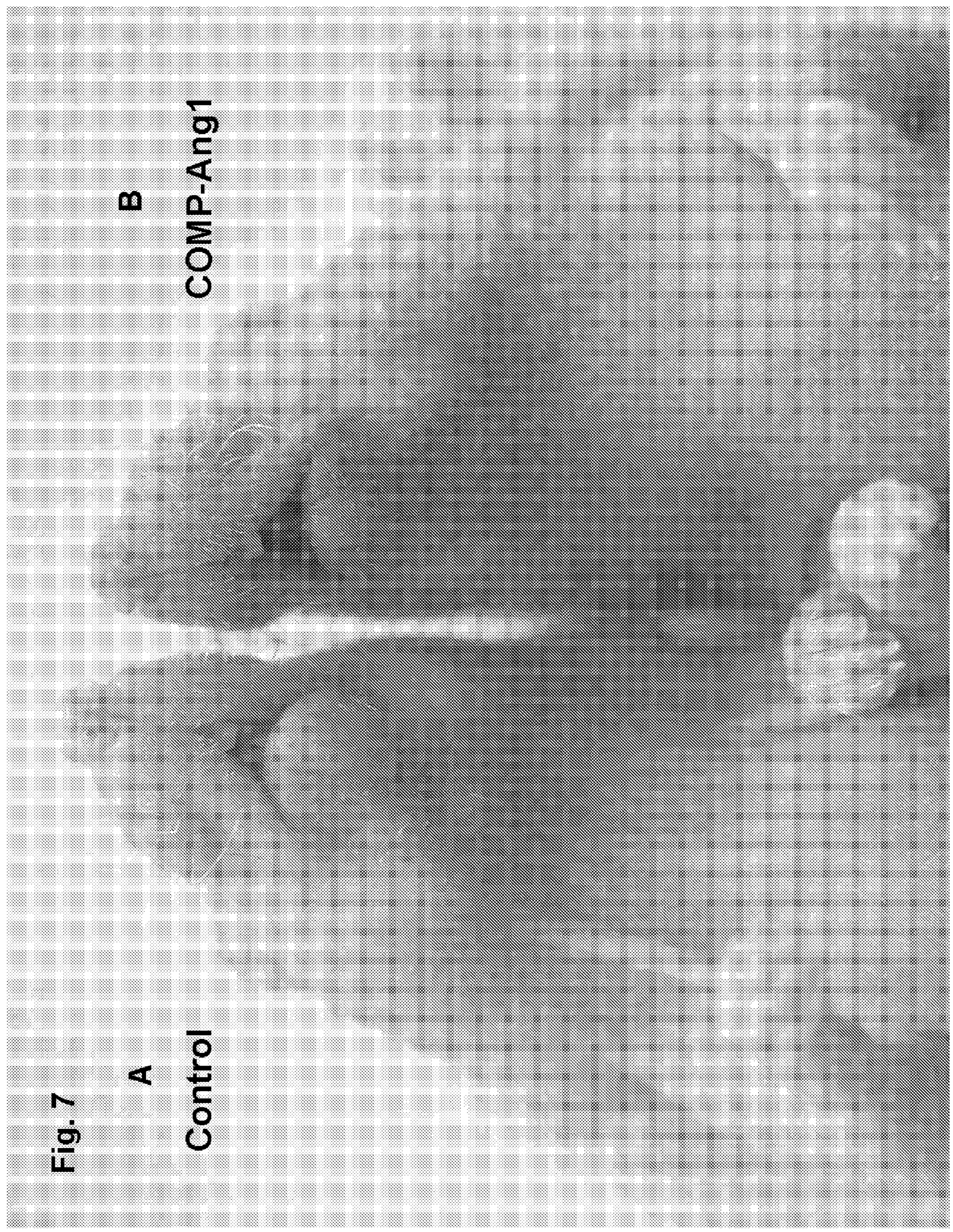
Figure 8:
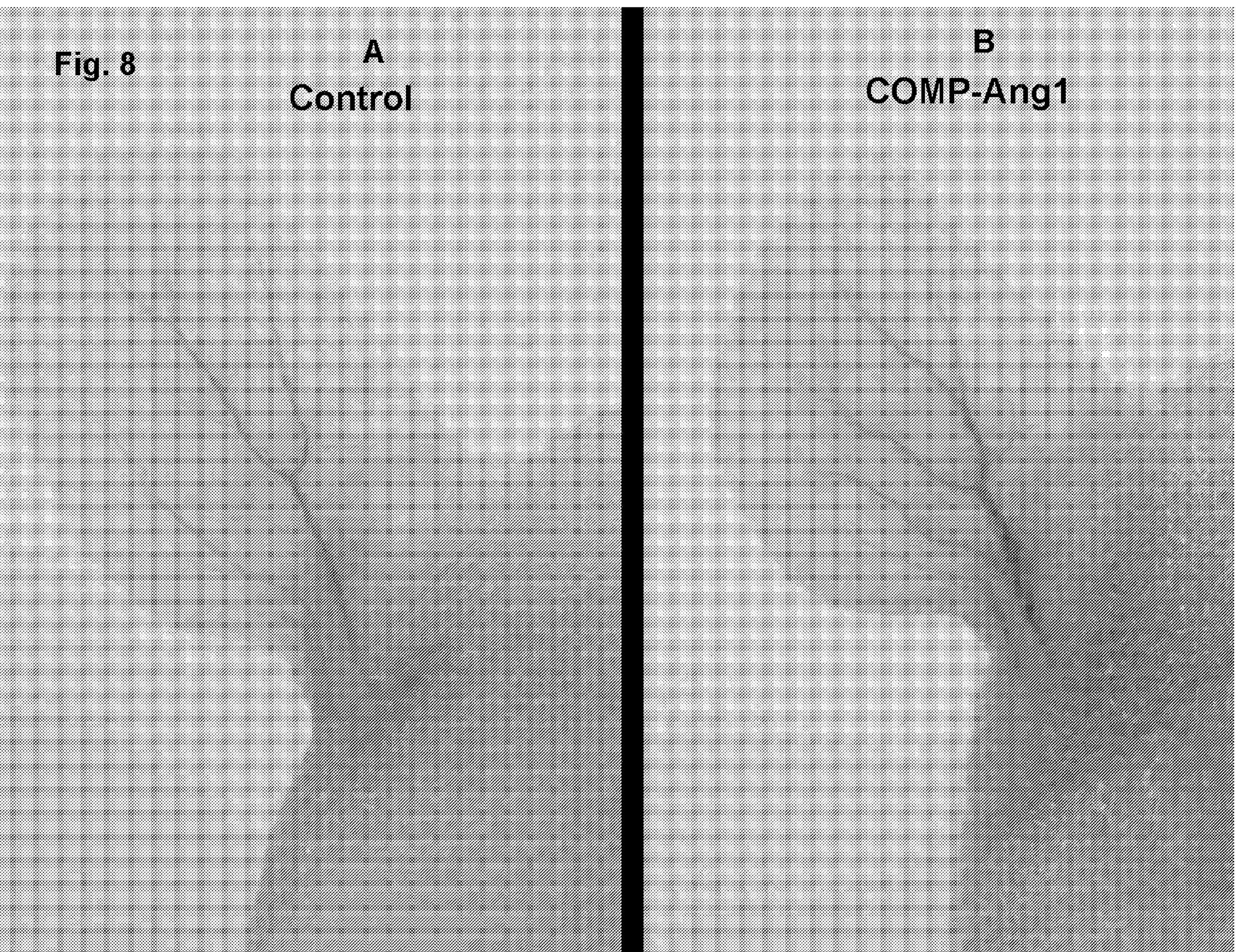
FIGS. 8A-8B show the effect of adenoviral COMP-Ang1 on skin color. Eight week-old male BALB/c-nu nude mice were treated with $1\times10^9$ pfu Ade-LacZ (Control, A) or Ade-COMP-Ang1 (B). Five weeks later, blood vessels of ear skin were photographed. The mice treated with Ade-COMP-Ang1 show striking increase in number, size and branching patterns of blood vessels in the ear compared to control-treated mice.

These phenomena are more evident when we treated nude mice with COMP-Ang1. The skins of face, neck and chest in COMP-Ang1-treated mice were redder than those in control-treated mice (FIG. 7). COMP-treated mice showed striking increase in number, size and branching patterns of blood vessels in the ear compared to control-treated mice (FIG. 8).

Figure 9:
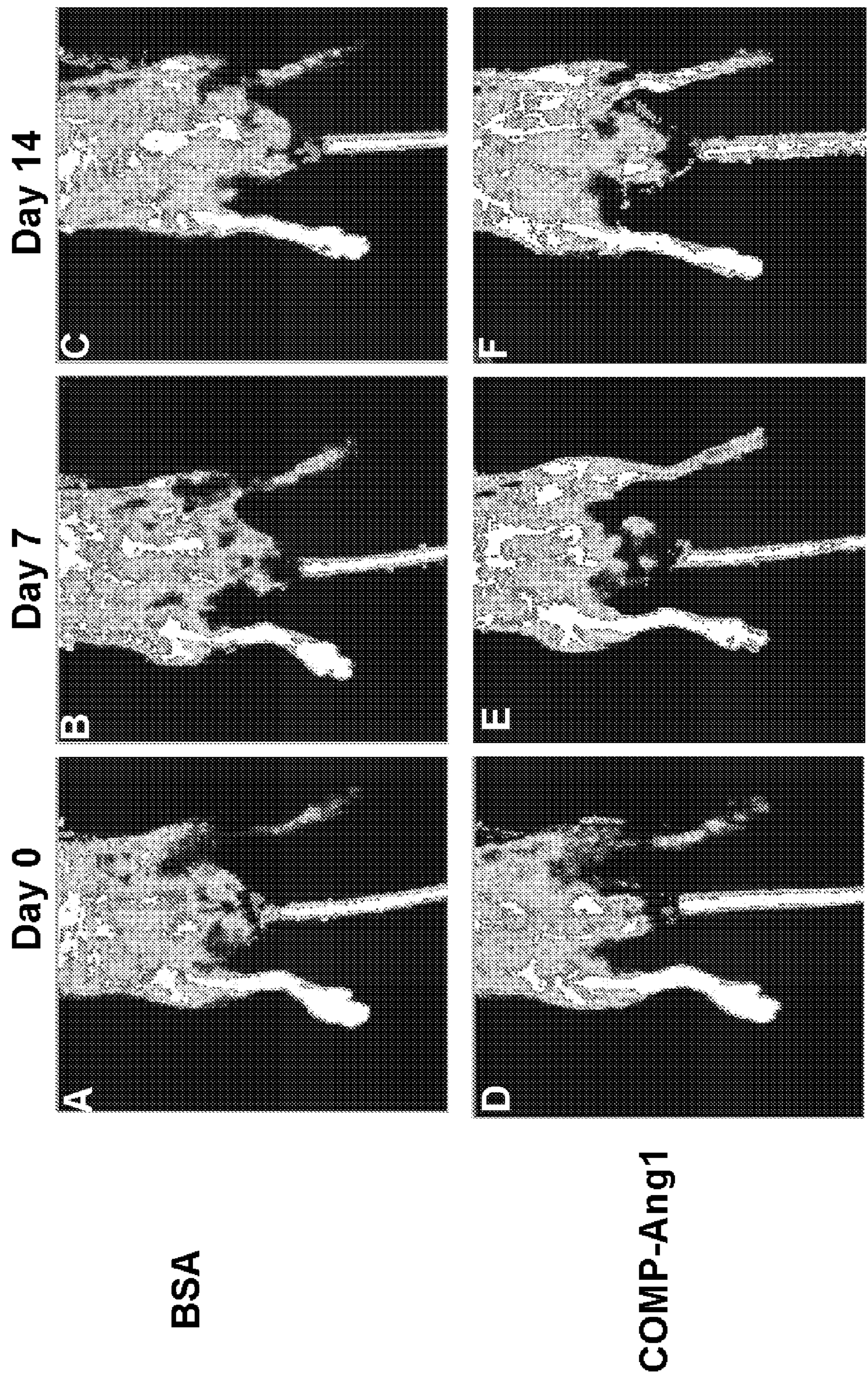
FIGS. 9A-9F show the effect of adenoviral COMP-Ang1 on ischemic hindlimb. Ischemic hindlimb mouse model was generated in eight week-old male BALB/c-nu nude mice by partial ligation of femoral artery. Then, 100 μg of BSA (A, B, C) or 100 μg of COMP-Ang1 (D, E, F) was injected directly into ischemic muscles at day 0 (A and D), 3 (B and E) and 5 (C and F). Indicated times, blood flow in the ischemic legs were measured by laser micro-Doppler method. Compared to BSA treatment, there is almost complete recovery of blood flow in the ischemic hindlimb in COMP-Ang1 treated mice.

Based on these intriguing results, COMP-Ang1 may be useful for treating patients with ischemic organ disease including heart, limbs, brain, and stomach. Therefore, we generated ischemic hindlimb mouse model by partial ligation of femoral artery and followed up blood flow in the ischemic area by laser micro-Doppler method. Then, adenoviral COMP-Ang1 ($5\times10^{7}$ pfu) or adenoviral LacZ ($5\times10^{7}$ pfu) was injected directly into ischemic muscles. Compared to adenoviral LacZ treatment, there was almost complete recovery of blood flow in the ischemic hindlimb of the adenoviral COMP-Ang1 treated mice (FIG. 9). Therefore, COMP-Ang1 is useful for treating patients with ischemic diseases.

Recovery of Erectile Dysfunction

Figure 10:
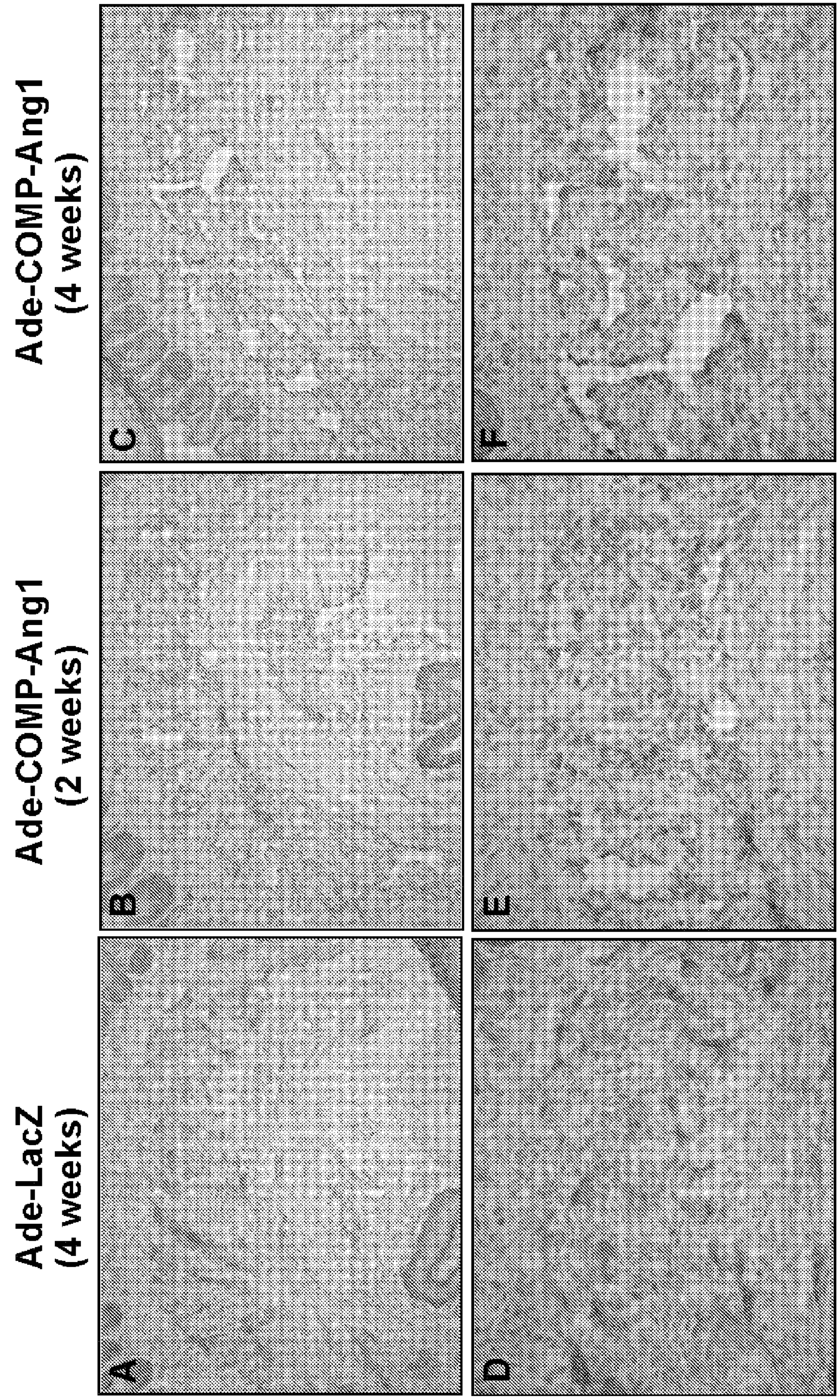
FIGS. 10A-10F show the effect of COMP-Ang1 on corpora cavernosal sinus of penis. Eight week-old male FVB/N mice were treated with $1\times10^9$ pfu Ade-LacZ (A and D) or Ade-COMP-Ang1 (B, C, E and F). Indicated times later, sections of penis were immunostained with anti-von-Willebrand factor antibody (pinkish violet). A, B and C, magnification ×40; D, E and F, magnification ×200. The penis of mouse treated with Ade-COMP-Ang1 shows enlarged corpora cavernosal sinus with induction of von-Willebrand factor in a time dependent manner.
Figure 11:
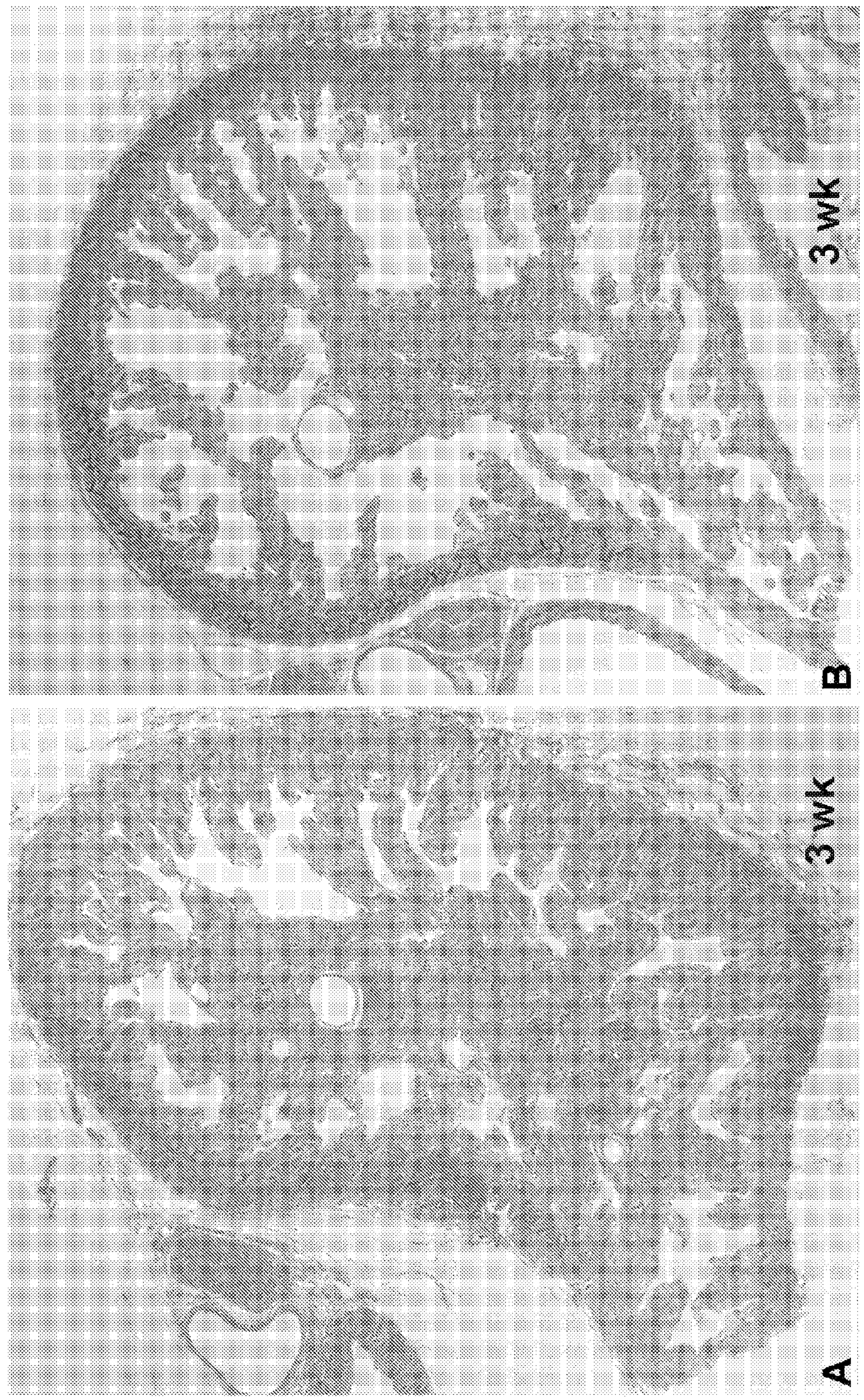
FIGS. 11A-11B show the effect of COMP-Ang1 on corpora cavernosal sinus of penis. Eight weeks-old male FVB/N mice were treated with treated with $1\times10^9$ pfu Ade-LacZ (A) or $1\times10^9$ pfu Ade-COMP-Ang1 (B). Three weeks later, epoxy sections of penis were stained with toluidine blue. The penis of mouse treated with Ade-COMP-Ang1 shows enlarged corpora cavernosal sinus.
Figure 12:
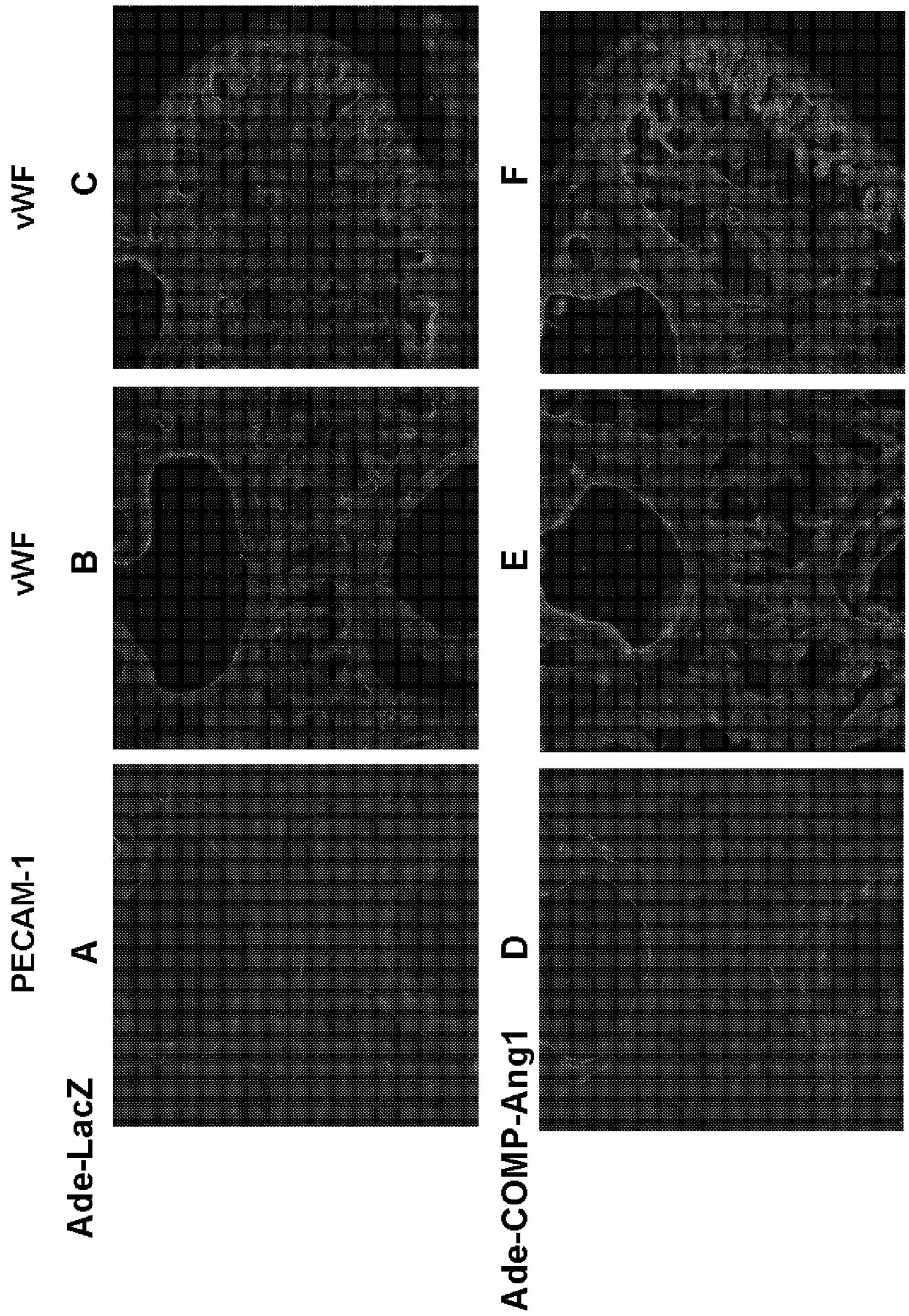
FIGS. 12A-12F show the effect of COMP-Ang1 on corpora cavernosal sinus of penis. Eight week-old male FVB/N mice were treated with $1\times10^9$ pfu Ade-LacZ (A, B and C) or $1\times10^9$ pfu Ade-COMP-Ang1 (D, E and F). Three weeks later, sections of penis were immunostained with anti-PECAM-1 antibody (red) or anti-von-Willebrand factor antibody (red). Upper panels, magnification ×40; lower panels, magnification ×200. The penis of mouse treated with Ade-COMP-Ang1 (D-F) shows enlarged corpora cavernosal sinus with induction of von-Willibrand factor in a time dependent manner.

Systemic treatment with COMP-Ang1 enlarged the space of corpora cavernosal sinus with induction of von-Willebrand factor in mice penis in a time dependent manner, while control did not produce any changes in mice penis (FIG. 10). This phenomenon is more evident in high magnification analysis (FIG. 11). In addition, PECAM-1 expression was increased in surrounding endothelial cells of corpora cavernosum in COMP-1 treated mice (FIG. 12).

Figure 13:
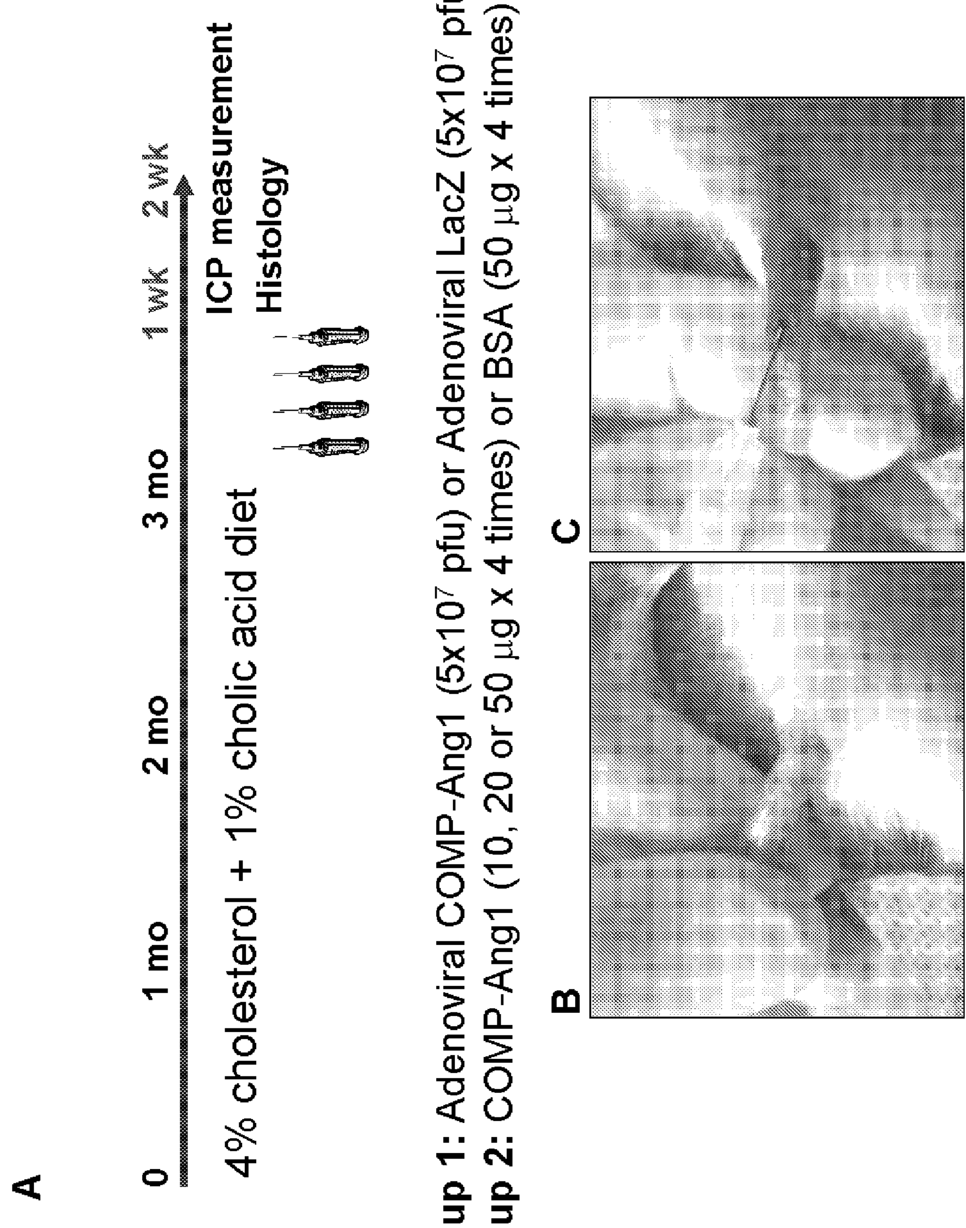
FIGS. 13A-13C show the protocol of generation of hypercholesterolemic erectile dysfunctional rat model and treatment of COMP-Ang1. (A) Eight-week old male Sprague-Dawley rat were fed with 4% cholesterol plus 1% cholic acid diet for 3 months. Then, adenoviral COMP-Ang1 ($5\times10^7$ pfu) or adenoviral LacZ ($5\times10^7$ pfu) was injected directly into corpora cavernosum of hypercholesterolemic erectile dysfunctional rat (B and C). Alternatively, 10-50 μg of COMP-Ang1 recombinant protein (every alternative day for 4 times) or 50 μg of bovine serum albumin (every alternative day for 4 times) was injected directly into corpora cavernosum of hypercholesterolemic erectile dysfunctional rat (B and C).
Figure 14:
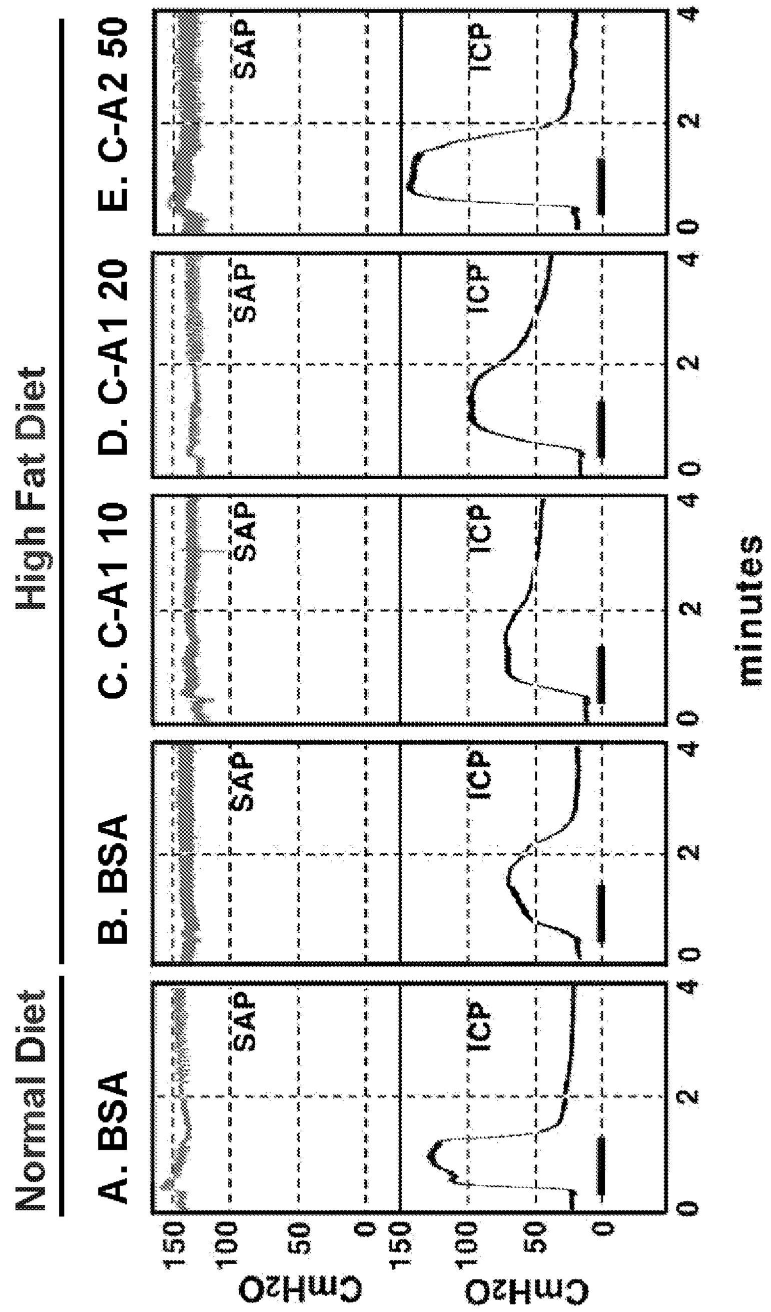
FIGS. 14A-14E show the effect of COMP-Ang1 on erectile function in hypercholesterolemic erectile dysfunctional rat. Fifty μg of BSA (A and B) or indicated COMP-Ang1 recombinant protein (C: 10 μg, C-A1 10; D: 20 μg, C-A1 20; E: 50 μg, C-A1 50) was injected directly into corpora cavernosum of normal diet rat (A) or hypercholesterolemic erectile dysfunctional rat (B-E) as every alternative day for 4 times. Two weeks later, intra-corporal pressure (ICP) after neural stimulation and systemic arterial pressure (SAP) were measured for the indicated minutes.
Figure 15:
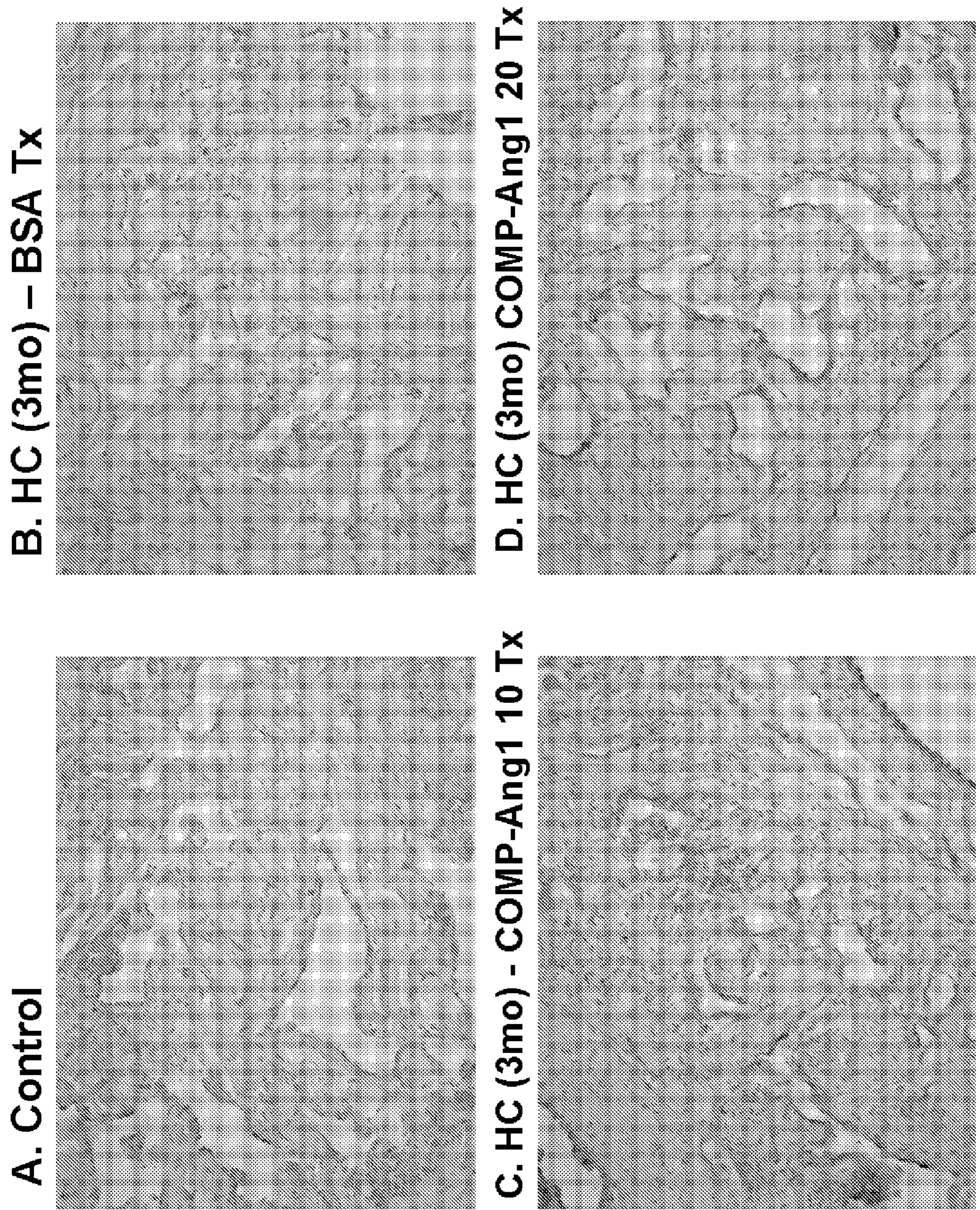
FIGS. 15A-15D show the effect of COMP-Ang1 on penis of hypercholesterolemic erectile dysfunctional rat. Fifty μg of BSA (A and B) or indicated COMP-Ang1 recombinant protein (C: 10 μg, C-A1 10; D: 20 μg, C-A1 20) was injected directly into corpora cavernosum of normal diet rat (A, Control) or hypercholesterolemic erectile dysfunctional rat (B, C, and D, HC) every other day for 4 times. Two weeks later, sections of penis were immunostained with anti-von-Willebrand factor antibody (pinkish violet). The penis of mouse treated with COMP-Ang1 shows enlarged corpora cavernosal sinus with induction of von-Willebrand factor in a dose-dependent manner.
Figure 16:
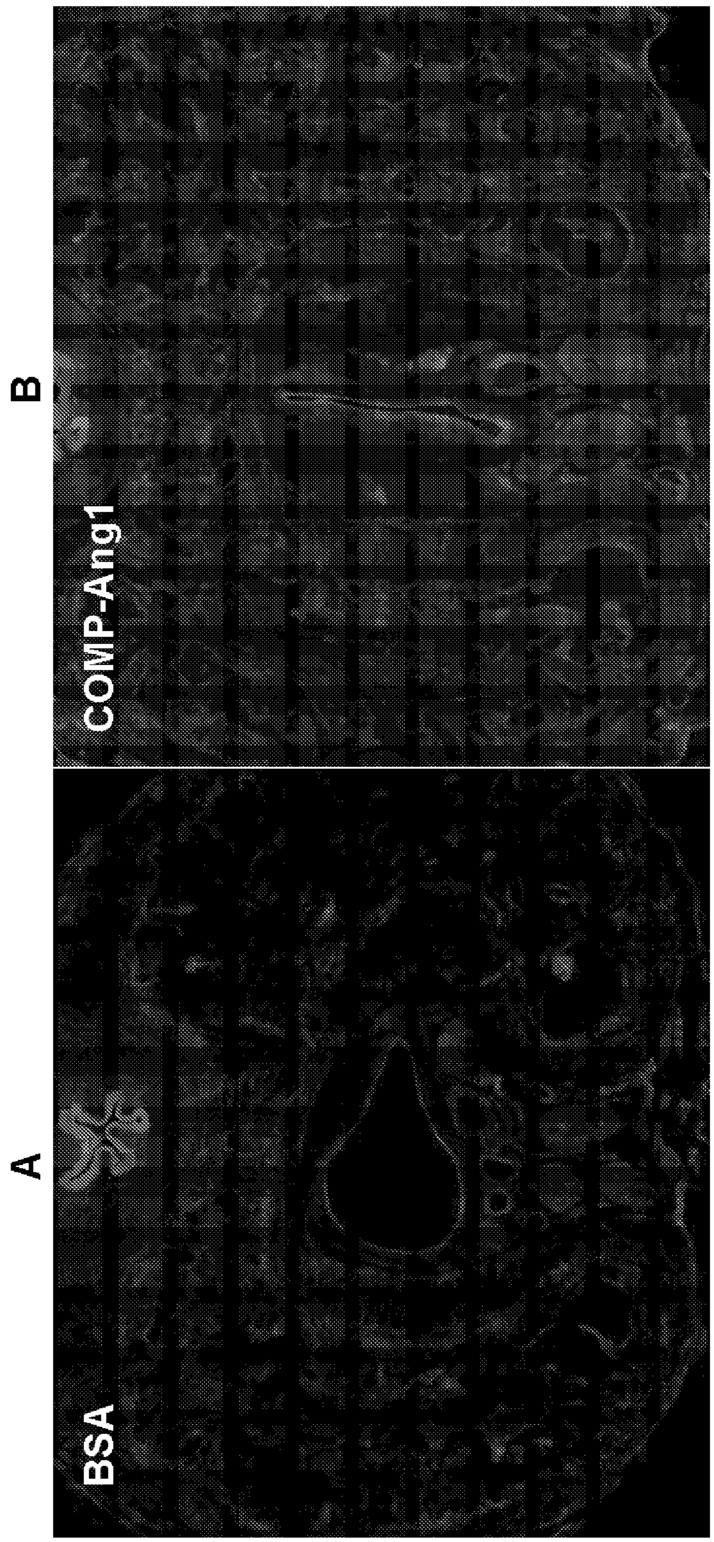
FIGS. 16A-16B show the effect of COMP-Ang1 on penis of hypercholesterolemic erectile dysfunctional rat. Fifty μg of BSA (A) or COMP-Ang1 (B) recombinant protein was injected directly into corpora cavernosum of hypercholesterolemic erectile dysfunctional rat as every alternative day for 4 times. Two weeks later, sections of penis were immunostained with anti-endothelial nitric oxide synthase (eNOS) antibody (red). The penis treated with COMP-Ang1 shows induction of eNOS (A).

Based on these results, COMP-Ang1 may be useful for treating patients with atherosclerotic erectile dysfunction. Therefore, we generated hypercholesterolemic erectile dysfunctional rat model by feeding 4% cholesterol plus 1% cholic acid diet for 3 months (FIG. 13). Then, adenoviral COMP-Ang1 ($5\times10^7$ pfu) or adenoviral LacZ ($5\times10^7$ pfu) was injected directly into corpora cavernosum of hypercholesterolemic erectile dysfunctional rat (FIG. 13). Alternatively, 10-50 μg of COMP-Ang1 recombinant protein (every other day for 4 times) or 50 μg of bovine serum albumin (every other day for 4 times) was injected directly into corpora cavernosum of hypercholesterolemic erectile dysfunctional rat (FIG. 13). Compared to normal feeding rat, there was a significant reduction of intra-corporal pressure after neural stimulation in hypercholesterolemic rat at 2 weeks after adenoviral LacZ ($5\times10^7$ pfu) treatment (FIG. 14). In contrast, there was an almost complete recovery of intra-corporal pressure after neural stimulation in hypercholesterolemic rat at 2 weeks after adenoviral COMP-Ang1 ($5\times10^7$ pfu) treatment (FIG. 14). Direct injection of COMP-Ang1 recombinant protein produced recovery of intra-corporal pressure after neural stimulation in hypercholesterolemic rat in a dose-dependent manner, while direct injection of BSA did not produce any recovery of intra-corporal pressure (FIG. 14). Histological analysis revealed that intra-cavernosal COMP-Ang1 treatment enlarged space of corpora cavernosal sinus with induction of von-Willebrand factor in hypercholesterolemic erectile dysfunctional rat in a dose-dependent manner, while intra-cavernosal BSA treatment did not produce any change in corpora cavernosal sinus (FIG. 15). Nitric oxide (NO) production by activation of endothelial NO synthase (eNOS) of the endothelium is the main regulator for penile erection. We asked whether eNOS expression is involved in COMP-Ang1-induced restoration of erectile function in hypercholesterolemic erectile dysfunctional rat. Immunofluorescent staining of eNOS indicated that upregulation of eNOS was noted not only in the endothelium but also in the corpora cavernosal tissues in COMP-Ang1-treated penis (FIG. 16). Thus, COMP-Ang1-induced restoration of erectile function in hypercholesterolemic rat could be mediated by upregulation of eNOS in the penis. Therefore, we conclude that COMP-Ang1 is useful for treating patients with atherosclerotic erectile dysfunction, who may not respond to Viagra® or Cialis®.

Sepsis

Figure 17:
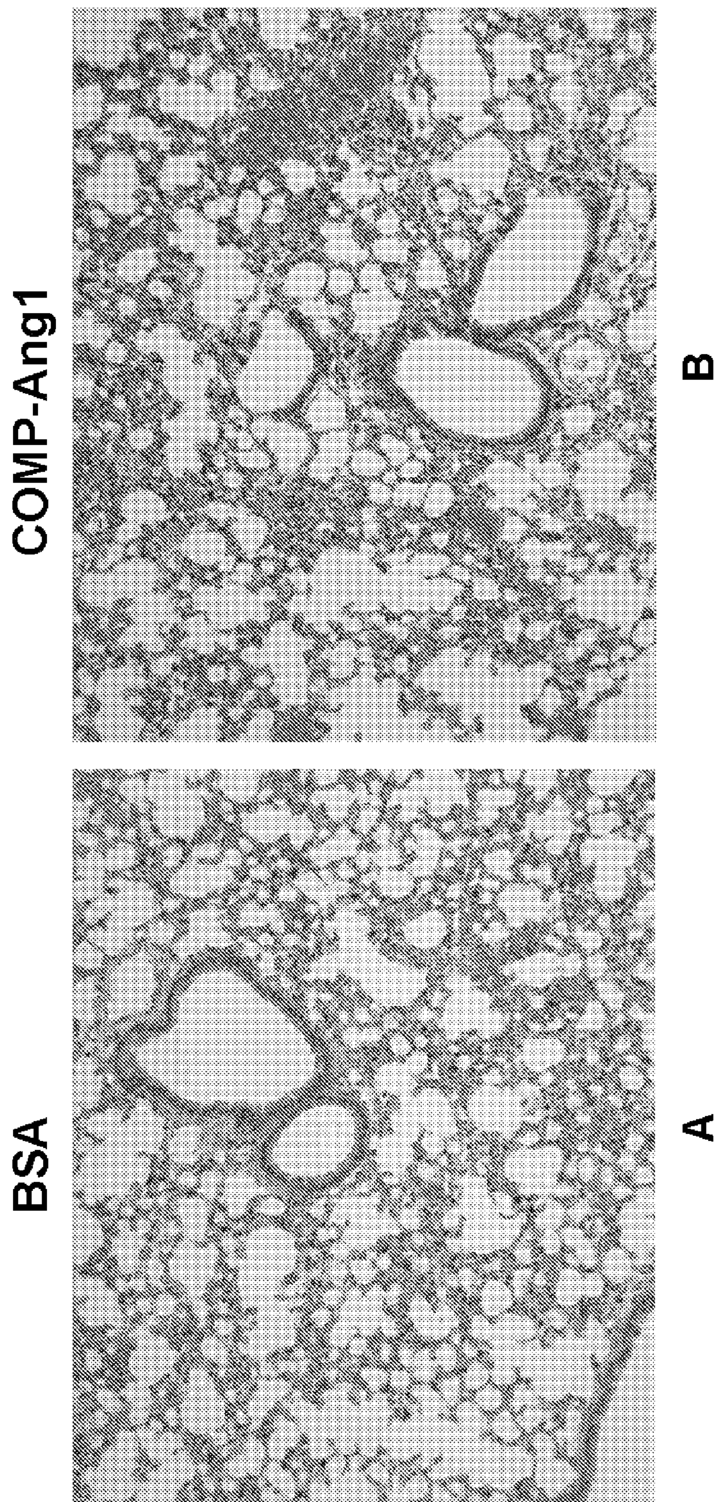
FIGS. 17A-17B show the effect of COMP-Ang1 on blood vessels of the lung. Eight week-old male FVB/N mice were treated with daily injection of 200 μg of BSA (A) or 200 μg of COMP-Ang1 recombinant protein (B) for 14 days. Sections of lung were stained with H&E.
Figure 18:
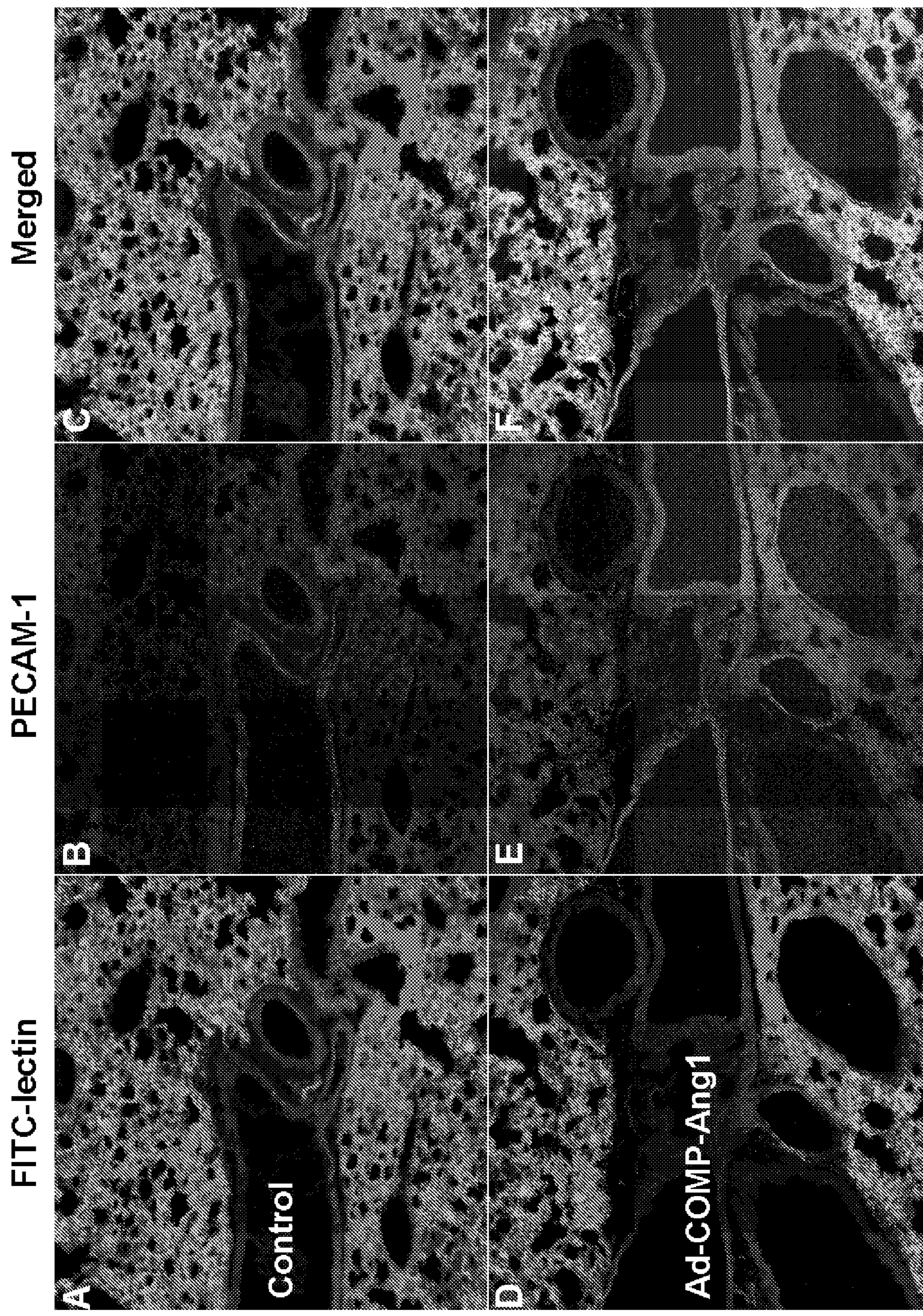
FIGS. 18A-18F show the effect of COMP-Ang1 on blood vessels of the lung. Eight week-old male FVB/N mice were treated with $1\times10^9$ pfu Ade-LacZ (Control, A, B, C) or Ade-COMP-Ang1 (D, E, F). Two weeks later, FITC-lectin was injected into the tail vein of mice, lung samples were harvested at 3 min when the skin color of the face, and lung sections were immunostained with anti-PECAM-1 (CD31) antibody (red, B and E). FITC-lectin-labeled vascular endothelial cells are visualized as green (green, A and D). Both images are merged (C and F).

Because Ang1 receptor, Tie2, abundantly expressed in the endothelial cells of adult lung, we examined the effect of COMP-Ang1 in lung. Histological analysis suggests that COMP-Ang1 appears to increase health and non-leaky capillary network in lung as evidenced by HE staining analysis (FIG. 17) and perfusion staining with FITC-lectin (FIGS. 18A, 18D). In addition, PECAM-1 was markedly increased in lung endothelial cells of COMP-Ang1 treated mice compared to control treated mice (FIGS. 18B, 18E).

Figure 19:
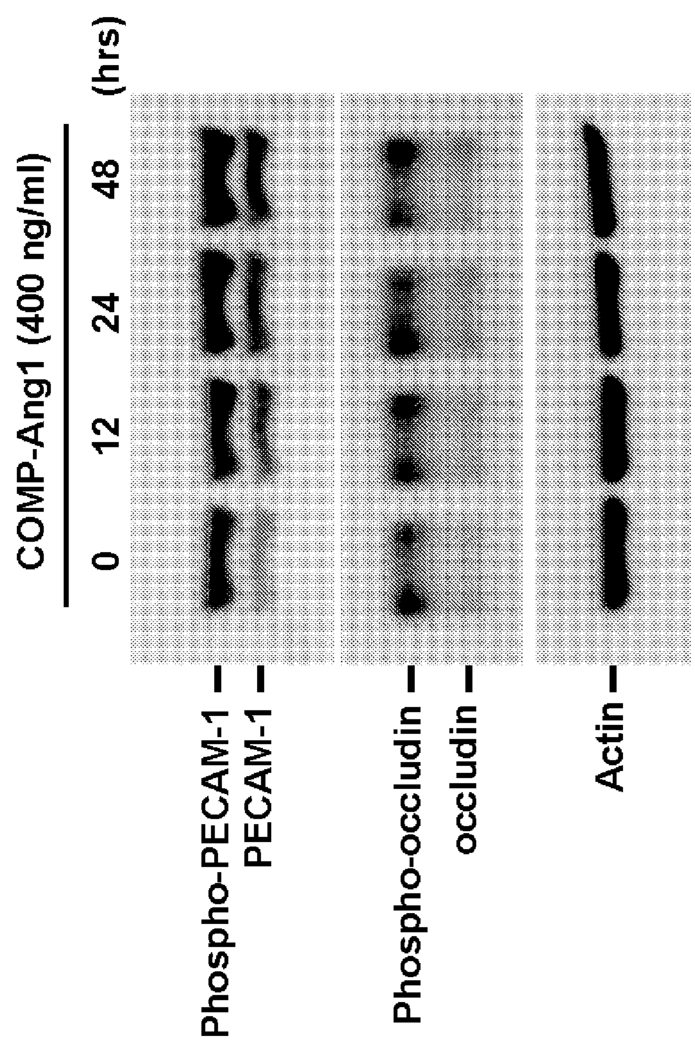
FIG. 19 shows the effect of COMP-Ang1 on phosphorylation of PECAM-1 and occluding in primary cultured endothelial cells. Primary cultured human umbilical vein endothelial cells (HUVECs) were incubated for 16 hr in 1% serum-containing M-199 medium, then incubated with 400 ng of COMP-Ang1 for the indicated times. After treatment, cell lysates were harvested. Each lane contains 50 μg of total protein from the cell lysates. Blots were probed with anti-PECAM-1 antibody or anti-occuldin antibody. The membrane was stripped and reprobed with anti-actin antibody to verify equal loading of protein in each lane.
Figure 20:
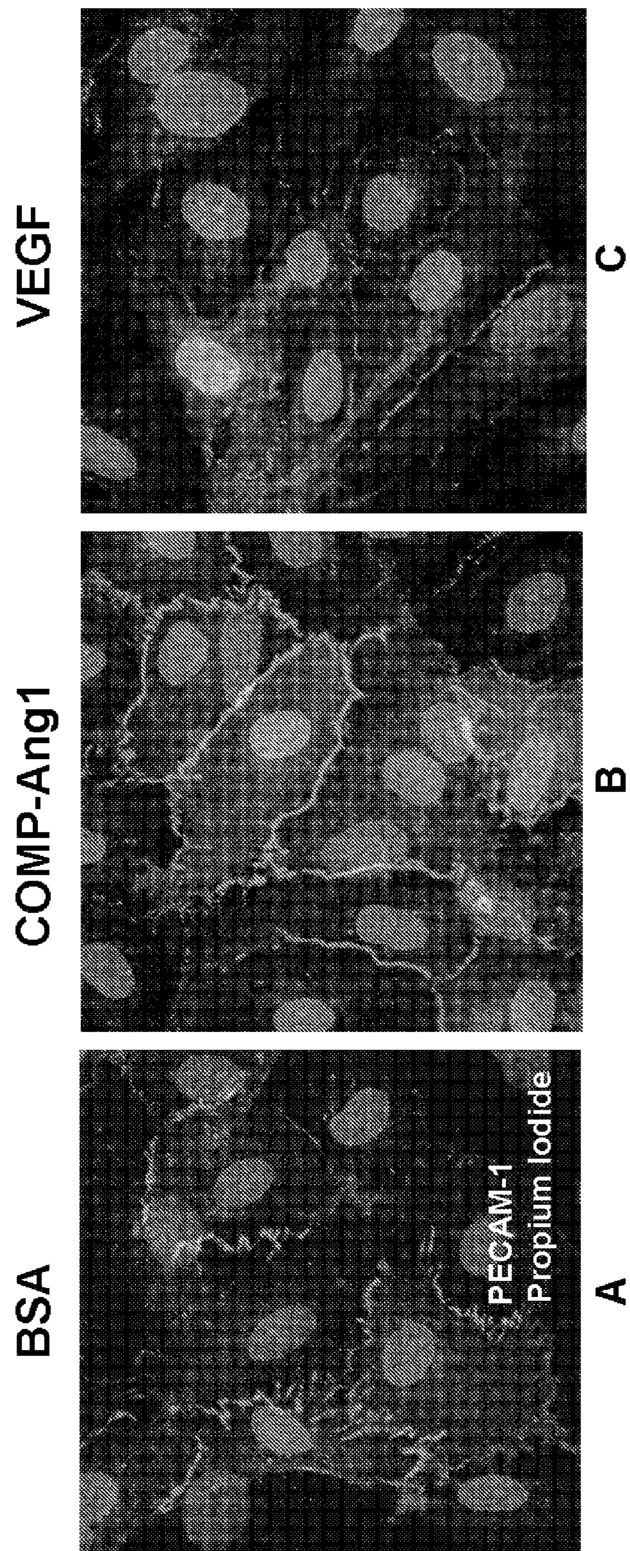
FIGS. 20A-20C show the effect of COMP-Ang1 on distribution of PECAM-1 in primary cultured endothelial cells. Primary cultured HUVECs were incubated for 16 hr in 1% serum-containing M-199 medium, then cells were incubated with 400 ng of BSA (A) or COMP-Ang1 (B), or 20 ng of vascular endothelial growth factor (VEGF) (C) for 30 min. After treatment, the cells were fixed, and immunostained with anti-PECAM-1 antibody (green) and stained with propium iodide (red, nuclear staining).

COMP-Ang1 (400 ng/ml) moderately increases levels of phospho-PECAM-1, PECAM-1, phosphor-occludin, and occludin, which are important molecules for maintaining intercellular junctions, in a time dependent manner in primary cultured human umbilical vein endothelial cells (HUVECs) (FIG. 19). COMP-Ang1 (400 ng/ml) enhanced peripheral rearrangement of PECAM-1 to the cell boundary in cultured endothelial cells while VEGF (20 ng/ml) disrupted peripheral rearrangement of PECAM-1 (FIG. 20).

Figure 21:
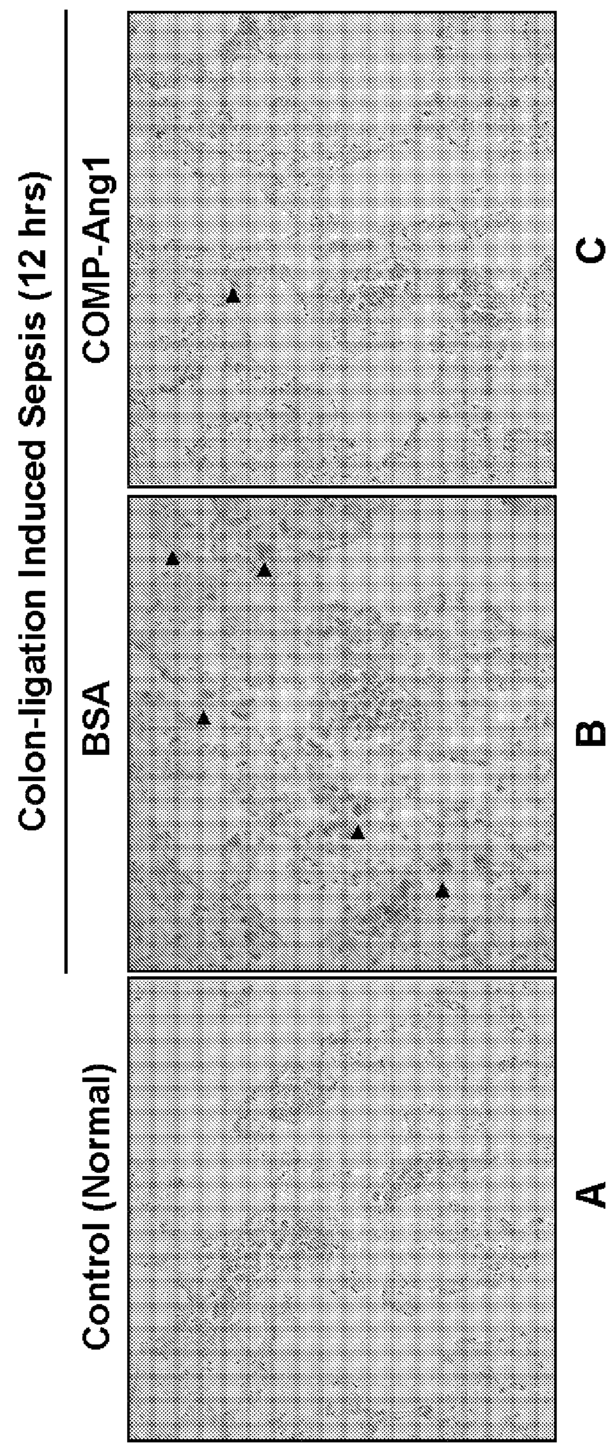
FIGS. 21A-21C show that COMP-Ang1 reduces endotoxin-induced EB dye-vascular leak in the lung. Eight weeks-old male FVB/N mice were given control buffer (A, normal), control buffer plus endotoxin (7.5 μg/g of body weight) (B), or COMP-Ang1 (100 μg) plus endotoxin (7.5 μg/g of body weight) (C). Evan blue (EB) dye (30 mg/kg of body weight) was administered immediately after treatment of indicated agents, and sacrificed after 6 hr. Lung tissues were stained with eosin (upper panels) or TUNEL (lower panels). Notable numbers of EB dye-accumulating macrophages (arrow heads) are observed in endotoxin-treated samples, while no EB dye accumulating macrophages are observed in CB-treated samples. COMP-Ang1 reduces the numbers of EB dye-accumulating macrophages.

In the colon-ligation-induced sepsis mouse model, there is a profound vascular leak in the lung as assessed by Evans blue leak analysis (FIG. 21). COMP-Ang1 treated mice showed reduced vascular leak in the lung (FIG. 21). Therefore, COMP-Ang1 is useful for treating patients with sepsis-induced vascular leakage.

Long-Term and Sustained COMP-Ang1 Induces Long-lasting Vascular Enlargement and Enhanced Blood Flow (COMP-Ang1 in Vascular Remodeling)

Ang1 is known to be a ligand to Tie2 tyrosine kinase receptor expressed on endothelial cells (Davis et al., 1996, Cell. 87:1161-1169). Ang1/Tie2 signaling is thought be involved in branching and remodeling of the primitive vascular network and in the recruitment of mural cells during development (Dumont et al., 1994, *Genes Dev.* 8:1897-1909; Suri et al., 1996, Cell. 87:1171-1180). Transgenic overexpression of Ang1 using the skin-specific keratin-14 promoter produces the leakage-resistant and enlarged vessels with an increased number of endothelial cells in skin (Suri et al., 1998, Science. 282:468-471; Thurston et al., 1999, Science. 286:2511-2514). Gene transfer of Ang1 into ischemic tissues produces notably enlarged blood vessels (Shyu et al., 1998, Circulation. 98:2081-2087; Chae et al., 2000, Arterioscler Thromb Vasc Biol. 20:2573-2578). Baffert et al., recently identified that Ang1-induced vascular enlargement could be the result of endothelial proliferation in trachea mucosa (Baffert et al., 2004, Circ Res. 94:984-992). Thus, a cardinal feature of Ang1-induced vascular remodeling is vascular enlargement resulting from endothelial cell proliferation in adult animals (Suri et al., 1998, Science. 282:468-471; Thurston et al., 1999, Science. 286:2511-2514; Shyu et al., 1998, Circulation. 98:2081-2087; Chae et al., 2000, Arterioscler Thromb Vasc Biol. 20:2573-2578; Baffert et al., 2004, Circ Res. 94:984-992).

Given that Ang1-induced therapeutic benefits correlated with vascular enlargement in the ischemic tissues (Shyu et al., 1998, Circulation. 98:2081-2087; Chae et al., 2000, Arterioscler Thromb Vasc Biol. 20:2573-2578; Zhou et al., 2004, J Am Coll Cardiol. 44:897-903), enhanced blood flow through blood vessels enlarged by Ang1 treatment could provide a great therapeutic benefit to ischemic peripheral tissues. However, it is not known whether the tissues having Ang1-mediated enlarged vessels have more blood flow. In addition, the effective dose and treatment period of Ang1 for inducing effective vascular enlargement is not known. Moreover, it is not known whether Ang1-mediated vascular enlargement regresses when Ang1 stimulation is withdrawn.

We have recently developed a soluble, stable and potent Ang1 variant, COMP-Ang1 (Cho et al., 2004, Proc Natl Acad Sci USA. 101:5547-52, the contents of which are incorporated by reference herein in its entirety, especially with respect to methods of creating COMP-Ang1). To create this protein, we replaced the amino-terminal portion of Ang1 with the short coiled-coil domain of cartilage oligomeric matrix protein (COMP). COMP-Ang1 is more potent than native Ang1 in phosphorylating the Tie2 receptor and signaling via Akt in primary cultured endothelial cells (Cho et al., 2004, Proc Natl Acad Sci USA. 101:5547-52).

In the present application, we investigated effects of period and dose of COMP-Ang1 on vascular enlargement and tissue blood flow in adult mice and investigated a possible mechanism for long lasting vascular enlargement induced by long-term and sustained COMP-Ang1. To determine the underlying mechanism of COMP-Ang1-stimulated vascular remodeling in adult mice, we focused on the microvasculature of the trachea, which is distinguished by its simplicity and monolayer structure. Our results indicate that long term and sustained COMP-Ang1 produced by adenoviral delivery of COMP-Ang1 induces a long-lasting vascular enlargement and enhanced blood flow without enhanced pericyte recruitment in adult mice. Long-lasting Tie2 expression could be involved in the long-lasting vascular enlargement and enhanced blood flow.

Enlargement of tracheal blood vessels and enhancement of tracheal tissue blood flow induced by long-term and sustained exposure to COMP-Ang1 did not regress for up to 16 weeks despite the fact that exposure to COMP-Ang1 had already been discontinued at 6-7 weeks in adult mice. In comparison, enlargement of tracheal blood vessels induced by short-term intermittent exposure to COMP-Ang1 regressed upon discontinuation of recombinant COMP-Ang1 treatment. Therefore, long-lasting vascular enlargement and enhancement of blood flow can be achieved by long-term and sustained exposure to COMP-Ang1.

Like other therapeutic proteins, circulating COMP-Ang1 rapidly disappeared in the plasma, probably due to its trapping by the Tie2 receptor of lung endothelial cells. However, we were able to achieve long-term (>4 weeks) and sustained (>1,000 ng/ml) circulating COMP-Ang1 in mice by a single intravenous injection of $1\times10^9$ pfu Ade-COMP-Ang1. Throughout these experiments, we learned that long-term (~6 weeks) and sustained exposure to COMP-Ang1 produced long-lasting enlargement of postcapillary venules and terminal arterioles in the tracheal mucosa, while short-term (~2 weeks) and intermittent exposure to COMP-Ang1 produced reversible enlargements of these vessels. Similar to our results, another study found that long-term (4 weeks) sustained exposure to VEGF produced long-lasting acquired vascular remodeling in liver, while short-term (2 weeks) sustained exposure to VEGF produced reversible vascular remodeling (Dor et al., 2002, EMBO J. 21:1939-1947).

What are the major mechanisms and factors that produce long-lasting and reversible vascular remodeling? Is there a threshold stimulation of Tie2 by COMP-Ang1 in order to produce permanent enlargement? Our results indicate that auto-amplification of Tie2 expression by treatment with COMP-Ang1 above a certain dose and exposure period could be one of the mechanisms. Once Tie2 expression is activated by a long-term and excess exposure to COMP-Ang1, after discontinuation of COMP-Ang1, the subsequent activation of Tie2 may be achieved by endogenously circulating Ang1 or increased shear stress due to increased blood flow (Lee et al., 2003, Biochem Biophys Res Commun. 304:399-404). However, auto-amplification of Tie2 expression cannot be achieved below a certain dose and exposure period of COMP-Ang1, as evidenced by the experiments with intravenous administration of COMP-Ang1 recombinant protein. Therefore, the dose and the exposure period of COMP-Ang1 or VEGF should be considered in any therapeutic approaches where permanent vascular enlargements are needed to alleviate dysfunctions of ischemic tissues.

Tie1, an endothelial-specific receptor tyrosine kinase, shares a high degree of homology with Tie2. Although Tie1 was isolated over a decade ago (Partanen et al., 1992, Mol Cell Biol. 12:1698-707), no ligand had been found to activate it. Recently, Saharinen et al., demonstrated that COMP-Ang1 stimulated Tie1 phosphorylation in cultured endothelial cells (Saharinen et al., 2005, J. Cell Biol. 169:239-243). Moreover, they showed that COMP-Ang1-induced Tie1 activation was amplified via Tie2 and was more efficient than native Ang1- and Ang4-induced Tie1 activation. Thus, COMP-Ang1 and Ang1 are now known to be activating ligands for both Tie1 and Tie2. However, our data indicate that COMP-Ang1-induced vascular remodeling in adult tracheal vessels is mainly mediated through activation of Tie2, not by Tie1.

Although Ang1 induces vascular enlargement and has therapeutic benefits to ischemic tissues in several experimental animal models (Shyu et al., 1998, Circulation. 98:2081-2087; Chae et al., 2000, Arterioscler Thromb Vasc Biol. 20:2573-2578; Zhou et al., 2004, J Am Coll Cardiol. 44:897-903), little is known about whether the vascular enlargement is accompanied by enhanced blood flow. Our results showed that COMP-Ang1-induced vascular enlargement was accompanied with enhanced tissue blood flow in the trachea. Therefore, enhanced blood flow through arteriolar and venular enlargements induced by COMP-Ang1 could provide a great therapeutic benefit to ischemic peripheral tissues. In fact, Ang1-induced vessel enlargement is a unique characteristic among many growth factors. Our immunohistological examination of phosphohistone H3 revealed that COMP-Ang1-induced vascular enlargements were evidently the result of endothelial proliferation, which is consistent with a recent report (Baffert et al., 2004, Circ Res. 94:984-992). Thus, arteriolar and venular enlargements are achieved mainly by circumferential endothelial proliferation, which is a unique phenomenon and is different from multi-directional endothelial cell proliferation during vasculogenesis and angiogenesis. Moreover, our results revealed that different organs show different sensitivities to long-term and sustained COMP-Ang1. In fact, blood vessels in the skin, heart, adrenal cortex, and liver among other organs, are relatively sensitive to the COMP-Ang1-induced vascular enlargement. Therefore, COMP-Ang1 could provide a great therapeutic benefit to patients with delayed skin wound healing and ischemic heart diseases through its ability to promote vascular remodeling. Nevertheless, the mice treated with long-lasting and sustained COMP-Ang1 did not show any significant changes in body weight, systemic blood pressure, or heart rate. More detailed analysis will be necessary to clarify how it is possible that the mice with enlarged blood vessels caused by long-term and sustained COMP-Ang1 have a normal blood pressure and heart rate.

Ang1 is known to be a strong growth factor for pericyte recruitment to nascent endothelial cells during development (Suri et al., 1996, Cell. 87:1171-1180; Suri et al., 1998, Science. 282:468-471; Thurston et al., 1999, Science. 286:2511-2514). This Ang1-induced pericyte recruitment is related to the Ang1-induced anti-leakage effect on VEGF and pro-inflammatory stimuli (Thurston et al., 1999, Science. 286:2511-2514). However, our results show a lower number and poorer covering of pericytes in COMP-Ang1-induced enlarged postcapillary venules. In fact, in a mouse model that completely blocks pericyte recruitment to developing vessels by injection of antagonistic monoclonal antibody against platelet-derived growth factor receptor-β, Ang1 is able to restore a hierarchical architecture of growing blood vessels and rescues retinal edema and hemorrhage even in the absence of pericyte recruitment (Uemura et al., 2002. J Clin Invest. 110:1619-1628). Thus, COMP-Ang1 may be able to assemble endothelial cells in a frame of hierarchical architecture without pericyte recruitment in the COMP-Ang1-induced enlarged blood vessels.

In conclusion, long-lasting vascular enlargement and enhancement of blood flow can be achieved by long-term and sustained exposure to COMP-Ang1.

COMP-Ang1 Promotes Wound Healing through Enhanced Angiogenesis, Lymphangiogenesis and Blood flow in a Diabetic Mouse Model Healing of an adult cutaneous (skin) wound is a complex process integrating activities of different tissues and cell lineages (Martin, 1997, Science. 276:75-81). How contributing cell types behave during proliferation, migration, matrix synthesis, and contraction, as well as the growth factor and matrix signals present at a wound site in normal and pathologic conditions, has been extensively investigated. Of these, angiogenesis and lymphangiogenesis are crucial to the wound healing process (Tonnesen et al., 2000, J Invest Dermatol Symp Proc. 5:40-46; Hirakawa et al., 2004, J Dermatol Sci. 35:1-8). Signals mediated by vascular endothelial growth factor (VEGF) and angiopoietin have been implicated in control and regulation of angiogenesis and lymphangiogenesis (Yancopoulos et al., 2000, Nature. 407:242-248; Tammela et al., 2005, Trends Cell Biol. 15:434-441).

Delayed skin wound healing is a serious complication in diabetes, which is mainly caused by microangiopathy and peripheral neuropathy accompanied by impaired cutaneous blood flow, hypoxia, accelerated inflammation, edema, and endothelial-neural dysfunction (The Diabetes Control and Complications Trial Study Group. 1993, New Engl J. Med. 329:977-986; Martin et al., 2003, Med Res Rev. 23:117-145; Laing et al., 1998, Am J. Surg. 176:11 S-19S; Reiber et al., 1999, Diabetes Care. 22:157-162). Moreover, expression of VEGF-A and Tie2, the Ang1 receptor, are markedly reduced in wounds of diabetic patients (Frank et al., 1995, J Biol. Chem. 26:12607-12613; Kampfer et al., 2001, Lab Invest. 81:361-373). Therefore, restoring structural and functional microvasculature by supplementary delivery of VEGF-A or Ang1 could be beneficial to promote wound healing in diabetic patients. In fact, recent reports (Galeano et al., 2003, Diabetologia. 46:546-555; Galiano et al., 2004, Am J Pathol. 164:1935-1947) indicated that topical application of VEGF-A promoted cutaneous wound healing through increased angiogenesis and by mobilizing and recruiting bone marrow-derived cells. However, exogenous application of VEGF-A often results in leaky, inflamed, and malformed vessels, which greatly compromises its therapeutic usefulness (Galeano et al., 2003, Diabetologia. 46:546-555; Galiano et al., 2004, Am J Pathol. 164:1935-1947; Thurston et al., 1999, Science. 286:2511-2514). In comparison, Ang1 is a unique and specific growth factor functioning to generate a stable and functional vasculature through the Tie2 and Tie1 receptors (Thurston et al., 1999, Science. 286:2511-2514; Davis et al., 1996, Cell. 87:1161-1169; Suri et al., 1996, Cell. 87:1171-1180; Cho et al., 2005, Circ Res. 97:86-94; Saharinen et al., 2005, J Cell Biol. 169:239-243). We have recently developed a soluble, stable and potent Ang1 variant, COMP-Ang1 (Cho et al., 2004. Proc Natl Acad Sci. USA 101:5547-5552). To create this protein, we replaced the amino-terminal portion of Ang1 with the short coiled-coil domain of cartilage oligomeric matrix protein (COMP). COMP-Ang1 is more potent than native Ang1 in phosphorylating the Tie2 receptor and signaling via Akt in primary cultured endothelial cells (Cho et al., 2004. Proc Natl Acad Sci. USA 101:5547-5552). Furthermore, long-term and sustained treatment of COMP-Ang1 could produce long-lasting and stable vascular enlargement and increased blood flow (Cho et al., 2005, Circ Res. 97:86-94).

In the present application, we determined the effectiveness of COMP-Ang1 on promotion of the healing process in cutaneous wounds of normal and diabetic mice. In addition, because Ang1-induced angiogenesis appears to require generation of nitric oxide by activated endothelial nitric oxide synthase (eNOS) of the endothelium (Babaei et al., 2003. Am J Pathol. 162:1927-1936), we asked whether eNOS or inducible nitric oxide synthase (iNOS) participated in COMP-Ang1-induced accelerated wound healing using eNOS (−/−) and iNOS (−/−) mice. Our results indicate that COMP-Ang1 can promote wound healing in the normal and diabetic mice with enhanced angiogenesis, lymphangiogenesis and blood flow. The COMP-Ang1-induced promotion of wound closure and angiogenesis was not dependent on eNOS and iNOS.

COMP-Ang1 Attenuates Ventricular Remodeling, Induces Angiogenesis, and Restores Ventricular Functions in a Late-Reperfused Transmural Myocardiac Infarction (LMI)' Rat Model The present inventors have also demonstrated that COMP-Ang1 markedly attenuates left ventricular remodeling in a rat model of myocardiac infarction. These findings indicate that COMP-Ang1 is an effective molecule for therapeutic angiogenesis of the ischemic heart. See Example 4.

EXAMPLES

Example 1

Materials and Methods

Example 1.1

Generation of COMP-Ang1 Recombinant Protein and Ade-COMP-Ang1

Recombinant Chinese hamster ovary (rCHO) cells expressing COMP-Ang1 (CA1-2; production rate, ~30 mg/L) were established as previously described (Hwang et al., 2005, Protein Express Purif. 39:175-183). Recombinant adenovirus expressing COMP-Ang1 or LacZ was constructed using the pAdEasy™ vector system (Qbiogene).

Example 1.2

Animals, Treatment and Measurement of Blood Pressure and Heart Rate

Specific Pathogen-free FVB/N mice and Tie2-GFP transgenic mice (FVB/N) (Schlaeger et al., 1997, Proc Natl Acad Sci USA. 94:3058-3063) were purchased from Jackson Laboratory and bred in our pathogen-free animal facility. Male mice 8-10 weeks old were used for this study. Animal care and experimental procedures were performed under approval from the Animal Care Committees of KAIST. For protein treatment, 200 μg of COMP-Ang1 recombinant protein or BSA dissolved in 50 μL of sterile 0.9% NaCl was injected daily through the tail vein for 2 weeks. For adenoviral treatment, the indicated amount of Ade-COMP-Ang1, Ade-LacZ, or Ade-sTie2-Fc (soluble Tie2 receptor adenovirus construct) (generous gift from Dr. Gavin Thurston and Dr. Ella Ioffe at Regeneron Pharmaceuticals) diluted in 50 μL of sterile 0.9% NaCl was injected intravenously through the tail vein. Systemic blood pressure and heart rate were measured under anesthesia.

Example 1.3

Enzyme-Linked Immunosorbent Assay (ELISA)

Approximately 50 μL of blood was obtained from the tail vein into a heparinized capillary tube at the indicated times. ELISA was adopted for precise detection of COMP-Ang1 in plasma Example 1.4

Immunohistochemical Staining

Mice were anesthetized, perfused with 1% paraformaldehyde in PBS, and several organs including tracheas were removed. Tracheas and ear skins were immunostained as whole mounts, while other organs were immunostained as sections. Signals were visualized, and digital images were obtained with a Zeiss Apotome microscope and a Zeiss LSM 510 confocal microscope.

Example 1.5

Measurement of Tracheal Tissue Blood Flow

After the mice were anesthetized, a type N flowprobe (Transonic Systems, Inc. Ithaca, N.Y., USA) was placed on tracheal wall along second, third, and fourth cartilage rings without applying pressure, as this would occlude the vessels and reduce perfusion in the area of interest. The flowprobe was kept in place on the position of the highest sensitivity by a micromanipulator and connected to a laser-Doppler flowmeter (model BLF21; Transonic Systems, Inc), which can measure microcirculation in 1 $mm^3$ of tissue for real-time assessment of perfusion (ml/min/100 g of tissue).

Example 1.6

Morphometric Measurements and Statistics

Morphometric measurements of the vessel diameters and area densities in mouse trachea were made as previously described (Baluk et al., 2004, Am J Physiol Lung Cell Mol Physiol. 287:L307-L317). For each trachea, the numbers of PH3 immunopositive endothelial cells, PECAM-1-immunopositive blood vessels, and desmin/NG2-immunopositive pericytes were measured in 5 regions, each 0.21 $mm^2$ in area. Values were expressed per $mm^2$. Values presented are mean±standard deviation (SD). Significance of differences between mean was tested by analysis of variance followed by the Student-Newman-Keuls test. Statistical significance was set at $P<0.05$.

Example 1.7

Figure 22:
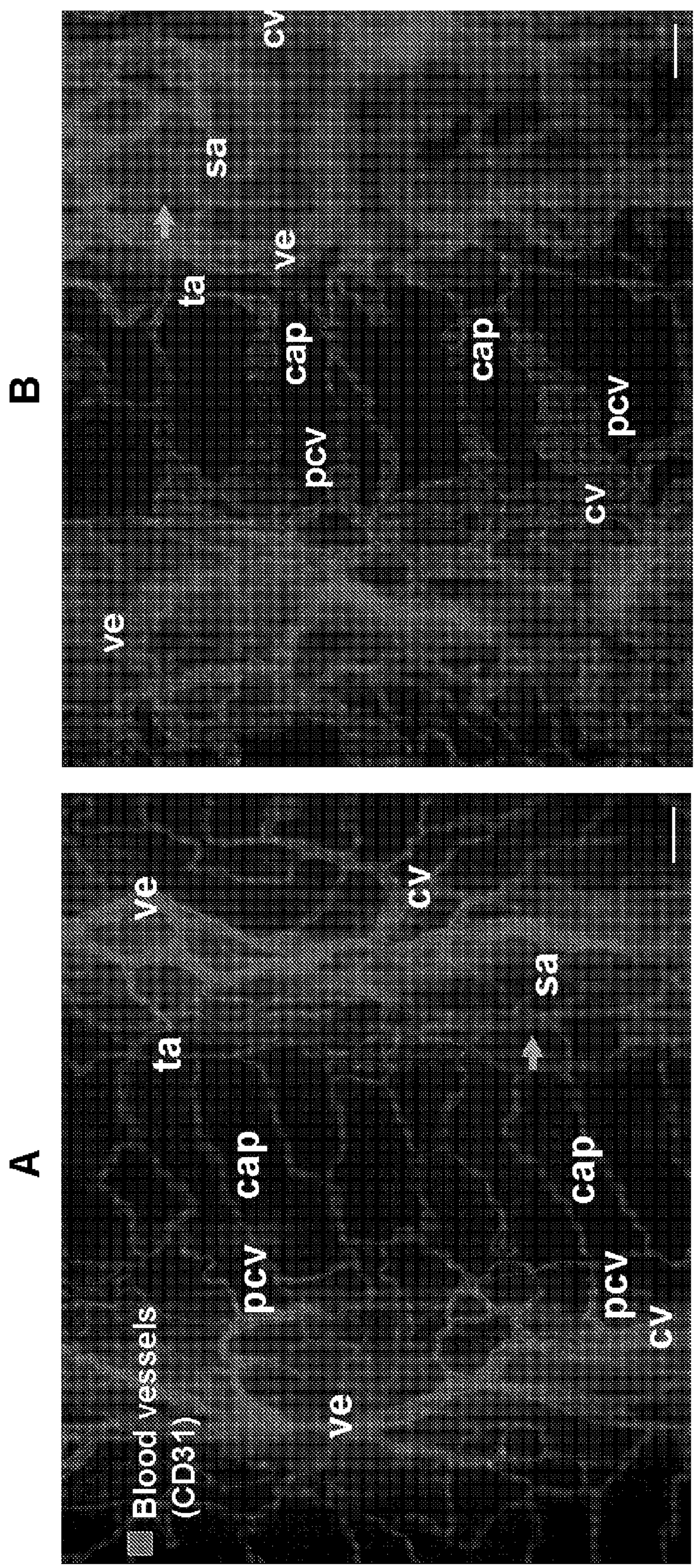
FIGS. 22A-22B show the effect of systemic COMP-Ang1 protein treatment on blood vessels in mouse tracheal mucosa. FVB/N mice were treated with daily injection of 200 μg of BSA (A) or 200 μg of COMP-Ang1 recombinant protein (B) for 14 days. Blood vessels in tracheal whole mounts were visualized with PECAM-1 (CD31) immunostaining (red). Six segments of the microvascular hierarchy are evident: segmental arteriole (sa, arrows), terminal arteriole (ta), capillary (cap), postcapillary venule (pcv), collecting venule (cv), venule (ve). Of these, postcapillary venules and the venous ends of capillaries were the most enlarged after treatment by COMP-Ang1. The results from 4 experiments were similar. Scale bar=50 μm.

Systemic Adenoviral COMP-Ang1 Produces Differential Enlargements of Blood Vessels in Mouse Tracheal Mucosa For in vivo treatments with COMP-Ang1, we developed a stable Chinese hamster ovary (CHO) cell line (CA1-2) which produces COMP-Ang1 at ~30 mg/L. The potency, solubility, oligomerization status, and stability of the COMP-Ang1 produced from CA1-2 are similar to those of COMP-Ang1 produced from COS-7 cells transiently transfected with plasmid vector containing the COMP-Ang1 gene (Cho et al., 2004, Proc Natl Acad Sci USA. 101:5547-52) (data not shown). Adult mice were treated with a daily intravenous injection of 200 μg of COMP-Ang1 recombinant protein or bovine serum albumin (BSA) through the tail vein for 2 weeks, then blood vessels in the tracheal mucosa were visualized with platelet/endothelial cell adhesion molecule-1 (PECAM-1) immunostaining (FIG. 22). Six segments of the microvasculature were distinguished by their position in the vascular hierarchy and differences in endothelial cell morphology (McDonald et al., 1994, Am J Physiol. 266:L61-L83). Enlargement of tracheal blood vessels was found in mice that received COMP-Ang1 in the following descending order of effect: postcapillary venules>capillaries>collecting venules>venules>terminal arterioles (FIG. 22B). No significant change was noted in segmental arterioles. These phenomena were observed in all individuals of several mouse strains studied (FVB/N, C57BL/6, BALB/c, BALB/c-nu, C3H/HeJ). No changes in the sizes or shape of tracheal blood vessels were found in mice that received BSA.

Example 1.8

Figure 23:
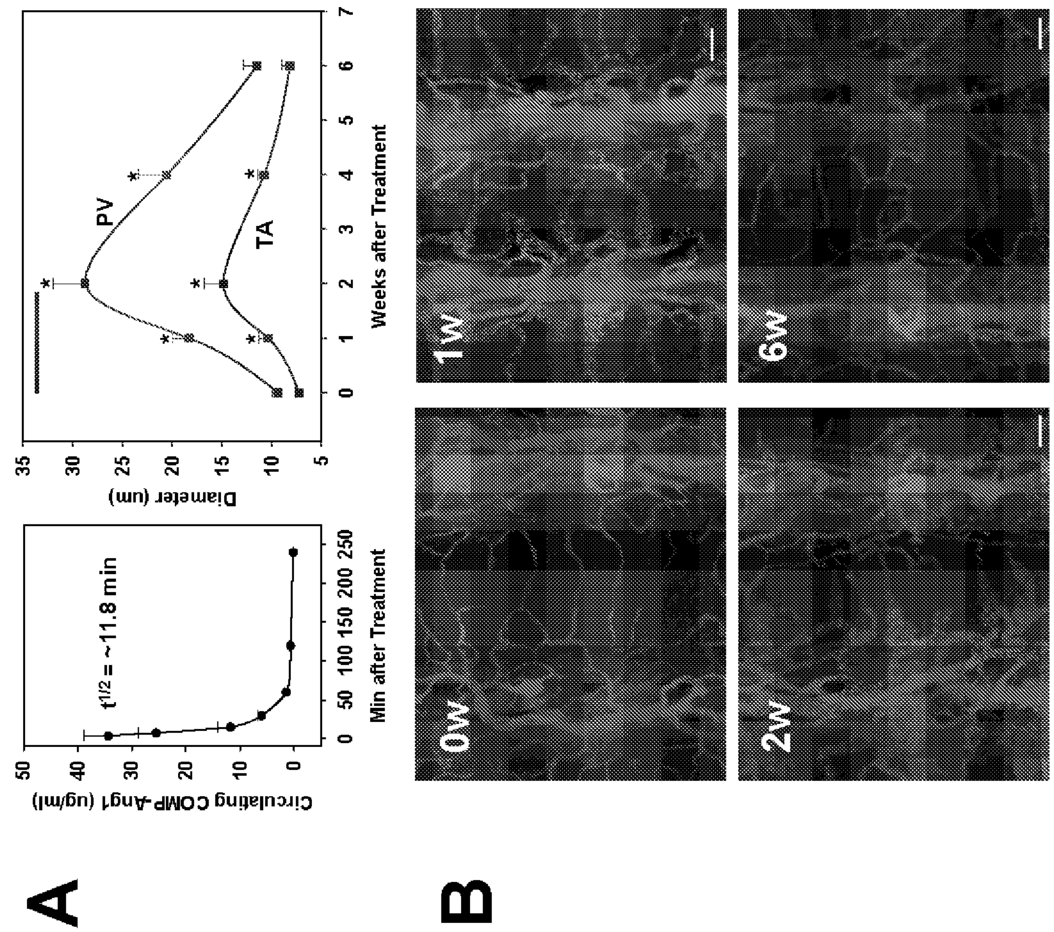
FIGS. 23A-23B show the effects of systemic COMP-Ang1 protein treatment on postcapillary venules and terminal arterioles. FVB/N mice were treated by daily injection of COMP-Ang1 recombinant protein (200 μg) for 14 days (A, black bar). At the indicated times, tracheal vessels were visualized with PECAM-1 immunostaining (B, red). The diameter of postcapillary venules and terminal arterioles are shown (A, right panel). Circulating plasma levels of COMP-Ang1 were measured by ELISA after a single injection of COMP-Ang1 recombinant protein (200 μg/mouse) (A, left panel). Diameters of 35-40 postcapillary venules (PV)/5 fields (brown curve) and 10-12 terminal arterioles (TA)/10 fields (blue curve) were measured at the edge of cartilage rings in each mouse. Values are mean±SD from 4-5 mice. *, $P<0.05$ versus control period. COMP-Ang1-induced enlargement of postcapillary venules, collecting venules, venous ends of capillaries, venules, and terminal arterioles for up to 2 weeks, then the enlarged blood vessels returned gradually to normal after discontinuation of the COMP-Ang1 treatment. Scale bar=50 μm.

Short-Term and Intermittent Circulating Comp-Ang1 Induces Reversible Enlargement of Postcapillary Venules and Arterioles in Tracheal Vessels When 200 μg of COMP-Ang1 recombinant protein was injected intravenously into adult male mice, circulating COMP-Ang1 level peaked immediately after injection (~3.75 min), then declined, and returned almost to the control level 3-4 hrs after treatment (FIG. 23A). The half-life ($t^{1/2}$) of circulating COMP-Ang1 was 11.8 min. Daily intravenous injection of 200 μg of COMP-Ang1 for 1 week in mice produced approximately a 2.0-fold enlargement of postcapillary venules and a 1.4-fold enlargement of terminal arterioles in the trachea (FIG. 23). The COMP-Ang1-induced enlargement of postcapillary venules, collecting venules, venous end of capillaries, venules, and terminal arterioles were further increased up to 2 weeks upon continuation of daily injection of COMP-Ang1 for up to 2 weeks. However, COMP-Ang1-induced enlarged blood vessels returned gradually to normal after discontinuation of the COMP-Ang1 treatment (FIG. 23). One month after discontinuation of the COMP-Ang1 treatment, a second round of treatment with a daily intravenous injection of 200 μg of COMP-Ang1 for 2 weeks induced similar enlargements of tracheal vessels, again in a reversible manner (data not shown). In comparison, the diameters of tracheal vessels were indistinguishable between the control and experimental periods in tracheal vessels of mice treated with BSA (data not shown). These results indicate that short-term spikes of circulating COMP-Ang1 induce reversible enlargement of some tracheal vessels.

Example 1.9

Figure 24:
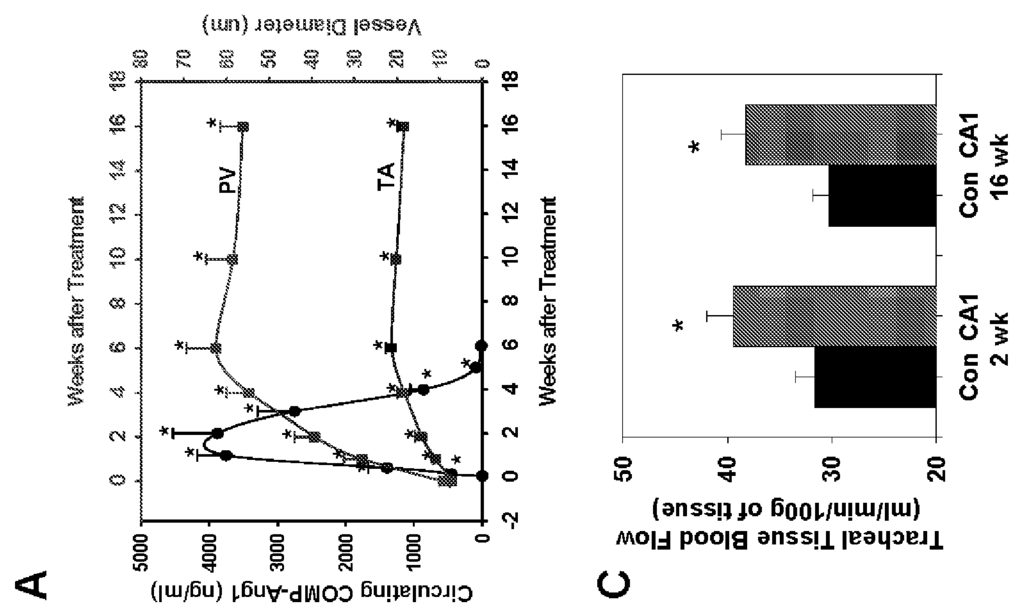
FIGS. 24A-24E show the effects of adenoviral COMP-Ang1 on postcapillary venules and terminal arterioles, and blood flow.
Figure 24:
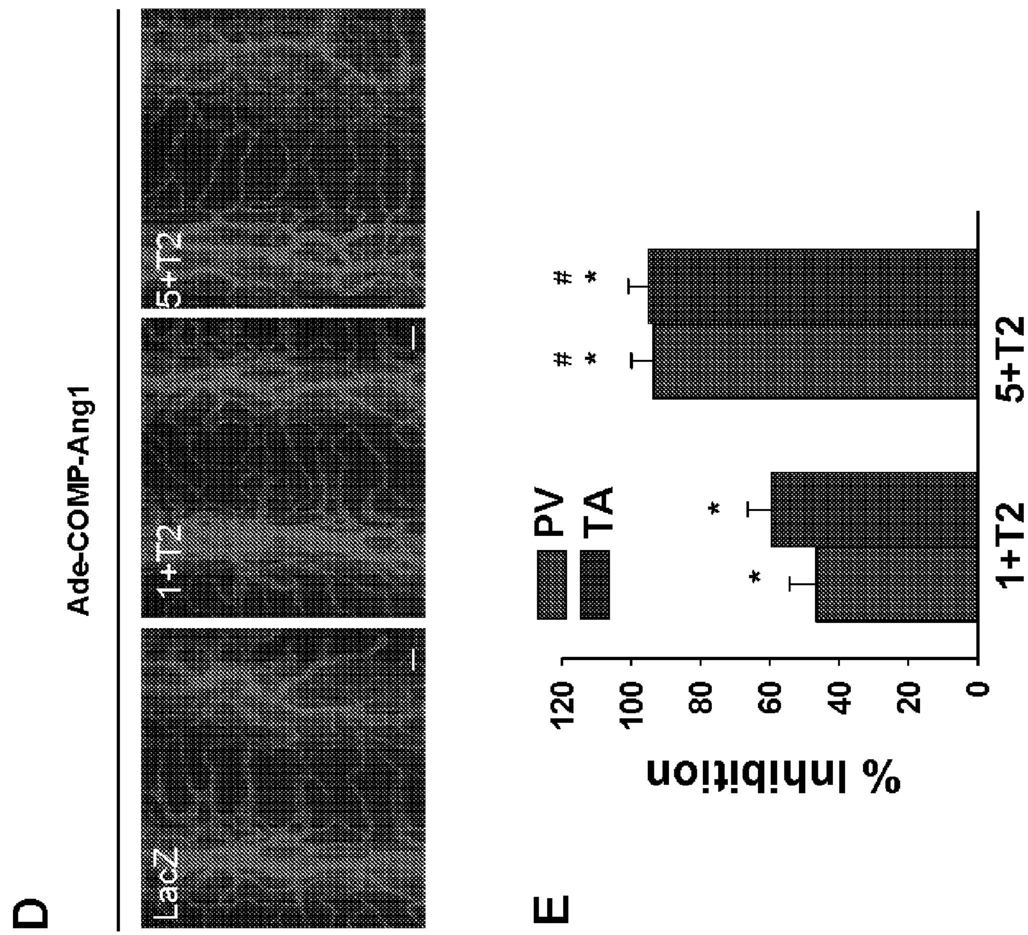

Long-Term and Sustained Circulating COMP-Ang1 Induces Long-Lasting Enlargement of Postcapillary Venules and Terminal Arterioles in Tracheal Vessels As an alternative method for systemic treatment with COMP-Ang1, an adenoviral vector encoding the COMP-Ang1 gene (Ade-COMP-Ang1) was also developed. As a control, an adenoviral vector encoding the LacZ gene (Ade-LacZ) was developed. The potency, solubility, oligomerization status, and stability of the COMP-Ang1 produced from HEK293 cells transduced with Ade-COMP-Ang1 are similar to that of COMP-Ang1 produced from COS-7 cells transiently transfected with plasmid vector containing the COMP-Ang1 gene (Cho et al., 2004, *Proc Natl Acad Sci USA*. 101:5547-52) (data not shown). Adult mice were treated with $1\times10^9$ pfu Ade-COMP-Ang1 or Ade-LacZ. At multiple times over a period of 16 weeks, circulating plasma COMP-Ang1 levels were measured, and blood vessels in tracheal mucosa were visualized with PECAM-1 immunostaining (FIG. 24). Circulating COMP-Ang1 increased as early as 12 hrs after treatment, peaked at 1-2 weeks, declined gradually thereafter, and returned to control levels at 6 weeks after treatment (FIG. 24A). The peak concentrations of circulating COMP-Ang1 were approximately 3.5-4.5 μg. Significant enlargement of postcapillary venules, capillaries (distinctively, only the venous end of capillaries was enlarged), collecting venules, and terminal arterioles but not segmental arterioles, was noticeable at one week after the Ade-COMP-Ang1 treatment (FIG. 24B). The vascular enlargements induced by Ade-COMP-Ang1 increased further for up to six weeks and then reached a plateau (FIGS. 24A and 24B). For example, the diameter of postcapillary venules increased 4.3-fold at 2 weeks, 6.0-fold at 4 weeks, and 6.8-fold at 6 weeks (FIG. 24A). The enlargement of terminal arterioles was also significant beginning at one week after the treatment and increased in a time-dependent manner. However, the increase in diameter in terminal arterioles was less than in postcapillary venules (FIGS. 24A and 24B). Importantly, the size of Ade-COMP-Ang1-induced enlarged blood vessels did not significantly decrease for as long as 16 weeks after the treatment, although circulating COMP-Ang1 returned to the control level at 6 weeks after the treatment (FIG. 24A). In comparison, diameters of tracheal vessels in mice treated with Ade-LacZ were indistinguishable between the control and experimental periods (data not shown). Using a laser-Doppler flowmeter, tracheal tissue blood flows were measured at 2 weeks (the peak level of circulating COMP-Ang1) and 16 weeks (undetectable level of circulating COMP-Ang1) after Ade-LacZ or Ade-COMP-Ang1 treatment. At 2 weeks, tracheal tissue blood flow was increased approximately 25% in the mice treated with Ade-COMP-Ang1 compared to the mice treated with Ade-LacZ (FIG. 24C). At 16 weeks, importantly, increased tracheal tissue blood flow by Ade-COMP-Ang1 was not significantly changed (FIG. 24C). These results indicate that long term and sustained circulating COMP-Ang1 treatment induces long-lasting enlargement of tracheal blood vessels with long-lasting enhancement of tissue blood flow in the adult mice.

Example 1.10

Tie2 Activation is Involved in COMP-Ang1-Induced Vascular Remodeling

To determine the involvement of Tie2 activation in COMP-Ang1-induced vascular remodeling, the mice were pretreated with $1\times10^8$ pfu or $5\times10^8$ pfu Ade-sTie2-Fc at 24 hr prior to $1\times10^8$ pfu Ade-COMP-Ang1 treatment. Two weeks later, the diameters of postcapillary venules and terminal arterioles were measured. Pretreatment with $1\times10^8$ pfu or $5\times10^8$ pfu Ade-sTie2-Fc suppressed COMP-Ang1-induced vascular remodeling to the following extent: 46.5±7.7% or 93.5±6.4% in postcapillary venules and 59.7±6.6%, or 95.1±5.7% in terminal arterioles, respectively (FIGS. 24D and 24E). These data indicate that COMP-Ang1-induced vascular remodeling is mainly mediated through Tie2 activation in adult tracheal vessels.

Example 1.11

Figure 25:
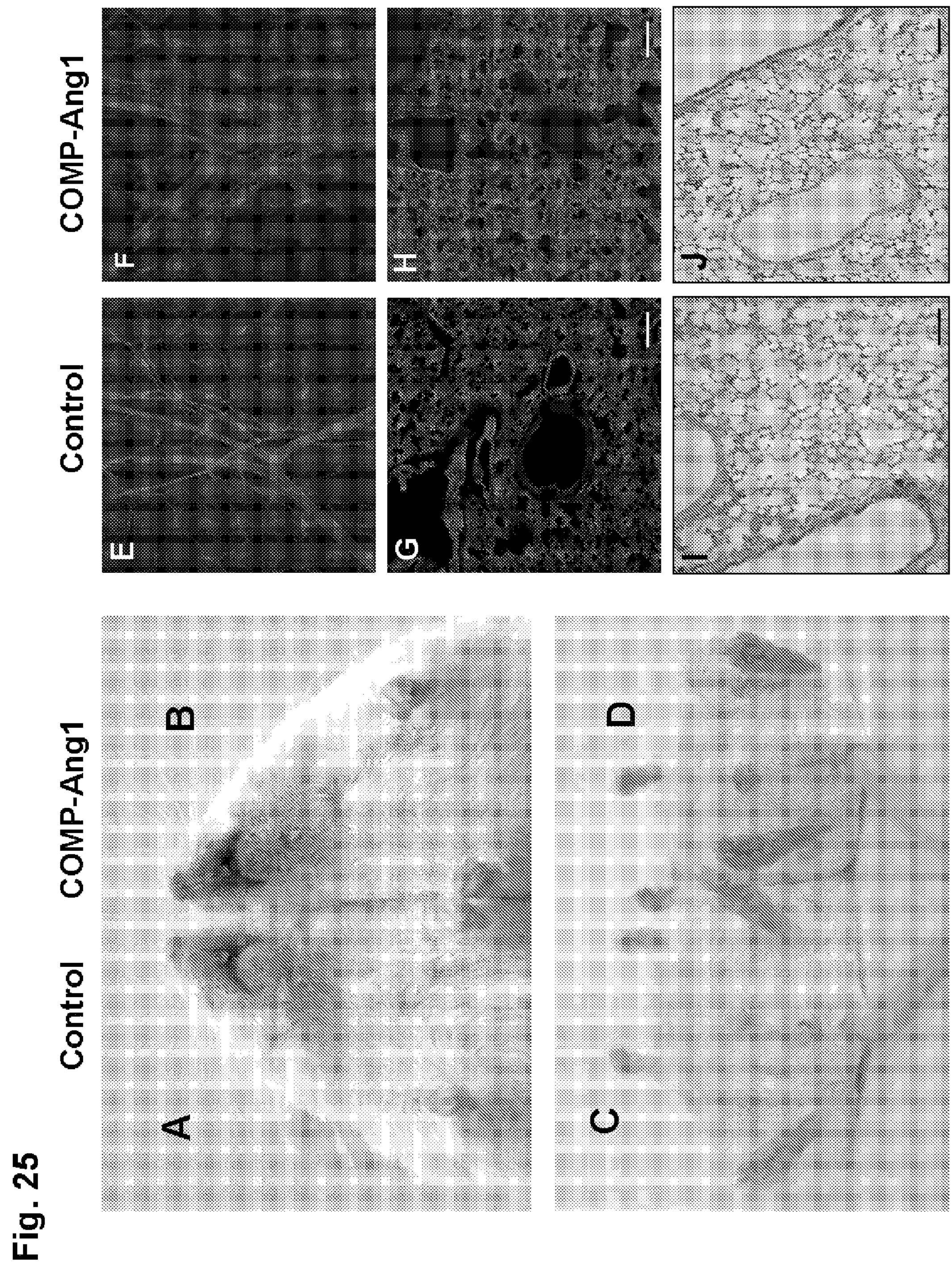
FIGS. 25A-25J show the effect of adenoviral COMP-Ang1 on skin color and vascular remodeling in ear skin and lung at 16 weeks after the treatment. FVB/n mice were treated with $1\times10^9$ pfu Ade-LacZ or Ade-COMP-Ang1. Sixteen weeks later, the skin color of the face, hands, soles, penis, and tail were photographed (A, B, C and D), blood vessels in ear skin (E and F) and lungs (G and H) were visualized with PECAM-1 (CD31) immunostaining (red), and sections of lungs were stained with H&E (I and J). The mice treated with Ade-COMP-Ang1 show overt skin redness, and have prominently enlarged blood vessels in the ear skin, and more dense PECAM-1 positive endothelial cells in the lung without overt histologic alteration compared to the mice treated with Ade-LacZ. The results from 4 experiments were similar. Scale bar=50 μm.
Figure 26:
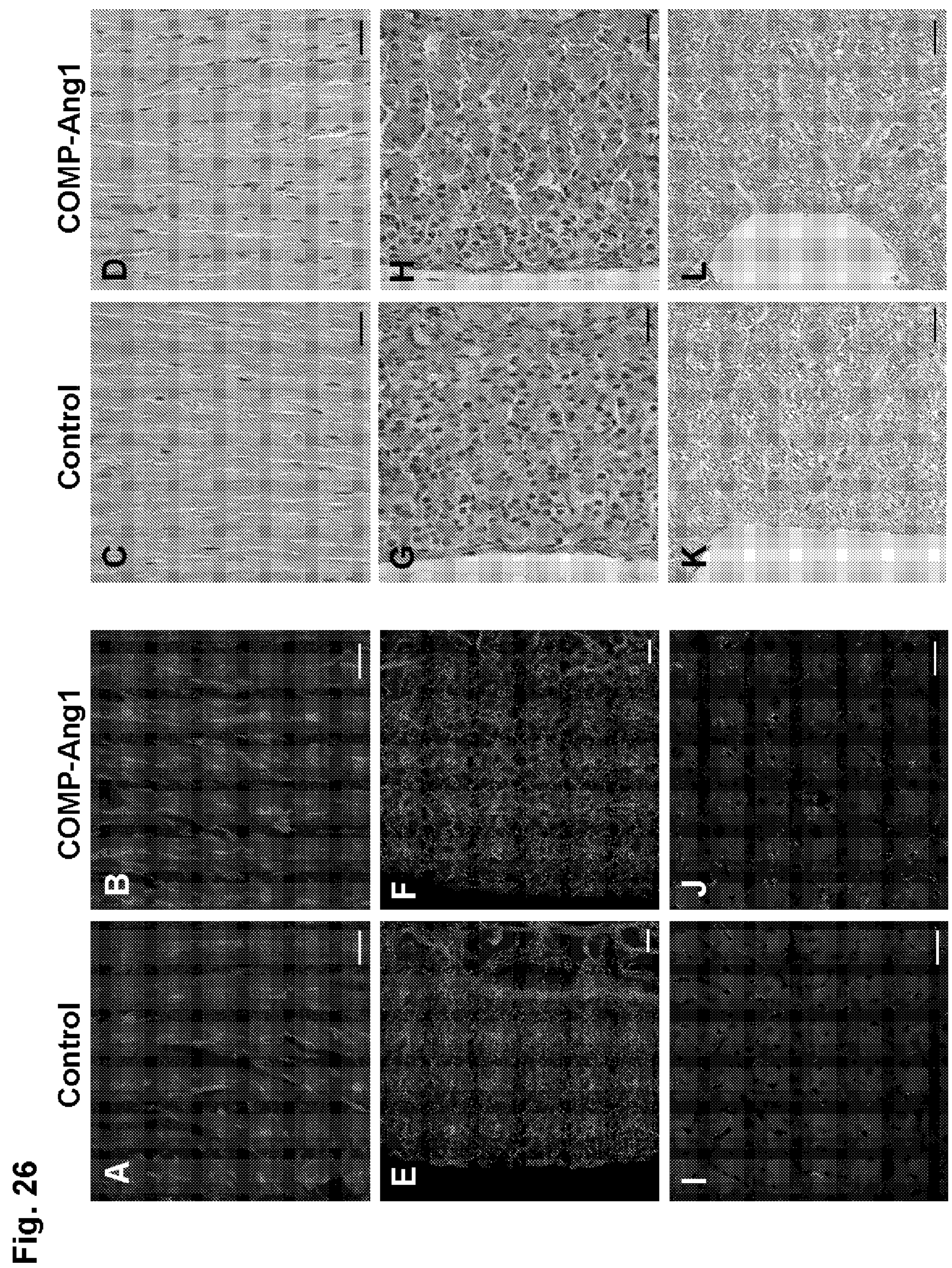
FIGS. 26A-26L show the effects of adenoviral COMP-Ang1 on vascular remodeling in heart, adrenal cortex, and liver at 16 weeks after the treatment. FVB/n mice were treated with $1\times10^9$ pfu Ade-LacZ or Ade-COMP-Ang1. Sixteen weeks later, blood vessels in heart (A, B, C, and D), adrenal cortex (E, F, G, and H) and liver (I, J, K, and L) were visualized with PECAM-1 (CD31) immunostaining (red), and the sections were stained with H&E. The mice treated with Ade-COMP-Ang1 have enlarged capillaries in the heart and adrenal cortex and more PECAM-1 positive endothelial cells in the liver compared to the mice treated with Ade-LacZ. The results from 4 experiments were similar. Scale bar=25 μm.

Long-Term and Sustained Circulating Comp-Ang1 Induces Various Vascular Remodeling in Different Organs Both mice treated with Ade-LacZ ($1\times10^9$ pfu) and those treated with Ade-COMP-Ang1 ($1\times10^9$ pfu) appeared generally healthy, as they gained weight normally. However, the skin of mice treated with Ade-COMP-Ang1 appeared strikingly redder than the skin of mice treated with Ade-LacZ from, beginning at 10-14 days after the treatment. The Ade-COMP-Ang1-induced skin redness persisted for as long as 16 weeks after the treatment (FIG. 25). Sixteen weeks after the treatment, skin color in hair-sparse portions such as the face, hands, soles, penis, and tail of mice treated with Ade-COMP-Ang1 were distinctly redder than those of mice treated with Ade-LacZ. Blood vessels of the ear and capillaries of the heart, adrenal cortex, and liver of the mice treated with Ade-COMP-Ang1 were enlarged (FIGS. 25 and 26). More PECAM-1 positive endothelial cells were present in the lung, heart, liver, and renal medulla of mice treated with Ade-COMP-Ang1 compared to the mice treated with Ade-LacZ (FIGS. 25 and 26). However, blood vessels of the renal cortex, including glomeruli, and intestinal villi of the mice treated with Ade-COMP-Ang1 and the mice treated with Ade-LacZ were indistinguishable. In addition, the body weights, systemic blood pressures, and heart rates of the two groups of mice were indistinguishable. These results indicate that long term and sustained circulating COMP-Ang1 treatment induces long-lasting tissue-specific vascular remodeling in different blood vessels without notable changes in systemic blood pressure and heart rate (Table 1).

TABLE 1

Comparison of hemodynamic parameters between control- and COMP-Ang1-treated mice.

| | Control | COMP-Ang1 | Significance |
|---|---|---|---|
| Body weight (g) | 30.5 ± 1.9 | 29.0 ± 1.1 | NS |
| SBP (mmHg) | 87.8 ± 5.8 | 90.7 ± 3.6 | NS |
| DBP (mmHg) | 51.7 ± 4.9 | 59.2 ± 4.2 | NS |
| MAP (mmHg) | 70.1 ± 6.8 | 74.1 ± 3.2 | NS |
| Heart rate (bpm) | 190 ± 16 | 212 ± 1.0 | NS |

FVB/N mice were treated with $1\times10^9$ pfu Ade-LacZ (n = 5) or Ade-COMP-Ang1 (n = 5). Sixteen weeks later, mice were anesthetized, and their systolic blood pressure (SBP), diastolic blood pressure (DBP), mean arterial pressure (MAP) and heart rate were measured. Values are mean ± SD from 5 mice.

NS, not significant.

Example 1.12

Figure 27:
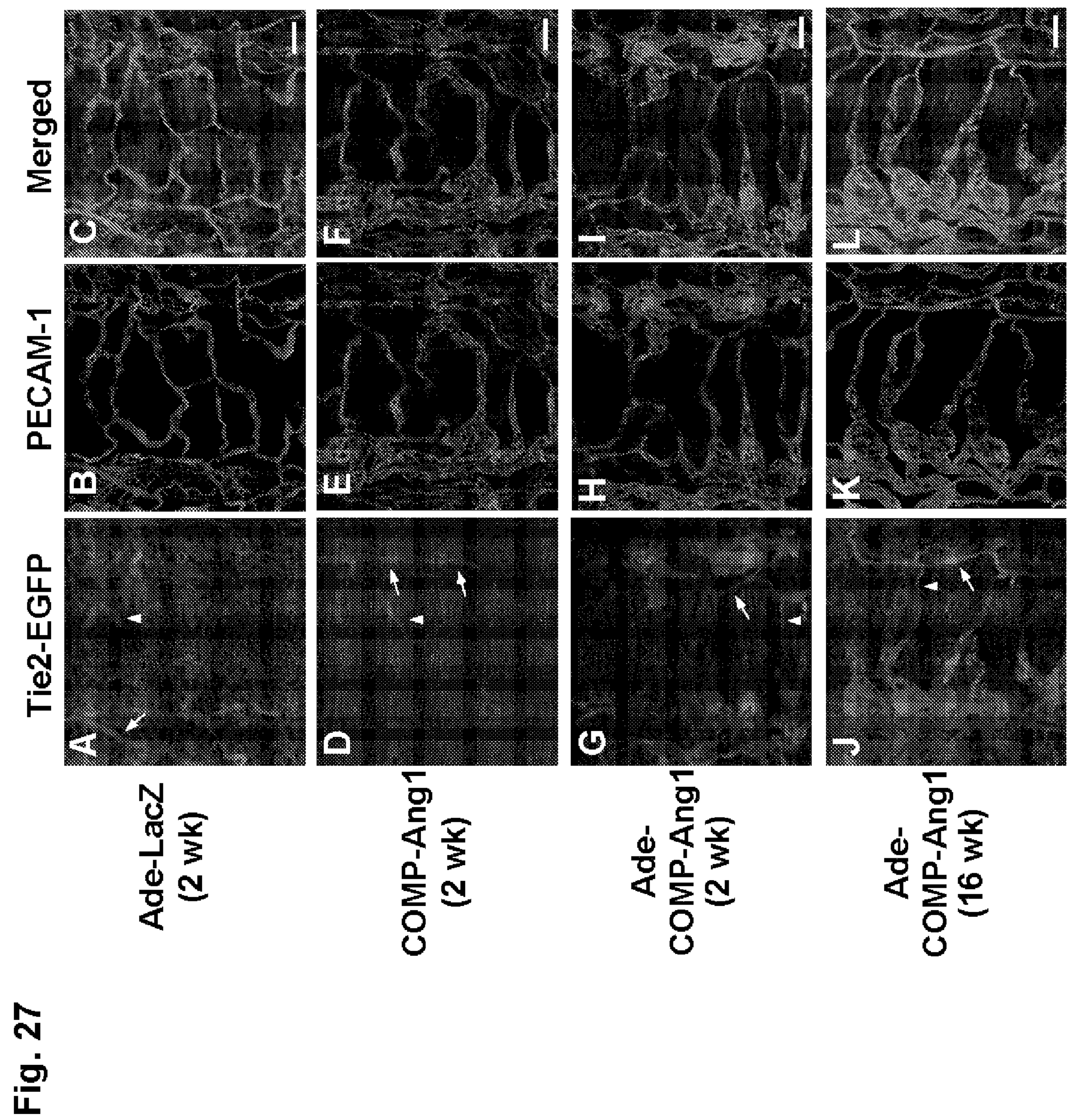
FIGS. 27A-27L show the induction of Tie2 expression in COMP-Ang1-induced vascular remodeling. Tie2-GFP transgenic mice (10 weeks old) were treated with daily injections of 200 μg of COMP-Ang1 recombinant protein (COMP-Ang1) for 2 weeks (D, E, F) or a single injection of $1\times10^9$ pfu Ade-LacZ (A, B, C) or Ade-COMP-Ang1 (G, H, I, J, K, L). At 2 and 16 weeks after the beginning of the treatments, Tie2 expression in tracheal vessels was visualized by GFP expression (green) and PECAM-1 immunostaining (red), and the images were merged. The results from 4 experiments were similar. Arrowhead, terminal arterioles; arrow, precapillary arterioles. Scale bar=50 μm.

Induction of Tie2 could be Involved in Permanent Changes of COMP-Ang1-Induced Vascular Remodeling Based on these observations, we asked whether Tie2 expression was more abundant in postcapillary venules than terminal arterioles in mouse trachea. Therefore, we examined the extent of Tie2 expression using transgenic mice with Tie2 promoter-driven green fluorescent protein (GFP) (Schlaeger et al., 1997, Proc Natl Acad Sci USA. 94:3058-3063). In the tracheal mucosa of adult mice, Tie2 expression was not detectable in most endothelial cells of postcapillary venules, while it was moderately expressed in endothelial cells of terminal and precapillary arterioles of tracheal vessels (FIG. 27). Thus, differential enlargement of tracheal vessels upon COMP-Ang1 stimulation is not dependent on the extent of Tie2 expression. However, Tie2 expression was markedly increased in endothelial cells of collecting venules, venules, postcapillary venules, and capillaries at 2 weeks after the Ade-COMP-Ang1 treatment (FIG. 27), which is somewhat consistent with a recent report with Ade-Ang1 (Baffert et al., 2004, Circ Res. 94:984-992). Tie2 expression was further increased in endothelial cells of the same vessels at 16 weeks after the Ade-COMP-Ang1 treatment (FIG. 27). In contrast, Tie2 expression was not changed in any endothelial cells of enlarged tracheal vessels at 2 weeks after the recombinant COMP-Ang1 protein treatment (FIG. 27). Area densities of Tie2 expression in a given microscopic field area (0.22 $mm^2$) for arterioles, capillaries and venules in tracheal mucosa, were 8.2±1.7, 2.8±0.4, and 3.3±0.6% respectively (mean±SD from 4 mice) after Ade-LacZ treatment (at 2 weeks), 7.6±1.9, 3.1±0.5, and 3.7±0.6% after COMP-Ang1 protein treatment (at 2 weeks), 11.3±2.2, 10.3±1.7, and 28.1±5.4% after Ade-COMP treatment (at 2 weeks), and 13.3±2.7, 18.2±3.5, and 47.7±7.2 after Ade-COMP treatment (at 16 weeks). In addition, Tie2 expression was notably higher in the enlarged veins of abdominal skin and the sinusoidal capillaries in the liver of the mice treated with Ade-COMP-Ang1 than the mice treated with Ade-LacZ at 16 weeks after the treatment. Thus, Tie2 expression in venular and capillary endothelial cells could be induced with long-term and sustained Tie2 stimulation induced by Ade-COMP-Ang1, but not with short-term spiked Tie2 stimulation induced by recombinant COMP-Ang1 protein.

Example 1.13

Figure 28:
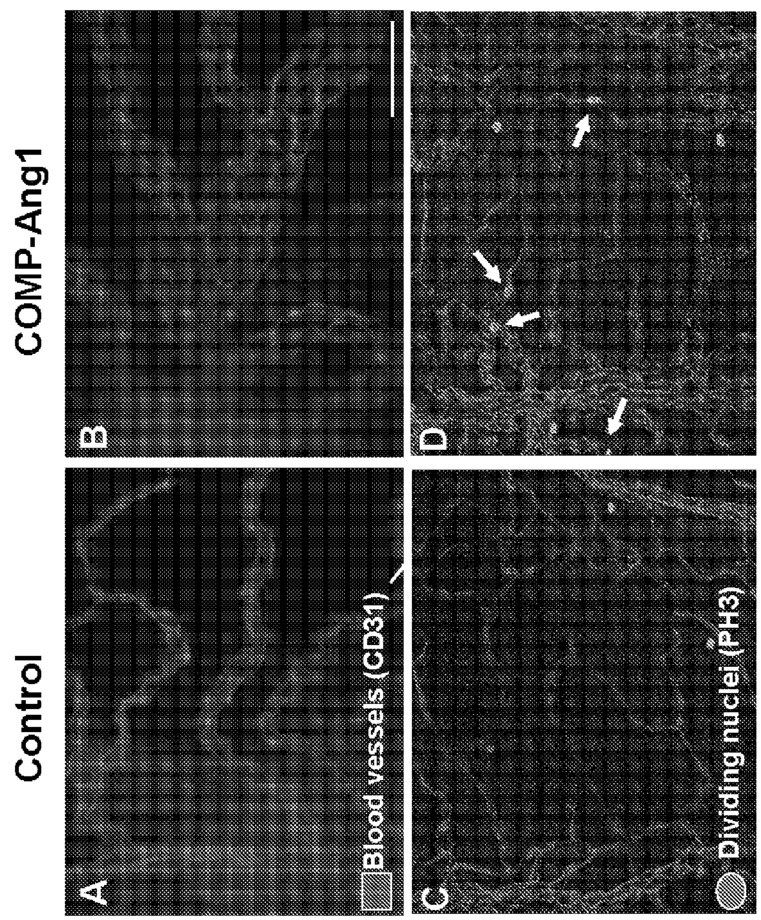
FIGS. 28A-28I show the increased number of dividing endothelial cells during COMP-Ang1-induced enlargement. FVB/N mice were treated with $1\times10^9$ pfu Ade-LacZ (control, A, C E, and G) or Ade-COMP-Ang1 (COMP-Ang1, B, D, F and H). Four days (C and D), 2 weeks (E and F) and 16 weeks (G and H) later, tracheal vessels were visualized with PECAM-1 (CD31) immunostaining (red) and phosphohistone H3 (PH3) immunostaining (green). (F) Arrow, PH3 immunopositive endothelial cells; white square, PH3 immunopositive endothelial cells in postcapillary venule at higher magnification. Scale bar=50 μm. (I) Number of PH3 immunopositive endothelial cells in a given 0.21 $mm^2$ area. Bars represent mean±SD from 4 mice. Con, control; CA1, COMP-Ang1. *, $P<0.05$ versus Con.
Figure 28:
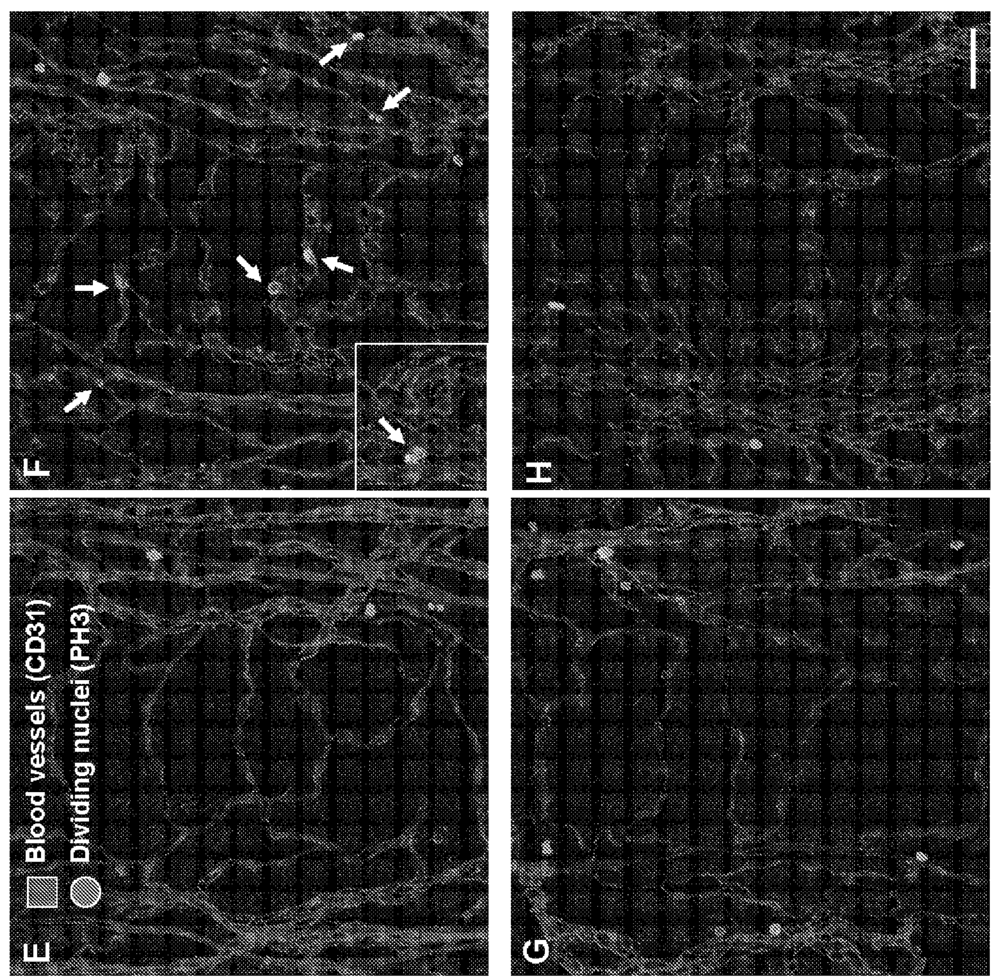
Figure 28:
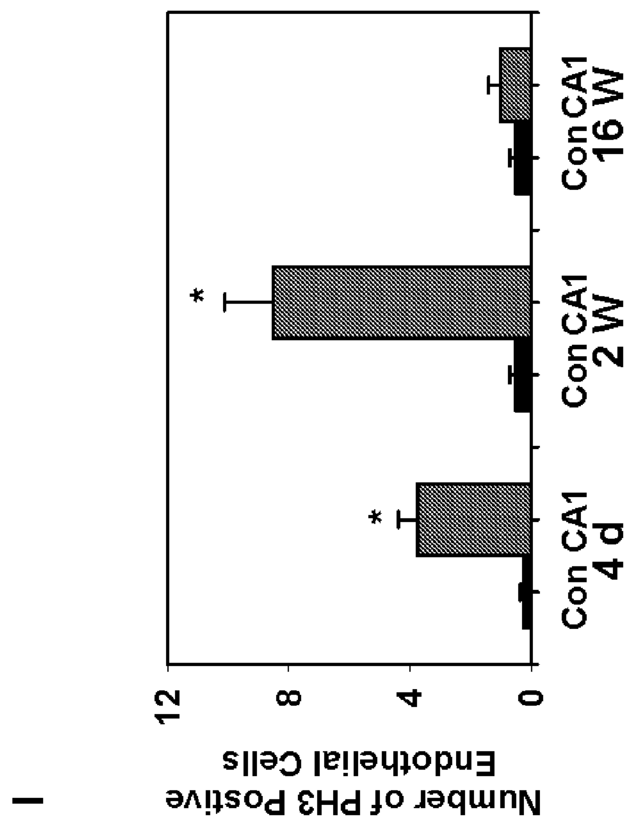

COMP-Ang1-Induced Vascular Enlargement could Result from Circumferential Endothelial Cell Proliferation COMP-Ang1-induced enlargement of blood venules appears to result from endothelial cell proliferation rather than vasodilation or endothelial cell hypertrophy because the endothelial cells were normal in size (FIGS. 28A and 28B). To test this possibility, we examined the number of phosphohistone H3 (nuclear protein of diving cell) positive endothelial cells by immunostaining. Numerous phosphohistone H3-positive immunostained endothelial cells were detected in various portions including postcapillary venules, capillaries, collecting venules, venules, and terminal arterioles of tracheal vessels at 4 days and 2 weeks after the Ade-COMP-Ang1 treatment (FIGS. 28D, 28F and 28I) or after recombinant COMP-Ang1 protein treatment (data not shown). However, almost no phosphohistone H3-positive endothelial cells were detected in any portion of tracheal vessels at 4 days, 2 and 16 weeks after the Ade-LacZ treatment and at 16 weeks after the Ade-COMP-Ang1 treatment (FIGS. 28C, 28E, 28G and 28I). These findings indicate that vascular enlargement induced by COMP-Ang1 is more likely to result from endothelial cell proliferation depending on the concentration of circulating COMP-Ang1 than from vasodilation or endothelial cell hypertrophy.

Example 1.14

Figure 29:
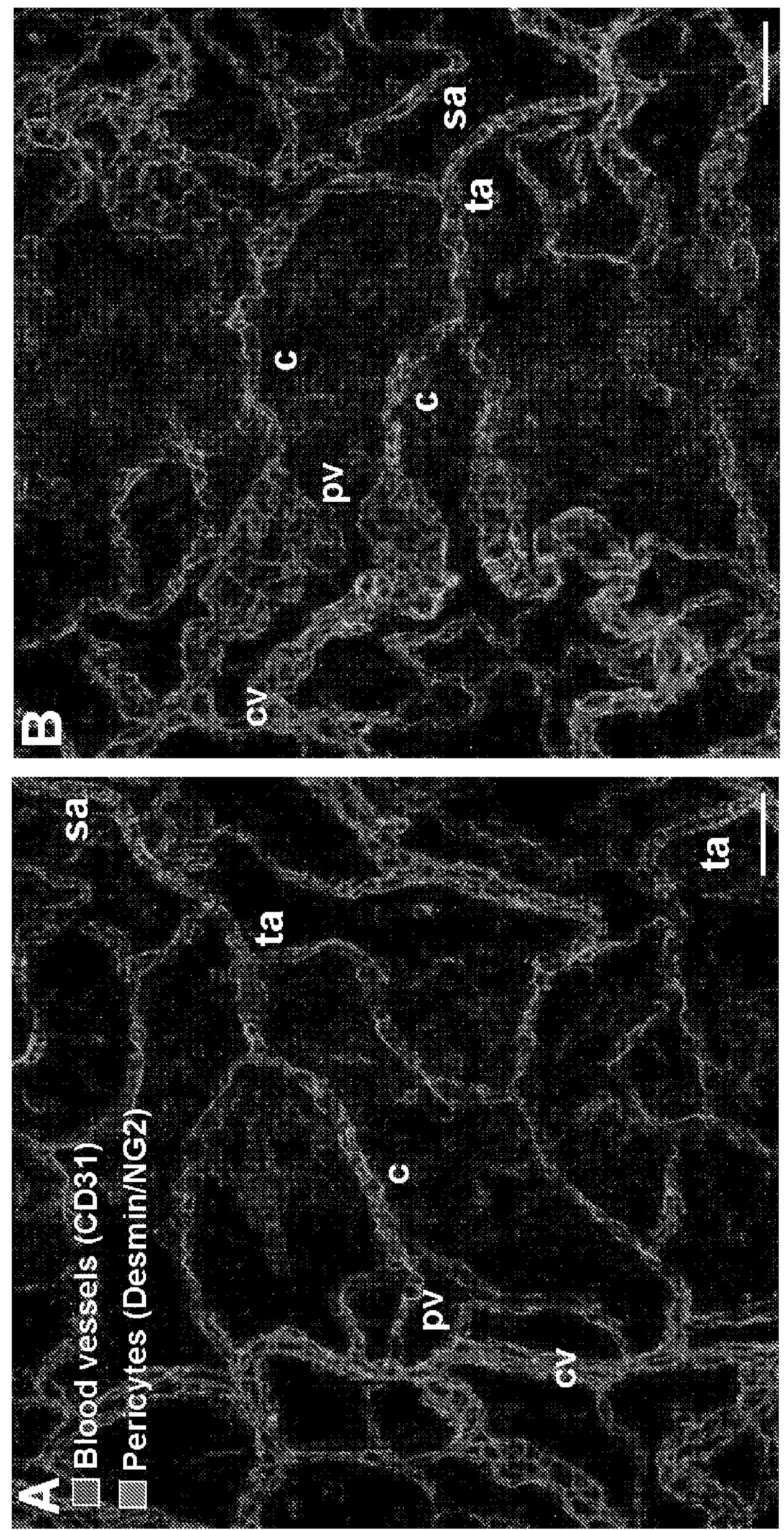
FIGS. 29A-29B show the interaction between endothelial cells and pericytes in COMP-Ang1-induced enlarged tracheal vessels. FVB/n mice were treated with $1\times10^9$ pfu Ade-COMP-Ang1 (B) or Ade-LacZ (A). Four weeks later, tracheal vessels were visualized with PECAM-1 (CD31) immunostaining (red), and pericytes were visualized with desmin/NG2 immunostaining (green). The results from 4 experiments were similar. Scale bar=50 μm.

COMP-Ang1-Induced Postcapillary Venule Enlargement is not Accompanied by Pericyte Recruitment Ang1 is known to be a strong growth factor for pericyte recruitment to nascent endothelial cells during vasculogenesis in physiologic and pathologic conditions (Suri et al., 1996, Cell. 87:1171-1180; Suri et al., 1998, Science. 282: 468-471; Thurston et al., 1999, Science. 286:2511-2514). Therefore, we examined the interaction between endothelial cells and pericytes in the enlarged blood vessels of the trachea by double immunostaining for endothelial cells and pericytes at 4 weeks after Ade-LacZ or Ade-COMP-Ang1 treatment. The interaction of endothelial cells and pericytes in most of tracheal blood vessels (except postcapillary venules) in mice that received Ade-COMP-Ang1 was similar that in mice that received Ade-LacZ (FIG. 29). Although less interaction of endothelial cells with pericytes was found on the enlarged postcapillary venules than elsewhere, the number of pericytes of the enlarged postcapillary venules was similar to the control postcapillary venules (FIG. 29). Thus, COMP-Ang1 did not promote pericyte recruitment to the COMP-Ang1-induced enlarged venules in the trachea.

Example 2

Generation of Ade-COMP-Ang1 and COMP-Ang1 Recombinant Protein

Recombinant adenovirus expressing COMP-Ang1 or bacterial β-galactosidase (hereafter β-gal) was constructed using the pAdEasy™ vector system (Qbiogene, Carlsbad, Calif.), as we previously described (Cho et al., 2005, Circ Res. 97:86-94). Recombinant Chinese hamster ovary cells expressing COMP-Ang1 (CA1-2) were established and recombinant COMP-Ang1 protein was prepared as previously described (Cho et al., 2005, Circ Res. 97:86-94).

Example 2.1

Animals, Wound Healing and Treatment

Specific pathogen-free FVB/N mice, diabetic C57BLKS/J-m+/+$Lepr^{db}$ (db/db) mice, C57BL/6J, and eNOS (−/−) mice and iNOS (−/−) (C57BL/6J genetic background) were purchased from Jackson Laboratory (Jackson Labs, Bar Harbor, Me.) and bred in our pathogen-free animal facility. 8-10-week old male mice were used for this study. Animal care and experimental procedures were performed under approval from the Animal Care Committees of KAIST and KRICT. A 1.5 mm hole was made in the center of both ears of FVB/N mice using a metal ear punch (Harvard Apparatus, Holliston, Mass.). For full-thickness wounding, excisions were made on the dorsal surface of the tail (Falanga et al., 2004. Wound Repair Regen. 12:320-326), approximately 0.5-1.0 cm distal to the body of the animal. A template was used to delineate 10×3 mm on the dorsal surface of the mouse tail. Full-thickness wounds corresponding to the template area were created with the use of individual sterile #10 gauge scalpels (Becton Dickinson, Franklin Lakes, N.J.). Bleeding was stopped by simple application of pressure to the wound, and the wounds were covered with a film spray dressing (Cavilon, 3M, St. Paul, Minn.). Postoperatively, mice were kept warm and their temperature was monitored for 3 days after surgery. To prevent postoperative infection, trimethoprim sulfa (Sulfatrim Pediatric suspension) was added for 5 days to the drinking water. Harvesting of ears and tails for wound closure analysis required anesthesia, which was performed by intramuscular injection of a combination of anesthetics (80 mg/kg ketamine and 12 mg/kg xylazine) during the course of the study from day 0 (right after wounding) until 8 weeks after wounding. For adenoviral treatment, $1\times10^9$ pfu Ade-COMP-Ang1 or control virus diluted in 50 μL of sterile 0.9% NaCl was injected intravenously through the tail vein 12 hrs after wounding. To detect circulating COMP-Ang1, we used an established enzyme-linked immunosorbent assay (ELISA) protocol (Cho et al., 2005, Circ. Res. 97:86-94). In Ade-COMP-Ang1 treated diabetic (db/db) mice, circulating COMP-Ang1 levels increased as early as 12 hrs (355±98 ng/ml), peaked at 1 week (3.221±365 ng/ml), declined gradually and returned to a control level at 6 weeks after Ad-COMP-Ang1 administration, similar to previous findings in Ade-COMP-Ang1 treated FVB/N mice (Cho et al., 2005, Circ Res. 97:86-94). For protein treatment, 100 μg of COMP-Ang1 recombinant protein or BSA dissolved in 50 μL of sterile 0.9% NaCl was directly applied to wound sites before the film spray dressing on the first day and applied primarily to exposed marginal wound areas between the film spray dressing and non-wound areas on a daily basis for the next 4 weeks after wounding. Applied proteins were mainly distributed at the edges of wounds around the dressing film during the first week and became evenly distributed to the entire wound area during the remaining three weeks.

Example 2.2

Morphometric Analysis of Wound Closure

Mice were anesthetized by intramuscular injection of a combination of anesthetics (80 mg/kg ketamine and 12 mg/kg xylazine) and placed supine on a warming pad. Tail and ear wounds were photographed with a digital camera (Coolpix 8400, Nikon, Tokyo, Japan). The sizes of tail wounds area ($mm^2$) were calculated from wound perimeter tracing using a photographic analysis in ImageJ software (http://rsb.info.nih.gov/ij), and all tail wound areas were interpreted as 100% on day 0 of the week of wounding; wound areas on subsequent days were expressed as a percentage of the day 0 area.

Example 2.3

Histologic and Morphometric Analysis

Mice were fixed by vascular perfusion of 1% paraformaldehyde in PBS, ears and tails were removed, and tissues embedded in paraffin (for hematoxylin and eosin staining) or cryo-freezing medium (for immunostaining). Paraffin sections (6 μm-thickness) and cryo-sections (20 μm-thickness) were prepared and incubated for 1 hr at room temperature with a blocking solution containing 5% normal goat serum (Jackson ImmunoResearch Laboratories Inc., West Grove, Pa.) in PBS with 0.3% Triton X-100 (PBST). Sections were incubated for 2 hr at room temperature with one or more primary antibodies: (a) for blood vessels, anti-PECAM-1 antibody, hamster clone 2H8, 1:100 (Chemicon International Inc., Temecula, Calif.); (b) for lymphatic vessels, anti-mouse LYVE-1 antibody, rat monoclonal antibody, 1:100 (Aprogen, Daejeon, Korea); (c) for fibroblasts, FITC-conjugated anti-α-SMA antibody, mouse clone 1A4, 1:200 (Sigma-Aldrich, St. Louis, Mo.); (d) for proliferating cells, anti-Ki67 antibody, rabbit polyclonal antibody, 1:100 (Novocastra Laboratories Ltd., Newcastle, UK); (e) and for neural cells, anti-neurofilament antibody, rabbit polyclonal antibody, 1:100 (Chemicon International Inc.). After several washes in PBST, sections were incubated for 1 hr at room temperature with one or more secondary antibodies: (a) Cy3-conjugated anti-hamster IgG antibody, 1:500 (Jackson ImmunoResearch Laboratories Inc.); (b) FITC-conjugated anti-rat antibody or anti-rabbit antibody, 1:500 (Jackson ImmunoResearch Laboratories Inc.). For control experiments, the primary antibody was omitted or substituted with preimmune serum. Signals were visualized and digital images were obtained using a Zeiss Apotome microscope and a Zeiss LSM 510 confocal microscope equipped with argon and helium-neon lasers (Carl Zeiss, Jena, Germany). The extent of wound healing in the ear (mm) was measured by photographic analysis of immunofluorescent images with image analysis software (LSM image viewer, Carl Zeiss). The parameters of epidermal and dermal regeneration, the thickness of tissue granulation, and thickness of epidermis were evaluated with HE stained sections and scored. Area densities (percentage of tissue area) of blood and lymphatic vessels were measured by PECAM-1- and LYVE-1-immunopositive blood and lymphatic vessels, respectively, at a magnification of ×200 in 5 regions, each 0.21 $mm^2$ area, per section.

Example 2.4

Measurement of Tissue Blood Flow in Wound Areas

After mice were anesthetized by intramuscular injection of a mixture of ketamine (80 mg/kg) and xylazine (12 mg/kg), they were placed on a heated table to maintain body temperature at 37° C. A type N flowprobe (Transonic Systems Inc., Ithaca, N.Y.) was placed on venous and arterial portions of the tail wound without applying pressure, which would occlude vessels and reduce perfusion in the area of interest. The flowprobe was kept in place on the position of the highest sensitivity by a micromanipulator and connected to a laser-Doppler flowmeter (model BLF21; Transonic Systems Inc.), which can measure microcirculation in 1 $mm^3$ of tissue for real-time assessment of perfusion. These analog signals were digitized at 100 Hz (Digidata 1200, Axon Instrument, Foster City, Calif.) and continuously displayed by a data-acquisition program. The mean tissue perfusion rate (ml/min/100 g of tissue) was then analyzed using Axoscope 9.0 software (Axon Instrument).

Example 2.5

Tie1 and Tie2 Phosphorylation Assays

Human dermal microvascular endothelial cells (HDMVECs) and basal medium were purchased from Cascade Biologics (Cascade Biologics, Portland, Oreg.). Tie1 and Tie2 phosphorylation assays using HDMVECs were performed as previously described (Cho et al., 2005, Circ Res. 97:86-94; Cho et al., 2004. Proc Natl Acad. Sci. USA 101:5547-5552). All signals from immunoblottings were visualized and analyzed by densitometric scanning (LAS-1000, Fuji Film, Tokyo, Japan).

Example 2.6

Statistics

Values presented are means±standard deviation (SD). Significant differences between means were determined by analysis of variance followed by the Student-Newman-Keuls test. Statistical significance was set at $P<0.05$ or $P<0.01$.

Example 3

Figure 30:
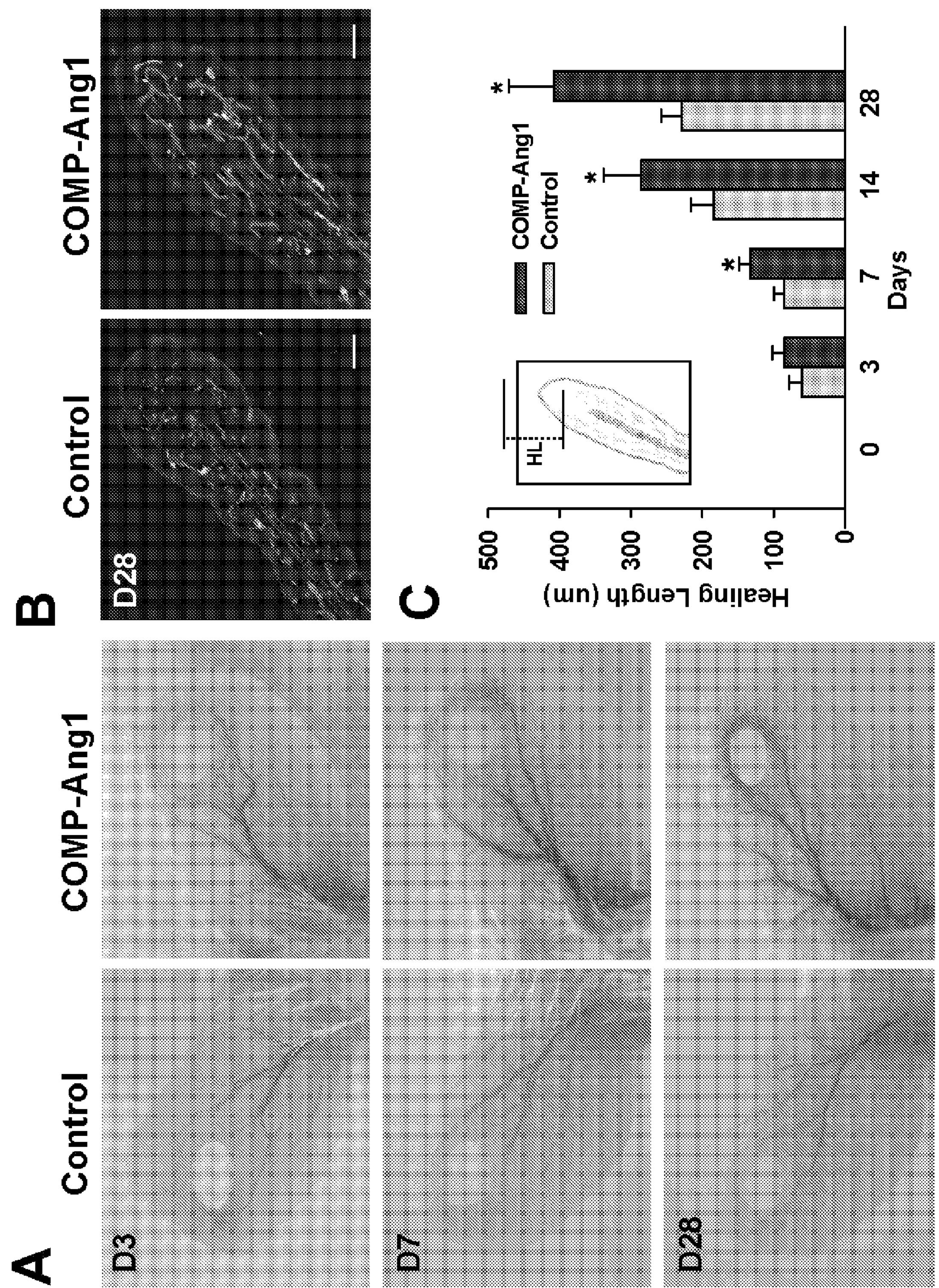
FIGS. 30A-30C show that COMP-Ang1 promotes angiogenesis, lymphangiogenesis, and wound healing in ear skin. FVB/n mice were treated with $1\times10^9$ pfu Ade-β-gal (Control) or Ade-COMP-Ang1 (COMP-Ang1) virus, and a closed punched-hole injury was made in the ear. At indicated days later, (A) ears were photographed and (C) healing length (HL) was measured. (B) Blood and lymphatic vessels of ear sections were visualized with PECAM-1 immunostaining (red) and LYVE-1 immunostaining (green) 28 days after the treatment. HL defines the distance from the initial cutting margin of cartilage to the margin of the healed portion. Mice treated with COMP-Ang1 show induced angiogenesis, lymphangiogenesis, and wound healing in ear skin. Results from 5 experiments were similar. Bars represent mean±SD from 4 mice. *, P<0.01 versus Control. Scale bar, 100 μm.
Figure 31:
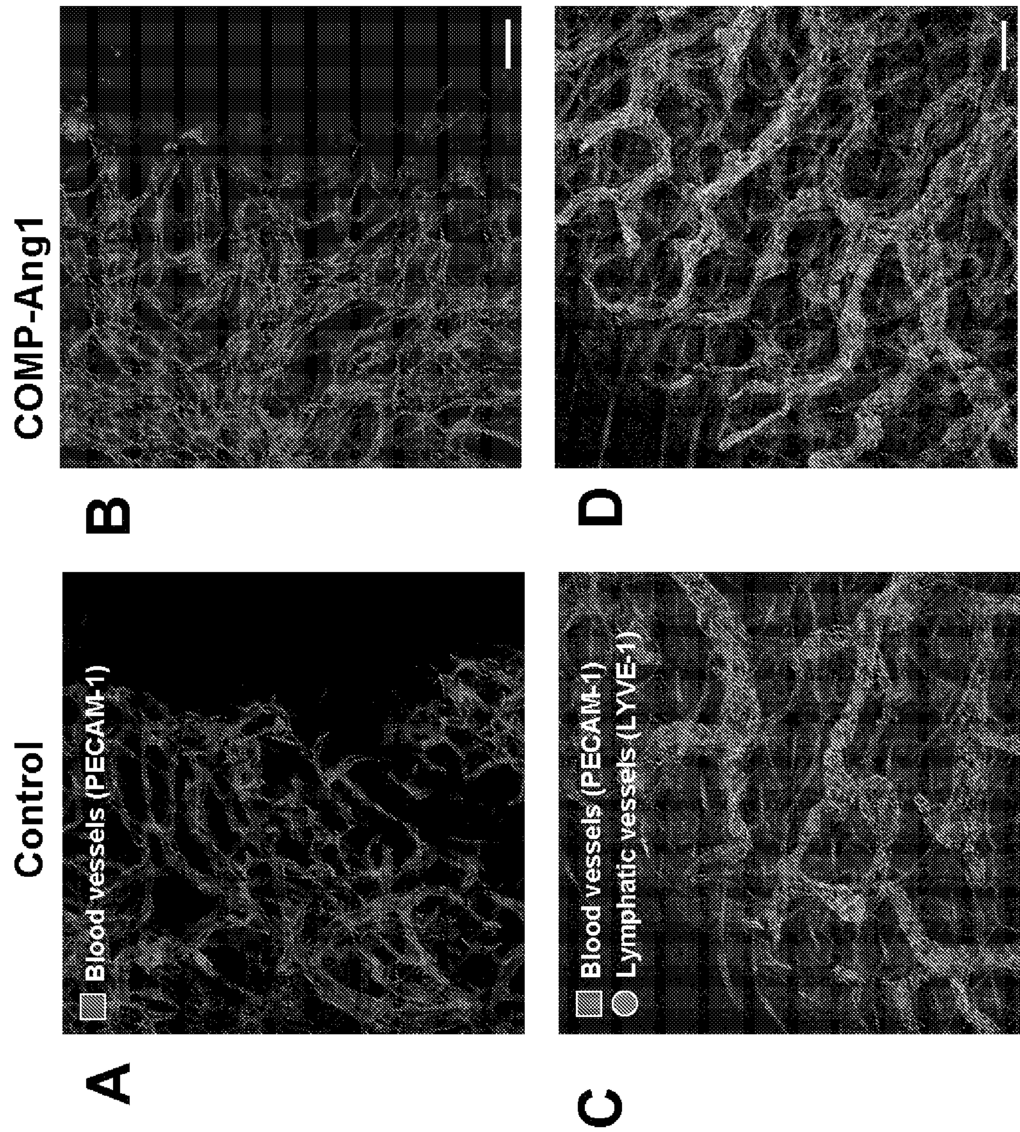
FIGS. 31A-31D show that COMP-Ang1promotes angiogenesis, lymphangiogenesis, and wound healing in ear skin. FVB/n mice were treated with $1\times10^9$ pfu Ade-β-gal (Control) or Ade-COMP-Ang1 (COMP-Ang1) virus, and a punched-hole injury was made in the ear. Seven days later, blood vessels at the margins of the injury (arrows) (A) and blood and lymphatic vessels in normal regions (B) of the ear skin were visualized with PECAM-1 (red) and LYVE-1 (green) immunostaining. Mice treated with COMP-Ang1 show enlarged and dense blood vessels in the wound margin (B) and enlarged blood vessels but no distinguishable lymphatic vessels in normal regions (D) compared to the mice treated with control virus (A) and (C). Results from 4 experiments were similar. Bars represent mean ± SD from 4 mice. *, P<0.01 versus control. Scale bar, 50 μm.

COMP-Ang1 Promotes Angiogenesis, Lymphangiogenesis, and Wound Healing in Ear Skin of Normal Mice To investigate the wound-healing process in vivo, we made ear punch injuries in mice that were treated systemically with $1\times10^9$ pfu of Ade-COMP-Ang1 or with $1\times10^9$ pfu of Ade-β-gal, which are hitherto referred to as COMP-Ang1 or control unless otherwise specified. At both 3 and 7 days after injury, larger numbers of delicate vessels were observed around the margin of punched-hole injuries in mice treated with COMP-Ang1 compared to mice treated with control (FIG. 30 and FIG. 31A). Moreover, blood vessels on the ipsilateral side of the ear leading from the base to the injury site were notably enlarged (FIG. 30A and FIG. 31B). These conditions persisted for up to 28 days after treatment (FIG. 30A). Moreover, we observed that wound healing in mice treated with COMP-Ang1 was accelerated compared to that seen in mice treated with control (FIGS. 30A, 30B and 30C). Immunofluorescence using the blood vessel endothelial cell marker, platelet-endothelial-cell adhesion molecule-1 (PECAM-1), and the lymphatic vessel endothelial cell marker, lymph vessel endothelial hyaluronan receptor-1 (LYVE-1) in transverse sections of injured ear revealed that COMP-Ang1-treated mice had more branched and connected blood and lymphatic vessels in the wound region than control-treated mice (FIG. 30B). The extent of wound healing was measured as the length of skin that had grown beyond the ear cartilage at the position of the initial tissue lesion. In COMP-Ang1 (n=5) versus controls (n=5) that length was 133±17 mm versus 86±16 mm on day 7, P<0.01; 286±53 mm versus 184±32 mm on day 14, P<0.01; and 408±63 mm versus 229±29 mm on day 28, P<0.01 (FIG. 30C). These observations suggest that more efficient wound healing in the ear in mice treated with COMP-Ang1 resulted from enhanced angiogenesis and lymphangiogenesis in the injured area. In addition, COMP-Ang1 could enhance angiogenesis, lymphangiogenesis and blood flow through activation of its receptors, Tie2 and Tie1, which are abundantly expressed in cutaneous blood and lymphatic vessels (Babaei et al., 2003. Am J Pathol. 162:1927-1936).

COMP-Ang1 accelerates wound healing with promoted angiogenesis, lymphangiogenesis and blood flow in tail skin of diabetic mice.

Figure 32:
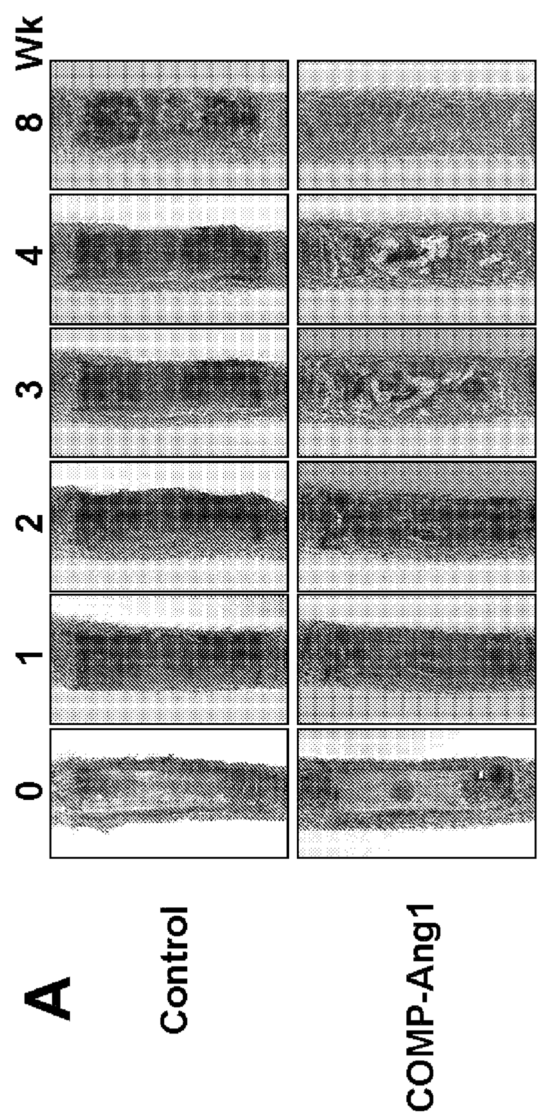
FIGS. 32A-32F show that COMP-Ang1 accelerates wound healing in tail skin of diabetic mice. An excisional full-thickness wounding (approximate area, 30 $mm^2$) was made in the tail skin of diabetic db/db mice, and mice were treated with $1\times10^9$ pfu Ade-β-gal (Control) or Ade-COMP-Ang1 (COMP-Ang1) virus. At indicated weeks later, tails were photographed (A), wound areas were measured (B), and regenerative activities of epidermis and dermis (D), granulation thickness (E) and epidermal thickness (F) were measured. ND, not determined. (C) Representative photographs of hematoxylin-eosin (HE) staining, and α-smooth muscle actin (α-SMA) and PECAM-1 immunostaining of sections of wound areas of mice treated with COMP-Ang1 and control virus 8 weeks after treatment. Results from 5 experiments were similar. Bars represent means±SD from 5 mice. *, P<0.01 versus control at each week. Scale bar, 100 μm.
Figure 32:
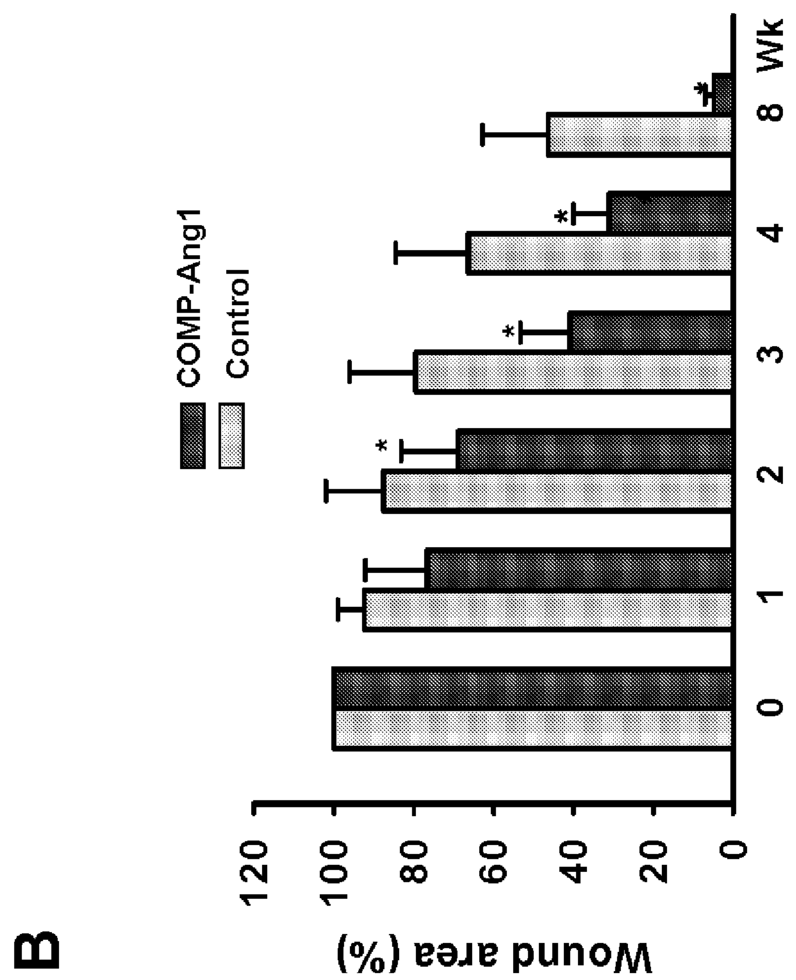
Figure 32:
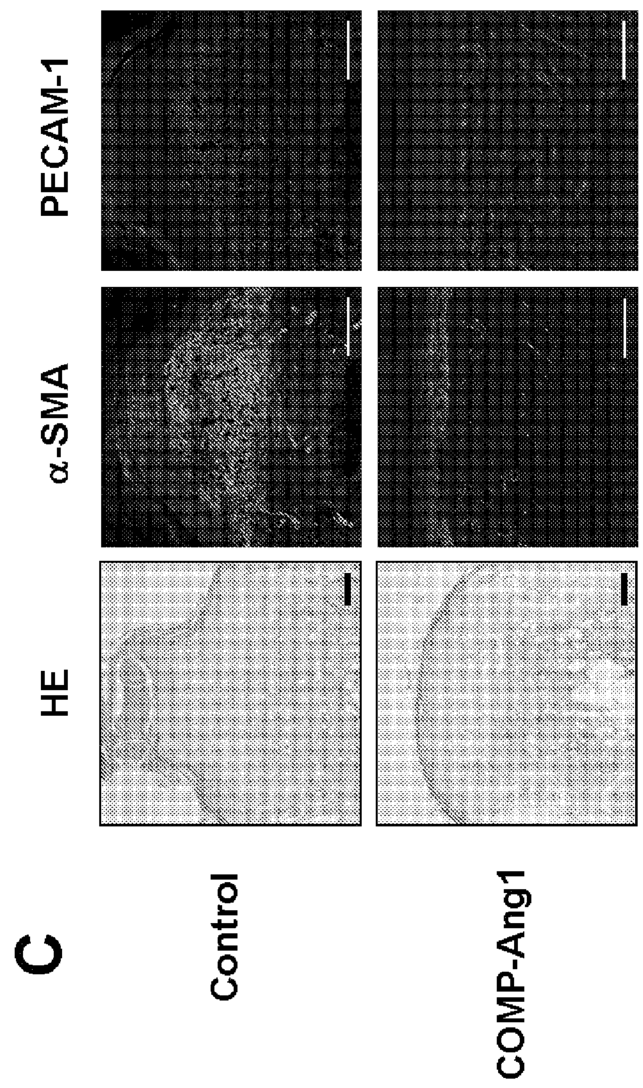
Figure 32:
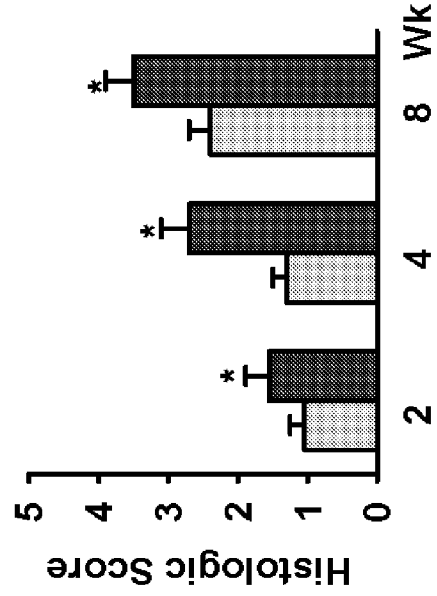
Figure 32:
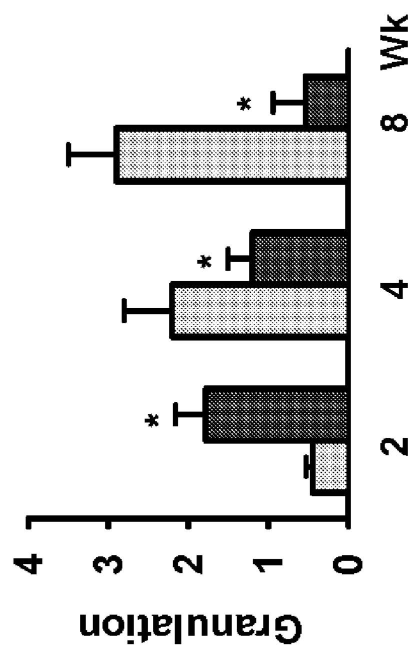
Figure 32:
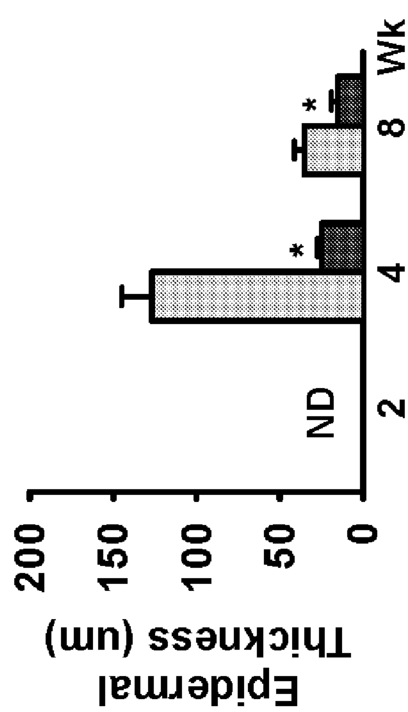

These above results led us to investigate the effect of COMP-Ang1 on delayed cutaneous wound healing seen in diabetes, which is mainly caused by microangiopathy (The Diabetes Control and Complications Trial Study Group. 1993, N Engl J Med. 329:977-986; Martin et al., 2003, Med Res Rev. 23:117-145; Laing et al., 1998, Am J Surg. 176:11 S-19S; Reiber et al., 1999, Diabetes Care. 22:157-162). To examine the effectiveness of COMP-Ang1 in promoting healing of cutaneous wounds in diabetic mice, we made excisional full thickness wounds in the dorsal side of the tail, where contraction is minimal (Saharinen et al., 2005, J. Cell Biol. 169:239-243), of diabetic C57BLKS/J-m+/+$Lepr^{db}$ (db/db) mice (Coleman, 1982, Diabetes. 31:1-6), whose phenotype resembles that of human adult-onset type II diabetes mellitus. COMP-Ang1 or control was administered intravenously 12 hours after wounding. Time course observations indicated that mice treated with COMP-Ang1 showed accelerated wound closure compared to mice treated with control. Wound closure was measured as area of epidermal closure ($mm^2$) from the initial wound after treatment. Values for COMP-Ang1 (n=5) versus control (n=5) mice were 9.3±0.9 $mm^2$ versus 3.7±0.7 $mm^2$ at 2 weeks, P<0.05; 20.7±5.9 $mm^2$ versus 10.1±1.5 $mm^2$ at 4 weeks, P<0.01; and 28.6±3.2 $mm^2$ versus 16.1±5.7 $mm^2$ at 8 weeks, P<0.01 (FIGS. 32A and 32B). Unlike topical application of human VEGF (Galeano et al., 2003, Diabetologia. 46:546-555; Galiano et al., 2004, Am J. Pathol. 164:1935-1947), obvious edema formation and vascular leakage were not observed in wound beds during wound healing after administration of COMP-Ang1. Histological analysis (Table 2) over time indicated that mice treated COMP-Ang1 displayed accelerated epidermal and dermal regeneration, accelerated formation and deformation of granulation tissue reflected by thickness of α-smooth muscle actin positive fibroblast cell layers, and thinner epidermal thickness compared to mice treated with control virus (FIGS. 32C, 32D, 32E and 32F).

TABLE 2

Criteria to evaluate histological scores of wound healing

| Score | Epidermal and dermal regeneration | Granulation thickness |
|---|---|---|
| 0 | Very little | Thin organization |
| 1 | Little | Moderate organization |
| 2 | Moderate | Thick organization |
| 3 | Complete | Very Thick |

Figure 33:
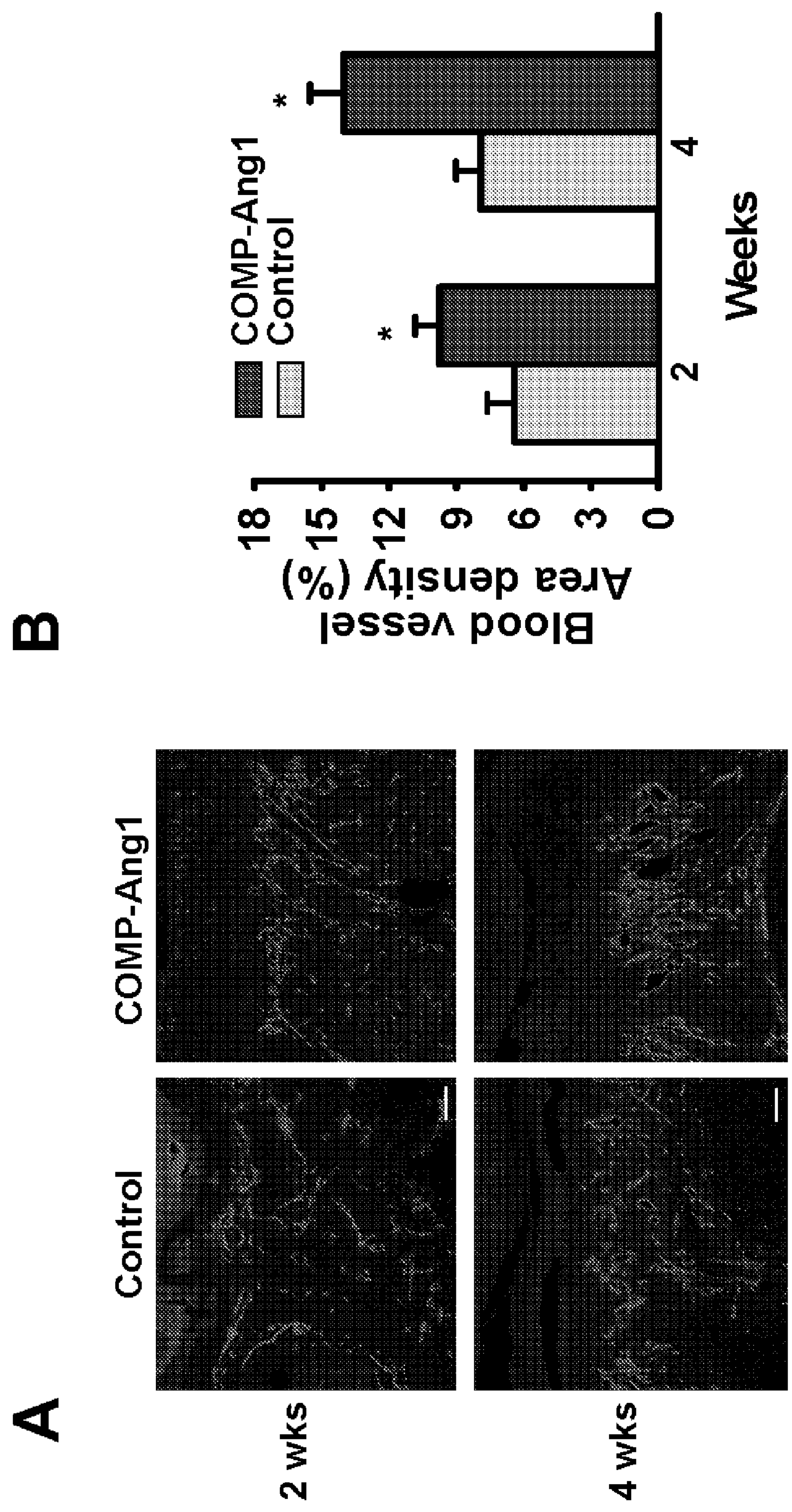
FIGS. 33A-33F show that COMP-Ang1 promotes angiogenesis and blood flow in the wound portion of tail skin. An excisional full-thickness wounding (approximate area, 30 $mm^2$) was made in the tail skin of diabetic db/db mice, and mice were treated with $1\times10^9$ pfu Ade-β-gal (Control) or Ade-COMP-Ang1 (COMP-Ang1) virus. Two (A) and four (A and C) weeks later, blood and lymphatic vessels were visualized with PECAM-1 (red) (A) and LYVE-1 (green) (C) immunostaining and area densities of blood and lymphatic vessels were measured (B and D). (E) Using a Laser-Doppler flowmeter, tissue blood flow in right (1,4,7) and left (3,6,9) venous portions and central arterial portions (2,5,8) of the wound area in the dorsal tail surface was measured. (F) Quantification of skin blood flow at the regions depicted by numbers in F was performed 4 weeks after treatment with Control or COMP-Ang1 virus. Bars represent means±SD from 5 mice. *, P<0.05 versus control. Scale bar, 50 μm.
Figure 33:
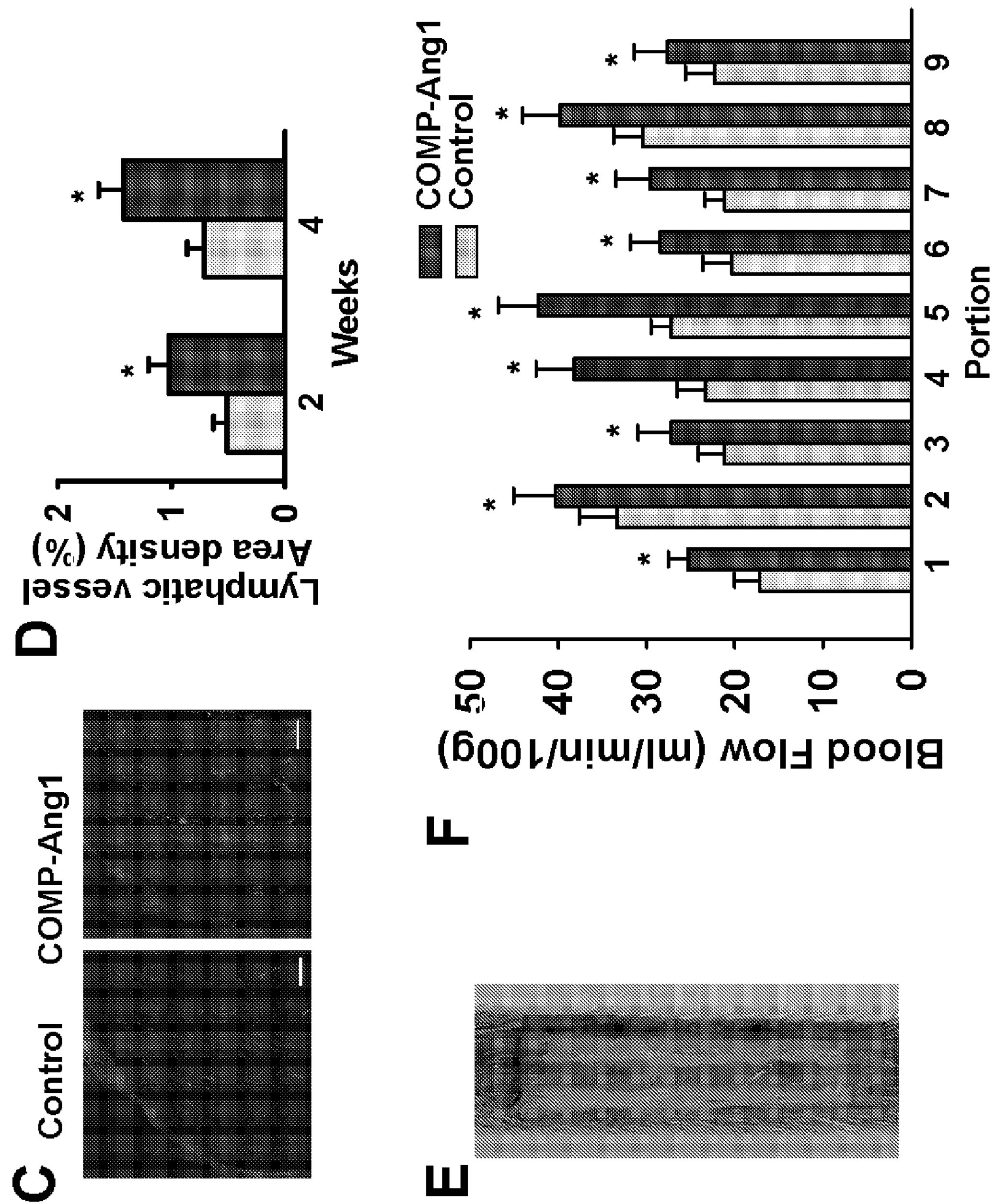
Figure 34:
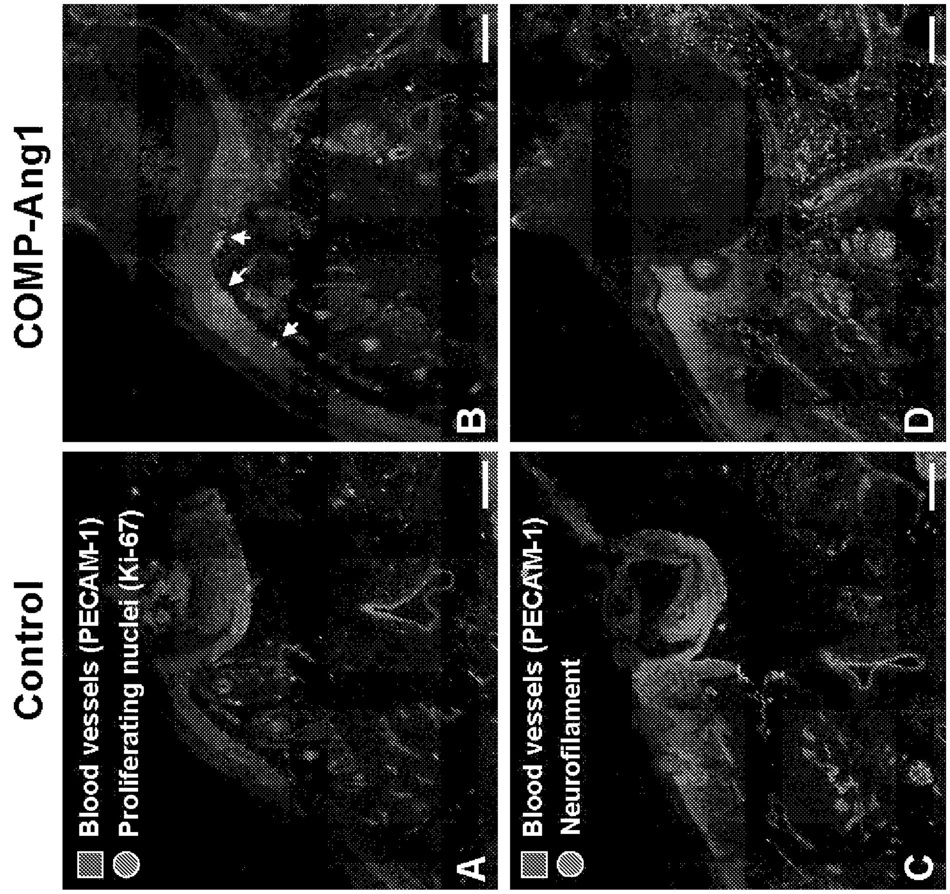
FIGS. 34A-34D show that COMP-Ang1 promotes proliferative activity of epidermal basal cells and increases the number of neurofilament-positive cells in the dermis of the wound area of tail skin. Diabetic db/db mice were treated with $1\times10^9$ pfu Ade-β-gal (A and C, Control) or Ade-COMP-Ang1 (B and D, COMP-Ang1) virus, and an excisional full-thickness wound injury (area, 30 $mm^2$) was made in the tail skin. Two weeks later, blood vessels were visualized with PECAM-1 immunostaining (red) and proliferating cells were visualized with Ki-67 immunostaining (green) (A and B). Neural cells were visualized with neurofilament immunostaining (green) (C and D) in tail sections. Mice treated with COMP-Ang1 show more proliferating cells in basal cells of the epidermis and more neurofilament immunopositive cells than control mice. The results from 4 experiments were similar. Scale bar, 50 μm.

In addition, overall blood vessel densities (PECAM-1 immuno-positive areas/total areas) in the regenerated dermis of COMP-Ang1-treated mice (n=5) were 1.52 fold (P<0.01) and 1.77 fold (P<0.01) greater than observations of control mice (n=5) at 2 and 4 weeks, respectively, after treatment (FIGS. 33A and 33B). Moreover, overall lymphatic vessel densities (LYVE-1 immuno-positive areas/total areas) in the regenerated dermis of COMP-Ang1-treated mice (n=5) were 2.06 fold (P<0.01) and 2.01 fold (P<0.01) greater than those observed in control mice (n=5) at 2 and 4 weeks, respectively, after treatment (FIGS. 33C and 33D). Thus, mice treated with COMP-Ang1 showed enhanced angiogenesis and lymphangiogenesis with enlarged blood and lymphatic vessels in the regenerated dermis compared to mice treated with control. Using a Laser-Doppler flowmeter, tissue blood flow in regions of the right and left veins and in the central artery of mice wounded on the dorsal side of tails was measured (FIG. 33E). Overall blood flow rates (ml/min) in wounded vein regions of COMP-Ang1-treated mice (n=5) were 1.21-1.44 fold (P<0.01) and 1.23-1.64 fold (P<0.01) greater than control-treated mice (n=5) at 2 and 4 weeks, respectively, after treatment (FIGS. 33E and 33F). Overall blood flow rates (ml/min) in wounded arterial regions of COMP-Ang1-treated mice (n=5) were 1.15-1.32 fold (P<0.01) and 1.20-1.56 fold (P<0.01) greater than control mice (n=5) at 2 and 4 weeks, respectively, after treatment (FIGS. 33E and 33F). These results suggest that COMP-Ang1-induced acceleration of wound healing in diabetic mice could be mediated by relief of ischemia in diabetic skin through COMP-Ang1-induced enhanced blood flow. In addition, mice treated with COMP-Ang1 showed higher proliferative activity of epidermal basal cells and more neurofilament-positive cells in the dermis, compared to control mice (FIG. 34). Since angiogenesis precedes development (Thurston et al., 1999, Science. 286: 2511-2514; Davis et al., 1996, Cell. 87:1161-1169; Suri et al., 1996, Cell. 87:1171-1180) and repair (Cho et al., 2005, Circ Res. 97:86-94) of organs, and blood vessels are more than just carriers of nutrient and passive filters of blood in tissues, our results indicate that COMP-Ang1 may induce basal cell and neural regeneration in diabetic wounds indirectly by multiple mechanisms.

Example 3.1

Figure 35:
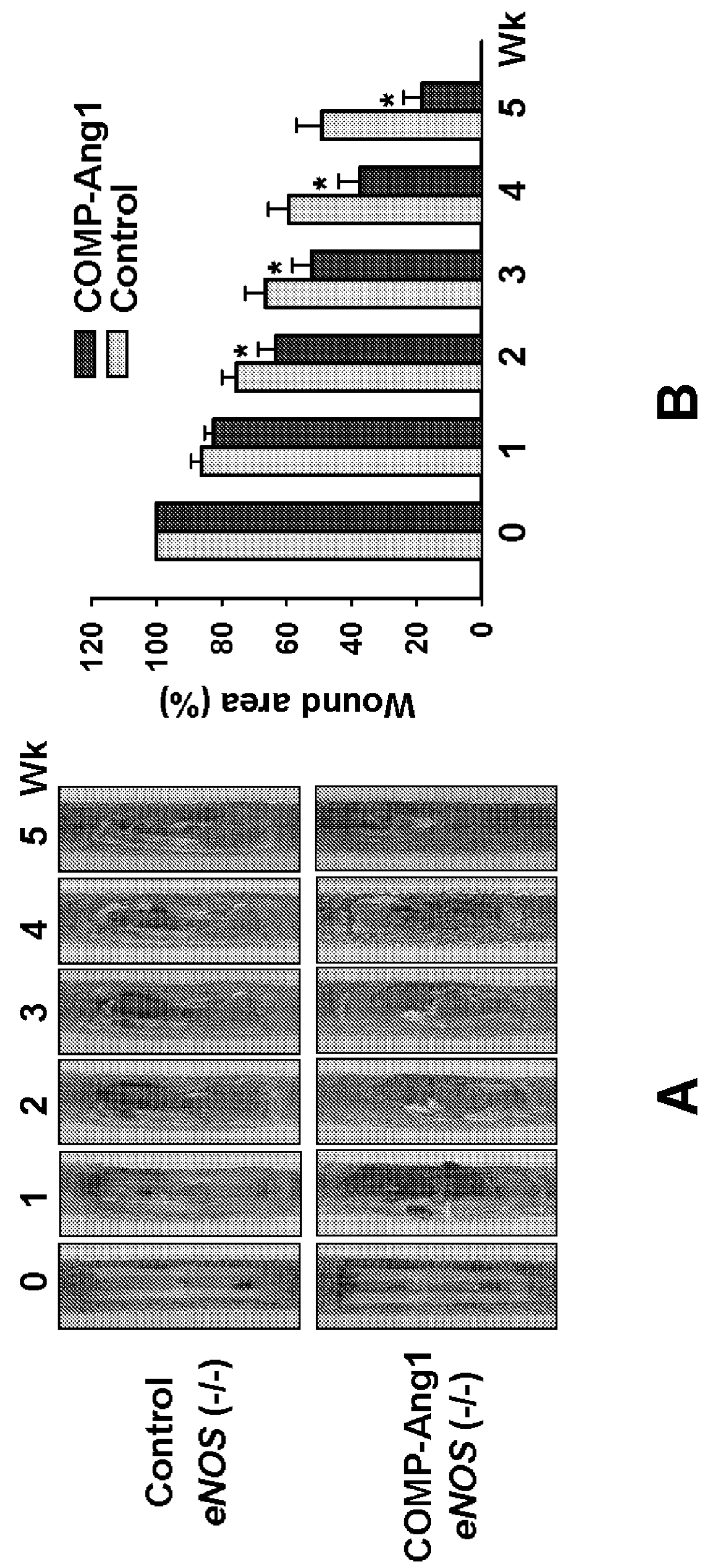
FIGS. 35A-35D show that COMP-Ang1 accelerates wound healing in tail skin of eNOS (−/−) mice and iNOS (−/−) mice. An excisional full-thickness wound (approximate area, 30 $mm^2$) was made in the tail skin of eNOS (−/−) mice, iNOS (+/+) and iNOS (−/−) mice, and the mice were treated with $1\times10^9$ pfu Ade-β-gal (Control) or Ade-COMP-Ang1 (COMP-Ang1). At the indicated weeks later, tails were photographed (A and C) and wound areas were measured (B and D). The results from 5 experiments were similar. Bars represent mean±SD from 5 mice. *, P<0.01 versus control at each week.
Figure 35:
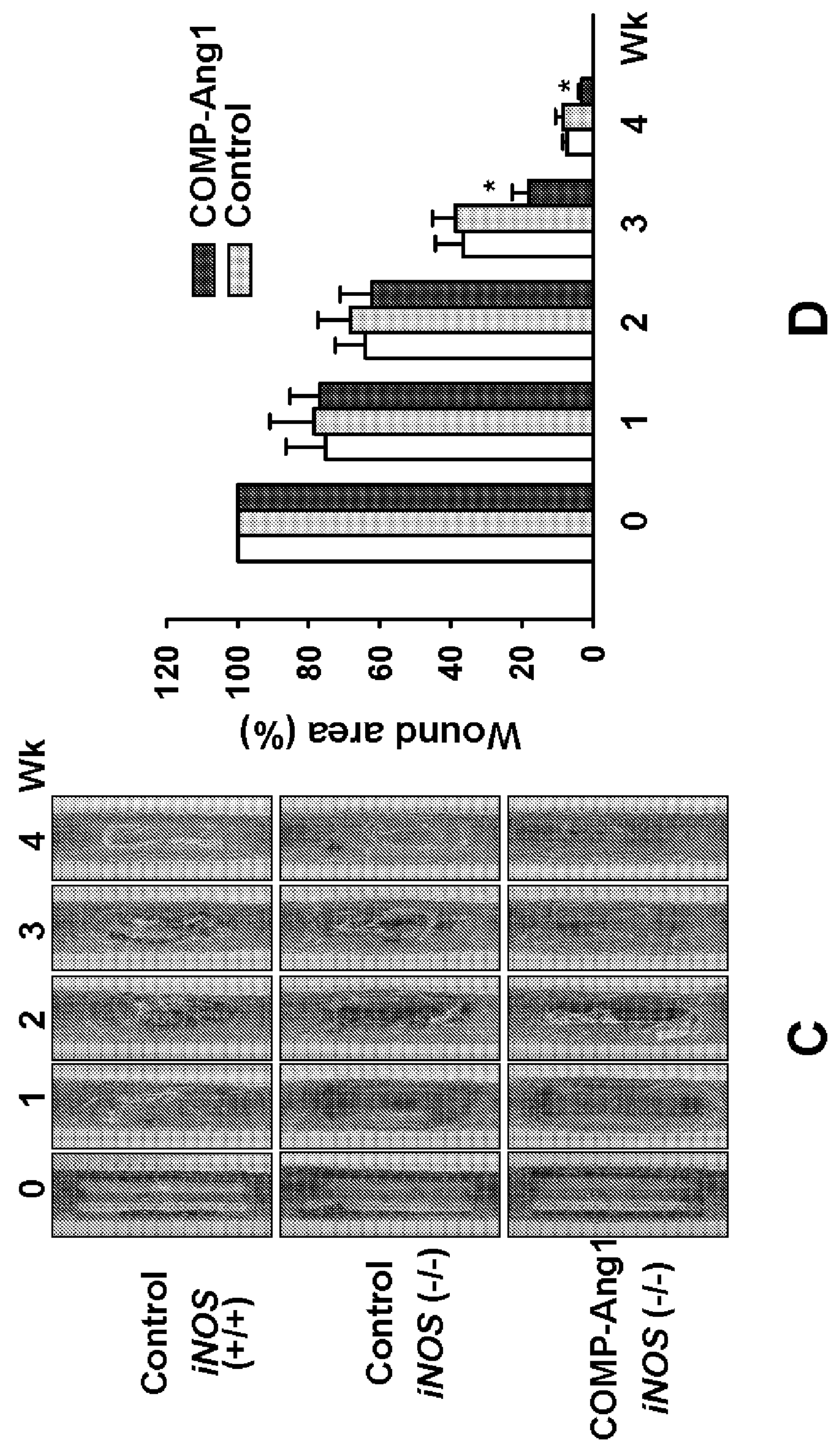

COMP-Ang1 Accelerates Wound Healing in Tail Skin of eNOS (−/−) and iNOS (−/−) Mice Endothelial nitric oxide synthase (eNOS)-induced nitric oxide plays an integral role in normal wound healing (Witte, M B and Barbul, A, 2002, Am J. Surg. 183:406-412; Schwentker et al., 2002 Nitric Oxide 7:1-10). We observed that eNOS (−/−) mice displayed impaired wound closure by approximately 40% compared to eNOS (+/+) mice in the same model of tail wounding consistent with previous findings (Lee et al., 1999, Am. J. Physiol. 277:H1600-H1608). Specifically, wound closure was measured as areas of epidermal closure ($mm^2$) from the initial wound values at 3 weeks. Values in eNOS (−/−) (n=4) versus eNOS (+/+) (n=4) mice were 11.6±2.2 $mm^2$ versus 19.4±3.5 $mm^2$, P<0.01. By contrast, inducible nitric oxide synthase (iNOS) (−/−) mice did not display delayed wound healing in the same model of tail wounding compared to iNOS (+/+) mice (FIGS. 35C and 35D). In addition, Ang1-induced angiogenesis appears to require generation of NO by activated eNOS of the endothelium (Babaei et al., 2003. Am J Pathol. 162:1927-1936). Therefore, we asked whether eNOS or iNOS participated in COMP-Ang1-induced accelerated wound healing by undertaking tail wounding in 9-10 week-old male eNOS (−/−) and iNOS (−/−) mice. Time course observations indicated that eNOS (−/−) and iNOS (−/−) mice treated with COMP-Ang1 showed accelerated wound closure compared to control mice (FIG. 35). Moreover, eNOS (−/−) and iNOS (−/−) mice treated with COMP-Ang1 showed enhanced angiogenesis compared to the mice treated with control virus. These findings indicate that enhanced angiogenesis mediated by COMP-Ang1 during wound healing in tail skin is not dependent on eNOS and iNOS.

Example 3.2

Figure 36:
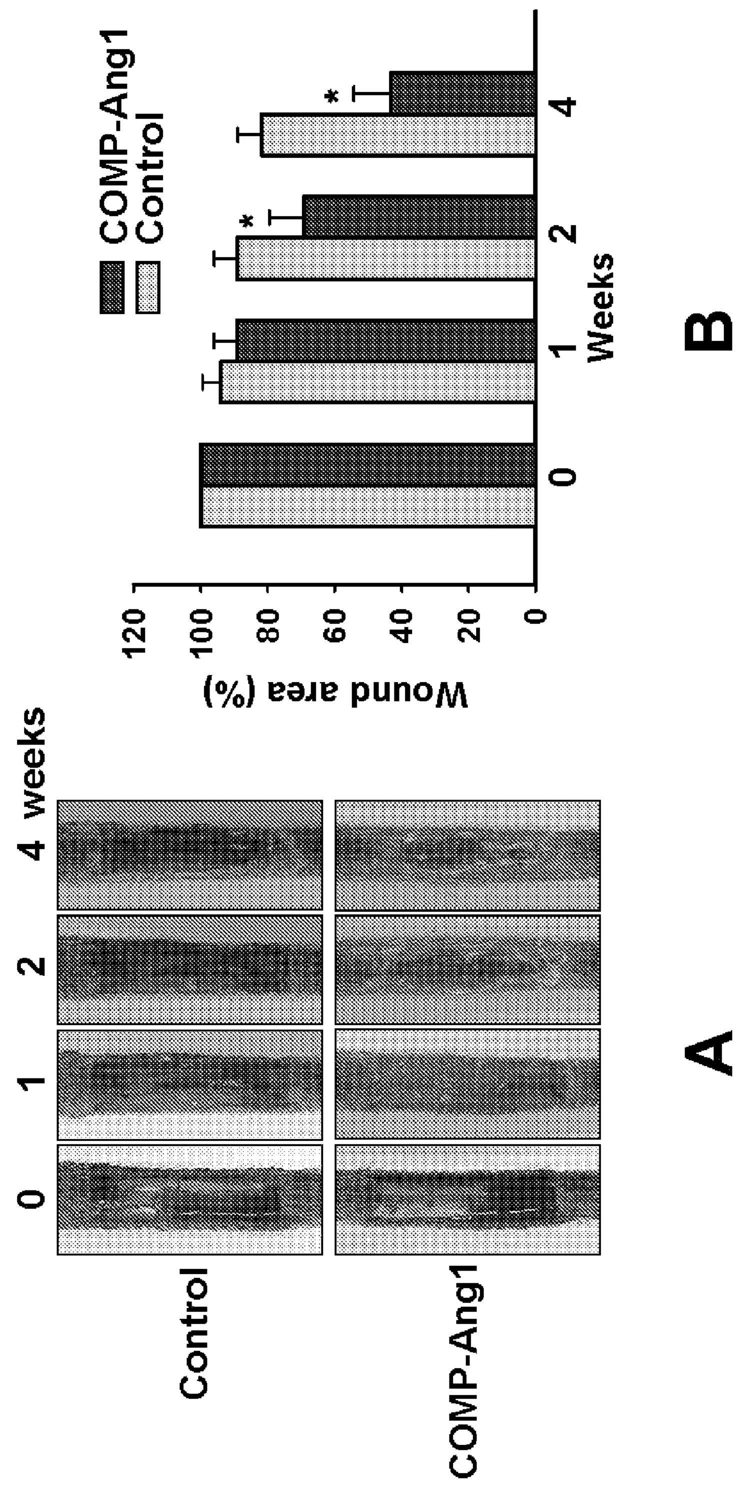
FIGS. 36A-36F show that topical COMP-Ang1 promotes wound healing with enhanced angiogenesis and blood flow in tail skin. Daily topical treatment with ~100 μg of BSA (Control) or 100 μg of COMP-Ang1 was applied to part of an excisional full-thickness wound injury (approximate area, 30 $mm^2$) in the tail skin of diabetic db/db mice. At indicated weeks later, tails were photographed (A) and wound areas were measured (B). Two or four (C and D) weeks later, blood and lymphatic vessels were visualized with PECAM-1 (red) or LYVE-1 (green) immunostaining and area densities of blood vessels were measured (E). (F) Two weeks later, tissue blood flow in right (1) and left (3) venous regions and central arterial regions (2) of the dorsal tail surface were measured. Bars represent means±SD from 6 mice. *, P<0.05 versus control. Scale bar, 50 μm.
Figure 36:
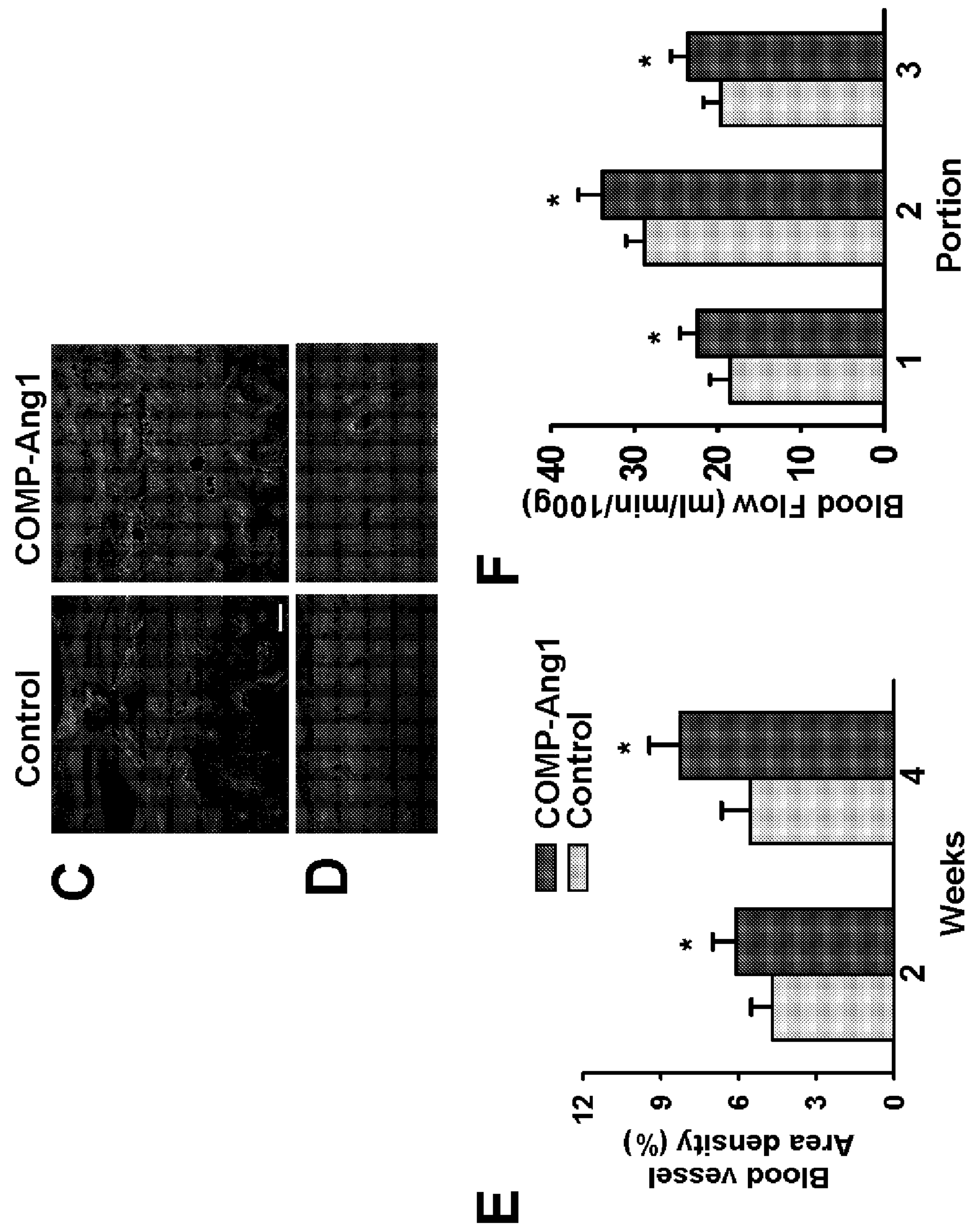

Topical COMP-Ang1 Promotes Wound Healing with Enhanced Angiogenesis and Blood Flow in Tail Skin Given that COMP-Ang1 antagonizes delayed wound healing seen in diabetic patients, we asked whether topical application of the protein could promote such an effect. To this end, a stable Chinese hamster ovary cell line producing COMP-Ang1 (CA1-2, production rate, 20-30 mg/L) was established (Cho et al., 2005, Circ Res. 97:86-94). To test the effectiveness of topical application of COMP-Ang1 protein, we directly applied 50 μl saline (0.9% NaCl) containing 100 μg of COMP-Ang1 protein on a daily basis into full thickness wounds created on the dorsal side of the tail in diabetic C57BLKS/J-m+/+$Lepr^{db}$ (db/db) mice. In parallel, wounds made in littermates were treated daily with bovine serum albumin (BSA) as a control. Wounds receiving COMP-Ang1 protein healed faster than wounds receiving BSA. In COMP-Ang1 (n=6) versus BSA (n=6), values for epidermal closure ($mm^2$) from the initial wound were 9.5±1.4 $mm^2$ versus 3.5±0.6 $mm^2$ at 2 weeks, P<0.01; and 17.0±4.4 $mm^2$ versus 5.5±0.7 $mm^2$ at 4 weeks, P<0.01 (FIGS. 36A and 36B), respectively. Likewise, wounds receiving COMP-Ang1 protein displayed enhanced angiogenesis (~1.3 fold on day 14 and ~1.5 fold at 4 weeks), lymphangiogenesis (~1.3 fold on day 14 and ~1.4 fold at 4 weeks) (FIG. 36C, 36D and 36E), and blood flow (venous portions, 1.15 to 1.28-fold at 2 weeks; arterial portions, 1.14 to 1.25-fold at 2 weeks) (FIG. 36F) compared to wounds receiving BSA.

Example 3.3

Conclusion

Systemic and topical COMP-Ang1 accelerates cutaneous wound closure with enhanced angiogenesis and lymphangiogenesis, and higher blood flow in normal and diabetic mice, and those are not dependent on eNOS and iNOS. Therefore, COMP-Ang1 is useful as a new therapeutic molecule for promoting cutaneous wound healing in diabetes Example 4

Rat Myocardial Infarction Model

Male Sprague-Dawley rats (200-220 g of body weight) were anesthetized with ketamine hydrochloride (100 mg/kg) and xylazine hydrochloride (2.5 mg/kg). The anesthetized rats were ventilated under positive pressure using a rodent ventilator (model 683, Harvard Apparatus, South Natick, Mass., USA). A left thoractomy was performed in the fourth intercostal space, and the pericardium opened. The left coronary artery was enclosed within the myocardium between the left atrial appendage and right ventricular outflow tract with a curved needle and 6-0 silk sutures, occluded, and injected with 140 μl of buffer containing 50 μg of COMP-Ang1 or bovine serum albumin into infarct zone. The chest was then closed in layers and the pneumothorax was evacuated. After 5 hours, the suture was removed, that is, so called, 'late-reperfused transmural myocardiac infarction (LMI)' model. All care and handling of animals were performed according to the Guide for the Care and Use of Laboratory Animals published by the National Institute of Health (NIH publication 85-23, revised 1985)

Example 4.1

Echocardiography to Evaluate Remodeling and Hemedynamic Factor Analysis

Transthoracic echocardiography was performed on all animals to 2 weeks after COMP-Ang1 injection into the infarct area. Briefly, rats were anesthetized with 50 mg/kg ketamine and 10 mg/kg xylazine. The chest was shaved, and the rats were placed supine. Echocardiograms were performed with a commercially available echocardiography system equipped with 7.5-MHz phased-array transducer (Hewlett-Packard). The transducer was positioned on the left anterior side of the chest after the precordium was shaved. The heart was first imaged in the 2-dimensional mode in the parasternal long- and short-axis views of the left ventricle (LV). By the use of these views, the M-mode cursor was positioned perpendicular to the ventricular septum and posterior wall; M-mode images were then obtained at the level below the tip of the mitral valve leaflets at the level of the papillary muscles. Care was taken to avoid excessive pressure. Left ventricular posterior wall thickness (LVPW) and LV internal dimensions including intact ventricular septum thickness (IVST) were measured according to the leading edge method of the American Society of Echocardiography: maximal LV end-diastolic diameter (at the time of maximal cavity dimension, LVdD), minimal LV end-systolic diameter (at the time of maximum anterior motion of the posterior wall, LVsD), and fractional shortening (FS) as a measure of systolic function. All measurements were averaged for 3 consecutive cardiac cycles and were made by an experienced technician who was blind to the treatment group.

Example 4.2

Histological and Immunohistochemical Examination

The heart was arrested in diastole by direct injection of 2-3 ml of 2 M KCl into the LV. It was then excised and transversely sectioned across the infarct into 2 blocks. The tissue blocks were 10% formalin. The fibrotic tissue in the tissue sections was stained using the Masson's trichrome method. For quantitative analysis of angiogenesis, immunofluorescent analysis was performed with anti-von-Willebrand factor (vWF) antibody in the 4 μm-thick sections.

Example 4.3

Statistical Analysis

Figure 37:
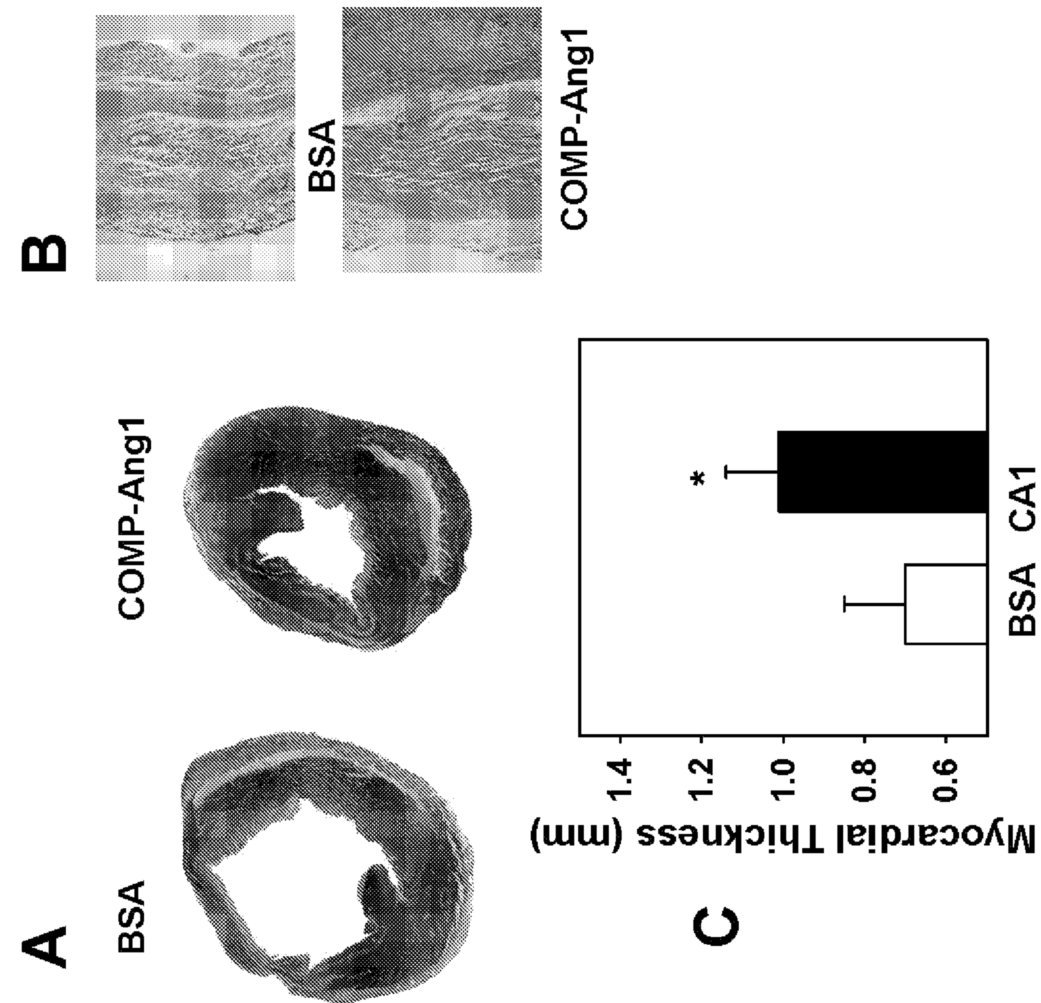
FIGS. 37A-37E show that COMP-Ang1 markedly attenuates ventricular remodeling and induces angiogenesis in the infracted hearts. LMI was made in the hearts of adult male Sprague-Dawley rats and 50 Ξg of COMP-Ang1or BSA was injected into the infarct zone. Two weeks after the treatment, the hearts were harvested. (A and B) Fibrotic tissues (blue color) and LV wall thickness were visualized with Masson's trichrome staining in the transversely cross-sectioned tissues. (C) Quantification analysis of LV wall thickness between BSA treated LMI and COMP-Ang1 (CA1)-treated LMI was performed, Bars represent mean ± SD from 5 mice. *, P<0.05 versus BSA. (D) Blood vessels (red color) were visualized with immunofluorescent staining of von-Willebrand factor. (E) Quantification analysis of vascular densities between BSA treated LMI and COMP-Ang1 (CA1)-treated LMI was performed, Bars represent mean ± SD from 5 mice. *, P<0.05 versus BSA.
Figure 37:
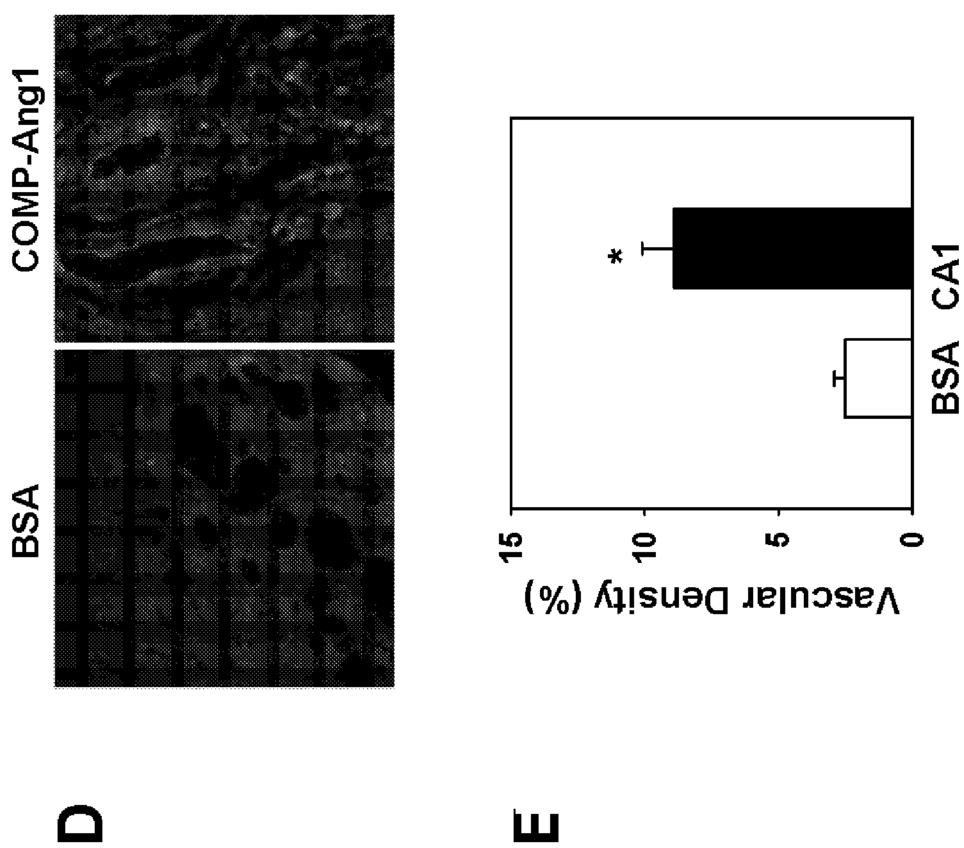
Figure 38:
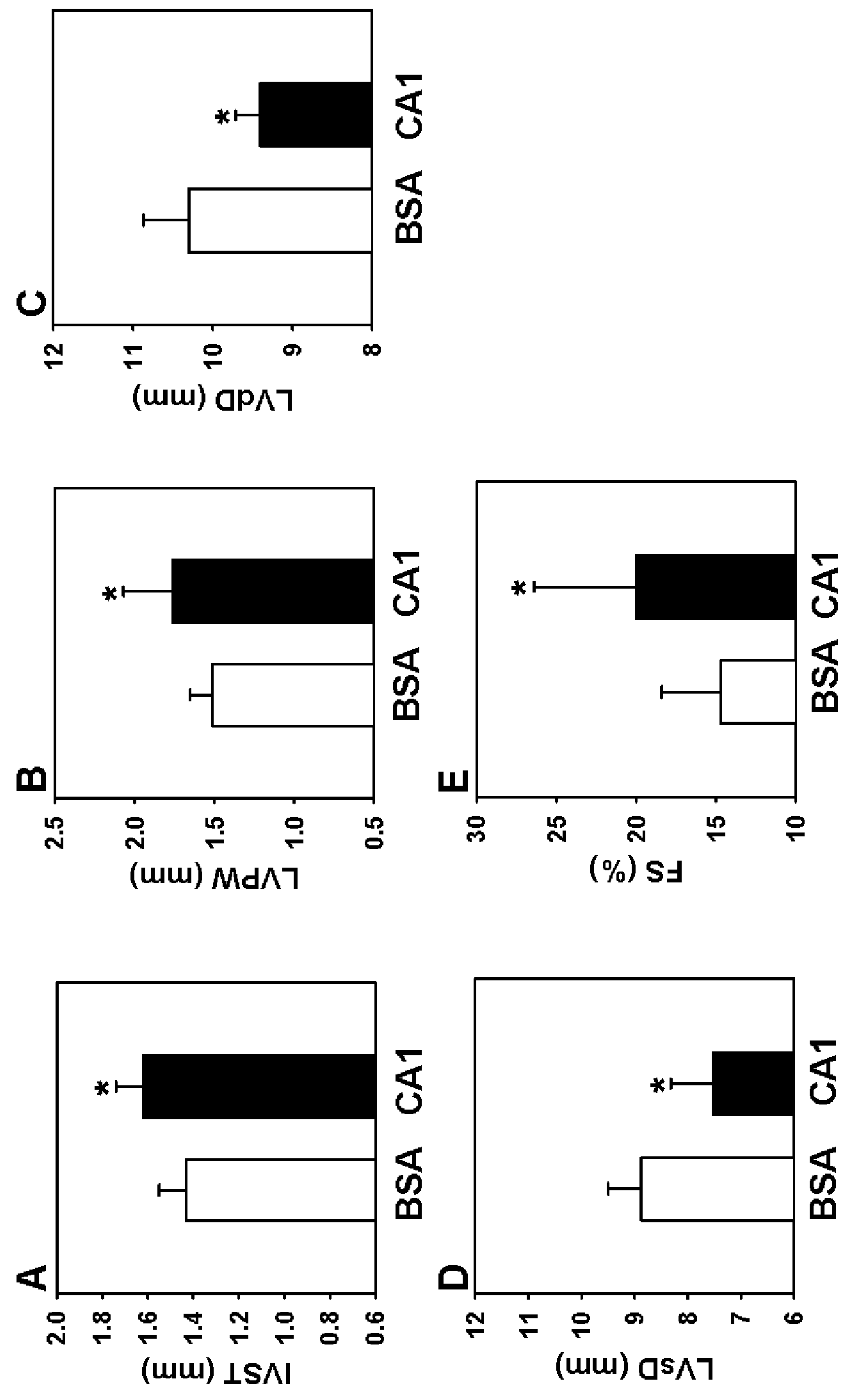
FIGS. 38A-38E show that COMP-Ang1 markedly restores ventricular functions in the infracted hearts. LMI was made in the hearts of adult male Sprague-Dawley rats and 50 μg of COMP-Ang1 or BSA was injected into the infarct zone. Two weeks after the treatment, transthoracic echocardiography was performed. IVST, LVPW, LVdD, LVsD and FS were analyzed (A-E). Bars represent mean±SD from 5 mice. *, P<0.05 versus BSA.

Data were obtained from three animals per group and expressed as the mean±standard deviation. Statistical analysis was performed using unpaired Student's t-test. A value of $p<0.05$ was considered to be statistically significant. Results: Formation of blood vessel was increased at the infarct and border-zone (FIG. 37). COMP-Ang1 markedly attenuated wall thickness of infarction zone (control versus COMP-Ang1, 0.7±0.15 versus 1.01±0.13 mm, $p<0.05$), IVST (1.43±0.12 versus 1.62±0.12 mm, $p<0.05$), LVPW (1.51±0.13 versus 1.76±0.31 mm, $p<0.05$), LVdD (10.3±0.6 versus 9.4±1.0 mm, $p<0.05$), LDsD (8.87±0.62 versus 7.52±0.15 mm, $p<0.05$), and improved FS (14.0±3.7 versus 20.0±8.4%, $p<0.05$) (FIG. 37 and FIG. 38). Injected COMP-Ang1 was largely localized in injected infarction zone at 30, 120, 240 min after the injection. Injected COMP-Ang1 was still detectable in the administered area at 330 min after the injection. Thus, COMP-Ang1 markedly attenuates left ventricular remodeling in a rat model of myocardiac infarction. These findings suggest that COMP-Ang1 is an effective molecule for therapeutic angiogenesis of the ischemic heart.

All of the references cited herein are incorporated by reference in their entirety.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

What is claimed is:

1. A method of an accelerating or promoting healing of excisional cutaneous wound comprising administering to a person in need thereof an effective amount of a coiled coil chimeric molecule comprising a coiled-coil domain of cartilage oligomeric matrix protein linked to a Tie2 receptor binding domain which is a fibrinogen-like domain of angiopoietin-1.

2. The method according to claim 1, wherein the wound is on a person suffering from diabetes.

3. The method according to claim 1, wherein the coiled coil chimeric molecule is a soluble biologically active multimer.

4. The method according to claim 3, wherein the multimer is a dimer, trimer, tetramer, pentamer, hexamer, heptamer, octamer, nanomer or decamer.

5. The method according to claim 1, wherein the coiled coil chimeric molecule is administered topically.

6. The method according to claim 5, wherein the coiled coil molecule is in liquid or powder form.

* * * * *